United States Patent
Johnston et al.

(10) Patent No.: US 12,180,487 B2
(45) Date of Patent: Dec. 31, 2024

(54) MINICIRCLE PRODUCING BACTERIA ENGINEERED TO DIFFERENTIALLY METHYLATE NUCLEIC ACID MOLECULES THEREIN

(71) Applicant: Fred Hutchinson Cancer Center, Seattle, WA (US)

(72) Inventors: Christopher Johnston, Seattle, WA (US); Sean Cotton, Cambridge, MA (US)

(73) Assignee: Fred Hutchinson Cancer Center, Seattle, WA (US)

(*) Notice: Subject to any disclaimer, the term of this patent is extended or adjusted under 35 U.S.C. 154(b) by 611 days.

(21) Appl. No.: 17/428,585

(22) PCT Filed: Feb. 6, 2020

(86) PCT No.: PCT/US2020/017095
§ 371 (c)(1),
(2) Date: Aug. 4, 2021

(87) PCT Pub. No.: WO2020/163655
PCT Pub. Date: Aug. 13, 2020

(65) Prior Publication Data
US 2022/0098599 A1    Mar. 31, 2022

Related U.S. Application Data

(60) Provisional application No. 62/802,016, filed on Feb. 6, 2019.

(51) Int. Cl.
| | | |
|---|---|---|
| *C12N 15/10* | (2006.01) | |
| *C12N 1/20* | (2006.01) | |
| *C12N 9/10* | (2006.01) | |
| *C12N 15/70* | (2006.01) | |
| *C12N 15/74* | (2006.01) | |
| *C12R 1/19* | (2006.01) | |

(52) U.S. Cl.
CPC ............. *C12N 15/70* (2013.01); *C12N 1/205* (2021.05); *C12N 9/1007* (2013.01); *C12N 15/74* (2013.01); *C12R 2001/19* (2021.05)

(58) Field of Classification Search
None
See application file for complete search history.

(56) References Cited

U.S. PATENT DOCUMENTS

| | | |
|---|---|---|
| 2006/0194214 A1 | 8/2006 | Church et al. |
| 2010/0076057 A1 | 3/2010 | Sontheimer et al. |
| 2013/0216579 A1 | 8/2013 | Fidock et al. |
| 2016/0074505 A1 | 3/2016 | Kovarik et al. |
| 2016/0186147 A1 | 6/2016 | Cady et al. |

FOREIGN PATENT DOCUMENTS

| | | | |
|---|---|---|---|
| WO | 2015148680 A1 | 10/2015 | |
| WO | 2018/071841 | * | 4/2018 |
| WO | 2018071841 A1 | 4/2018 | |

OTHER PUBLICATIONS

Gaspar et al (Human Gene Therapy Methods. Nov. 2013. 25(2): 93-105).*
Kay et al (Nature Biotech. Nov. 2010. 28(1): 1287-1289).*
Gaspar et al., "Improved Minicircle DNA Biosynthesis for Gene Therapy Applications," *Human Gene Therapy Methods* 25:93-105, Apr. 2014. (13 pages).
Huo et al., "Genome Modification in *Enterococcus faecalis* OIRF Assessed by Bisulfite Sequencing and Single-Molecule Real-Time Sequencing," *Journal of Bacteriology* 197(11):1939-1951, Jun. 2015. (13 pages).
International Search Report and Written Opinion, dated Jan. 18, 2018, for International Patent Application No. PCT/US2017/056626. (16 pages).
Kay et al., "A robust system for production of minicircle DNA vectors," *Nature Biotechnology* 28(12):1287-1289, Dec. 2010. (6 pages).
Khlebnikov et al., "Homogeneous expression of the $P_{BAD}$ promoter in *Escherichia coli* by constitutive expression of the low-affinity high-capacity AraE transporter," *Microbiology* 147:3241-3247, Dec. 1, 2001. (8 pages).
Kim et al., "Improvement of Transformation Efficiency Through In Vitro Methylation and SacII Site Mutation of Plasmid Vector in *Bifidobacterium longum* MG1," *J. Microbiol. Biotechnol.* 20(6): 1022-1026, Apr. 19, 2010. (5 pages).
Marraffini et al., "CRISPR Interference Limits Horizontal Gene Transfer in Staphylococci by Targeting DNA," *Science* 322(5909): 1843-1845, Dec. 19, 2008. (8 pages).
Motherway et al., "Identification of Restriction-Modification Systems of *Bifidobacterium animalis* subsp. *lactis* CNCM I-2494 by SMRT Sequencing and Associated Methylome Analysis," *PLoS One* 9(4): e94875, Apr. 2014. (10 pages).
Murray, "Type I Restriction Systems: Sophisticated Molecular Machines (a Legacy of Bertani and Weigle)," *Microbiology and Molecular Biology reviews* 64(2):412-434, Jun. 2020. (23 pages).
Oliveira et al., "The interplay of restriction-modification systems with mobile genetic elements and their prokaryotic hosts," *Nucleic Acids Research* 42(16):10618-10631, Aug. 12, 2014. (15 pages).

(Continued)

*Primary Examiner* — Jennifer E Graser

(74) *Attorney, Agent, or Firm* — Seed IP Law Group LLP

(57) ABSTRACT

Embodiments include engineered minicircle-producing bacterium with differential methylation capability, as well as kits and compositions comprising the bacterium. Further described are methods of using of the bacterium for producing differentially methylated minicircle DNA, and for improving transformation efficiency of exogenous DNA in intractable bacteria.

12 Claims, 23 Drawing Sheets
Specification includes a Sequence Listing.

(56) References Cited

OTHER PUBLICATIONS

Price et al., "CRISPR-Cas and Restriction-Modification Act Additively against Conjugative Antibiotic Resistance Plasmid Transfer in *Enterococcus faecalis*," *Molecular Biology and Physiology 1*(3):e00064-16, Jun. 1, 2016. (13 pages).
Sater et al., "DNA Methylation Assessed by SMRT Sequencing Is Linked to Mutations in Neisseria meningitidis Isolates," *PLoS One 10*(12): e0144612, Dec. 11, 2015. (19 pages).
Wang et al., "Premethylation of Foreign DNA Improves Integrative Transformation Efficiency in *Synechocystis* sp. Strain PCC 6803," *Applied and Environmental Microbiology 81*(24):8500-8506, Dec. 2015. (7 pages).

\* cited by examiner

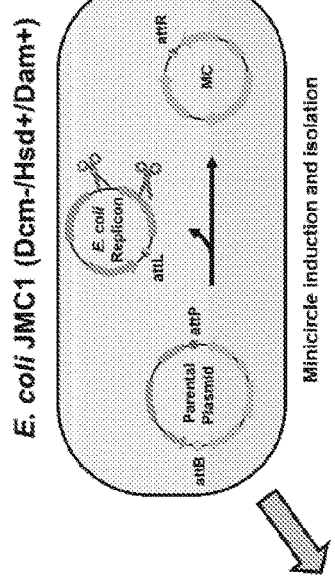
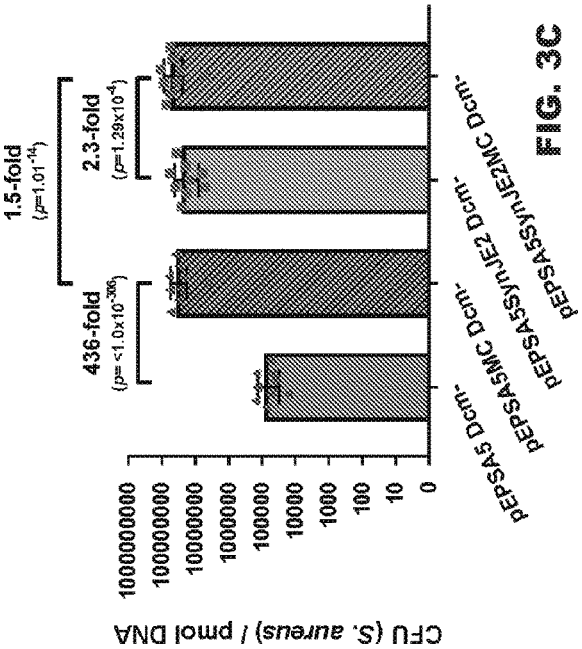
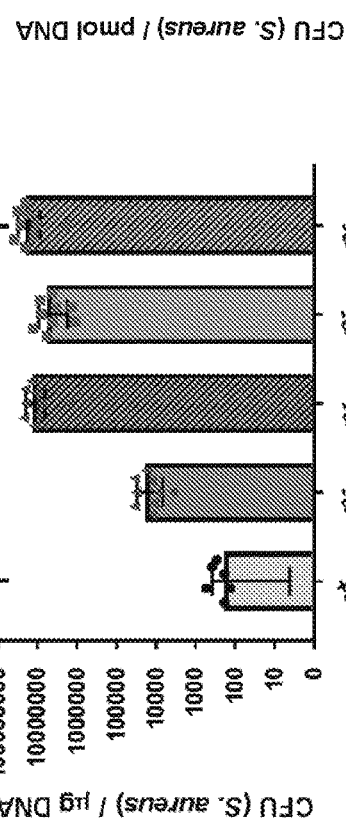
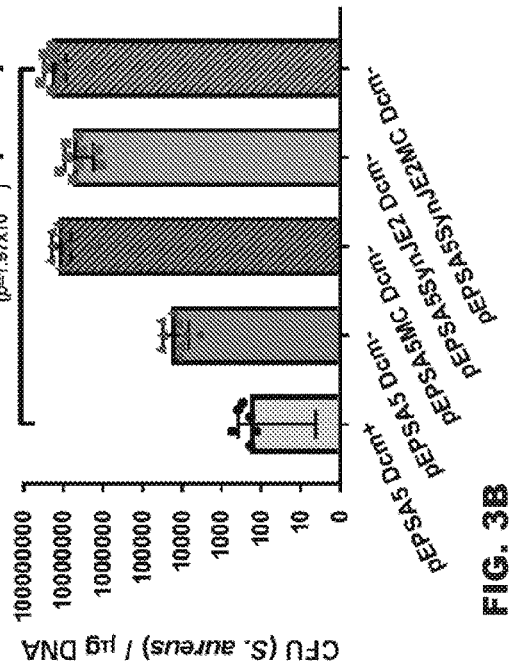
FIG. 3A
FIG. 3B
FIG. 3C

E. coli MC (EcoMC) Dcm system
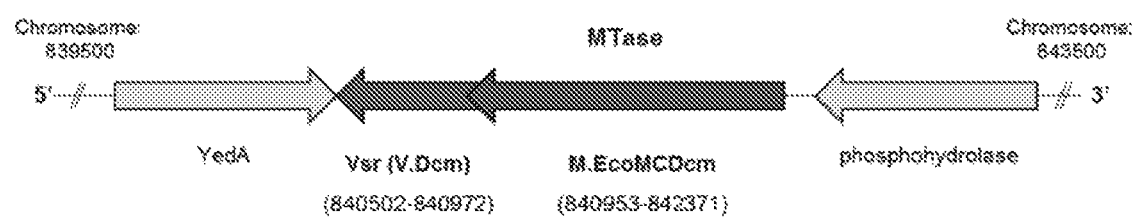
E. coli MC (EcoMC) HsdRMS system
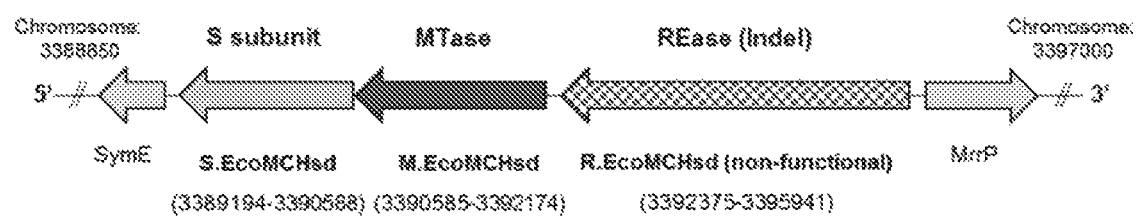
E. coli MC (EcoMC) Dam system
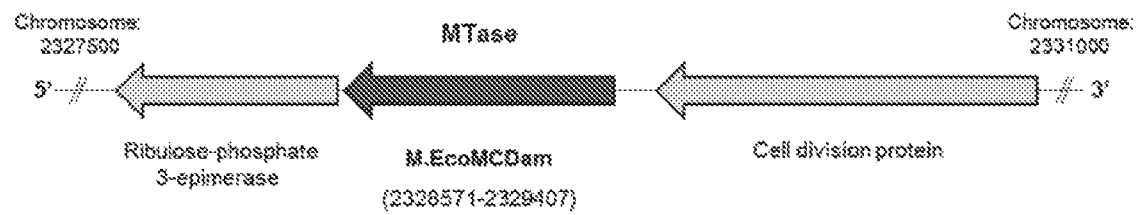
FIG. 5C

FIG.8D

Motif Modifications of *Escherichia coli* JMC2 producing strain (Dcm-/Hsd-/Dam+)

| No | R-M Type | Motif [a] | Modified Position | Modification Type | # of Motifs in Genome [b] | # of Motifs Detected | % Motifs Detected | Partner Motif |
|---|---|---|---|---|---|---|---|---|
| A | II | GATC | 2 | m6A | 38844 | 38,548 | 99.23% | GA*T*C | a The modified base within each motif is bolded while the modified base in the complementary strand is italicized.
b The total number includes motifs occurring on the "+" and "−" strands.

FIG.8E

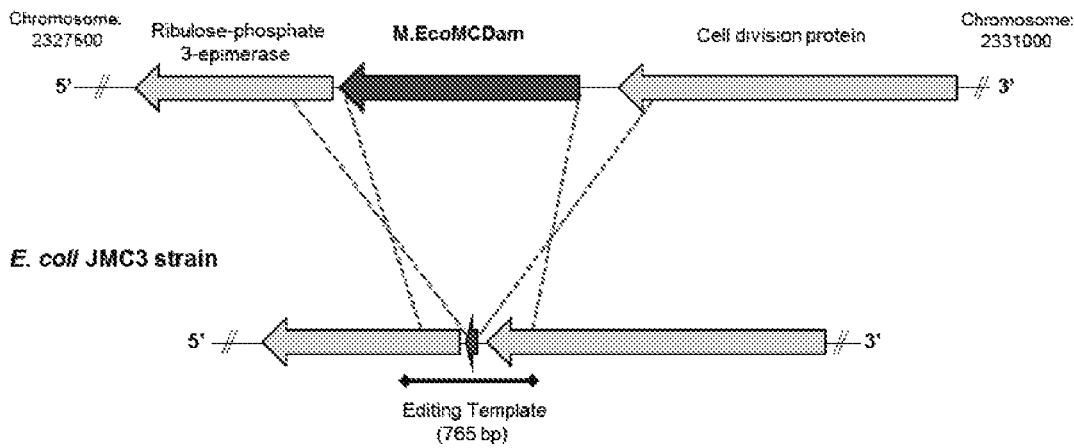

FIG.8F

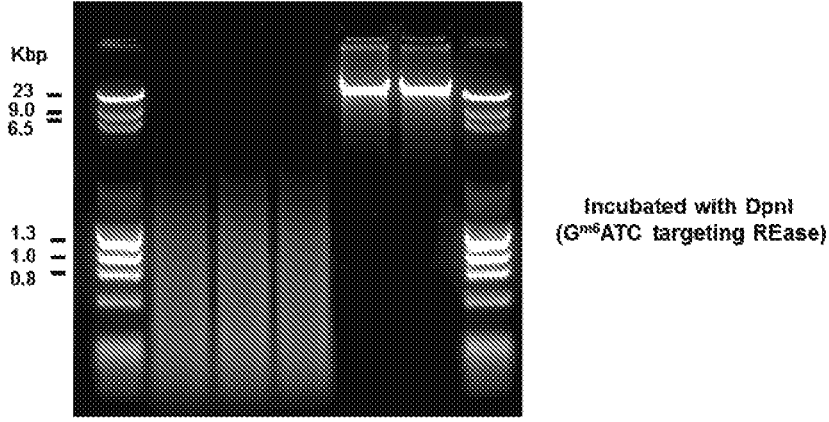

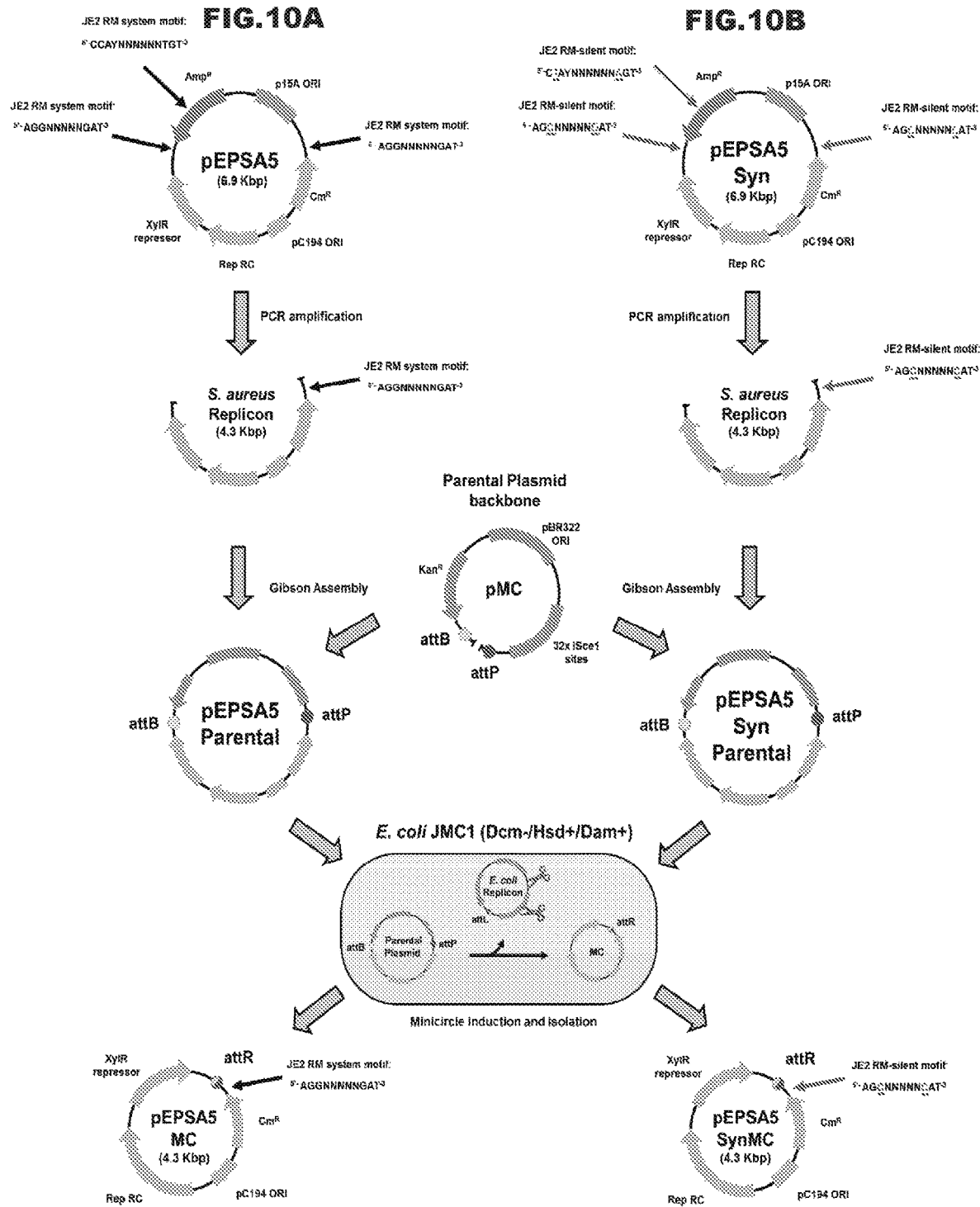

PAM sites in *E. coli HsdM* gene

5'
ATGAACAATA|<u>ACGATCTGGTCGCGAAGCTG</u>|*T*GGAAGCTG|<u>TGCGACAACCTGCGCGA*T*</u>
<u>G*G*</u>|CGGCGTTTCCTATCAAAACTACGTCAATGAACTCGCCTCGCTGCTGTTTTTGAAAAT
GTG|<u>TAAAGAGACCGGTCAGGAAG</u>|CGGAATACCTGCC*GG*AAGGTTACCGC*T*GGGATGA
CCTGAAATCCCGCATCGGCCAGGAGCAGTTGCAGTTCTACCGAAAAATGCTCGTGCAT
T*T*AGGCGAAGATGACAAAAAGC*T*GGTACA*GG*CAGTTTTCATAATGTTAGTACCACCAT
CACCGAGCCGAAACAAATAACCGCAC*T*GGTCAGCAATA*TGG*ATTCGC*T*GGAC*T*GGTAC
AACGGCGCGCACGGTAAGTCGCGCGATGACTTCGGCGATATGTACGAA*GGG*CTGTTG
CAGAAGAACGCGAATGAAACCAAGTC*T*GGTGCA*GG*CCAGTACTTCACCCCGCGTCCGC
TGATTAAACCATTATTCATCTGCT|<u>GAAACCGCAGCCGCGTGAAG</u>|*TGG*TGCA*GG*ACCC
*GG*C*GG*CA*GG*TACG*GCGGG*CTTTTGATTGAAGCCGACCGCTATGTTAAGTCGCAAACC
AATGATC*T*GGACGACCTTGA*TGG*CGACACGCA*GG*ATTTCCAGATCCACCGCGTTTA
TCGGCCTCGAAC*T*GGTGCCC*GG*CACCCGTCGTC*T*GGCACTGATGAACTGCCTGCTGC
ACGATATTGAA*GG*CAACCTCGACCAC*GGCGG*CGCAATCCGTC*T*GGGCAACACTC*T*GG
GTAGCGACGGTGAAAACCTGCCGAA*GG*CGCATATTGTCGCCACTAACCCGCCGTT*T*GG
CAGCGCCGCA*GG*CACCAACATTACCCGCACCTTTGTTCACCCGACCAGCAACAAACAG
TTGTGCTTTATGCAGCATATTATCGAAACGCTGCATCCC*GGCGG*TCG*T*GC*GGCGGTGG*
*TGG*TGCC*GG*ATAACGTGCTGTTTGAAG*GCGG*CAAA*GG*CACCGACATTCGTCGTGACCT
GA*TGG*ATAAGTGTCATCTGCACACCATTCTGCGTCTGCCGACCGGTATTTTTTACGCTC
A*GGG*CGTGAAGACCAACGTGCTGTTCTTTACCAAA*GGG*ACG*GTGG*CGAACCCGAATCA
GGATAAGAACTGTACCGATGATGTG*T*GGGTGTATGACCTGCGTACCAATATGCCGAGTT
TCGGCAAGCGCACACCGTTTACCGACGAGCATTTGCAGCCGTTTGAGCGCGTGTA*TGG*
CGAAGACCCGCACGGTTTAAGCCCGCGCACTGAAGGTGAA*TGG*AGTTTTAACGCCGAA
GAGACGGAAGTTGCCGACAGCGAAGAGAACAAAAACACCGACCAGCATCTTGCTACCA
GCCGC*T*GGCGCAAGTTCAGCCGTGA*T*GGATCCGCACCGCAAATCCGATTCGC*T*GG
ATATCTCC*T*GGCTGAAAGATAAGACAGTATTGATGCCGACAGCCTGCCGGAGCCGGA
TGTATTAGCGGCAGAAGCGA*TGGG*CGAAC*T*GGTACA*GG*CGCTGTCTGAAC*T*GGATGC
GCTGATGCGTGAAC*TGGGGG*CGAGCGA*T*GA*GG*CCGATTTGCAGCGTCAGTTGC*T*GGA
AGAAGCGTT*T*GG*T*G*GGG*TGAAGGAATGA (SEQ ID NO:83)
3'

*NGG* – PAM sites are indicated by italic bases
*GNGG* – PAM sites w/ increased efficiency are indicated by italic bases and a bold guanine (G).
|NNNNNNNNNNNNNNNNNNNN| – gRNA protospacer target sequences are indicated by double underlines. These sequences may be used as the gRNA sequence to guide CRISPR-mediated recombineering.

Protospacer options:
1. 5' <u>ACGATCTGGTCGCGAAGCTG</u>*     (SEQ ID NO:84)
2. 5' TGCGACAACCTGCGCGATGG       (SEQ ID NO:85)
3. 5' TAAAGAGACCGGTCAGGAAG       (SEQ ID NO:86)
4. 5' GAAACCGCAGCCGCGTGAAG       (SEQ ID NO:87)
* This sequence is used as the gRNA sequence to guide CRISPR-mediated recombineering in the Examples

*FIG. 12*

PAM sites in *E. coli dcm* gene

5'
ATGC*AGG*AAAATATATCAGTAACCGATTCATACAGCACC*GGG*AATGCCGCACA*GG*CAAT
GC*TGG*AGAAACTGCTGCAAAT|TTATGATGTTAAAAC*G**TTGG*|TGGCGCAGCTTAA*TGG*T
GT|AGGTGAGAATCACTGGAGCG|CGGCAATTTTAAAACGTGCGC*TGG*CGAATGACTCG
GCA*TGG*CACCGTTTAAGTGAGAAAGAGTTCGCCCATCTGCAAACGTTATTACCCAAACC
ACCGGCACATCATCCGCATTATGCGTTTCGCTTTATC|GATCTATTCGCCGGAAT*TGG*|C
GGCATCCGTC*GC*GGTTTTGAATCGA*TTGG*CGGACAGTGCGTGTTACCAGCGAA*TGG*A
ACAAACAT*GC*GGTACGCACTTATAAAGCCAACCATTATTGCGATC*CGG*CGACGCATCAT
TTTAATGAAGATATCCGCGACATCACCCTCAGCCATAAAGAAGGCGTGAGTGAT*GAGG*
CG*GCGG*CGGAACATATTCGTCAACACATTCCTGAACACGATGTTTTAC*TGG*CCGGTTTC
CCTTGTCAGCCATTTTCGC*TGGCTGG*CGTATCGAAAAAGAACTCGCTC*GGG*C*GGG*CGC
ACGGTTTTGCCTGCGATACCCAG*GG*CACGCTGTTTTTGATG*TGG*TACGCATTATCGAC
GCGCGTCGTC*CGG*CGATGTTTGTGCTCGAAAACGTCAAAAACCTGAAAAGTCACGACC
A*GGG*TAAAACGTTCCGCATCATCATGCAGACGC*TGG*ACGAAC*TGG*GCTATGAC*TGG*C
TGATGCAGAAGATAA*TGG*GCCAGACGATCCGAAAATCATCGACGGCAAACATTTTCTGC
CGCAGCACCGTGAACGCATCGTGC*TGGTGG*GTTTTCGTCGCGATCTGAATCTGAAAGC
CGATTTTACCCTGCGTGATATCAGCGAATGTTTCCCTGCGCAGCGAGTGACGC*TGG*CG
CAGCTGT*TGG*ACCCGA*TGG*TC*GAGG*CGAAATATATCCTGACGCCGGTGCT*GTGG*AAGT
ACCTCTATCGATATGCGAAAAAACATCA*GG*CGC*GC*GGTAACGGCTTCG*GTT*A*TGG*AAT
GGTTTATCCGAACAATCCGCAAAGCGTCACGCGTACGCTGTCTGCGCGTTATTACAAAG
A*TGGCGC*GGAAATTTTAATCGATC*GCGGC*T*GGG*ATA*TGG*CCAC*GGG*TGAGAAAGACTT
TGACGATCCGCTGAATCAGCAACATCGTCCACGTCGGTTAACGCCTC*GGG*AATGCGCG
CGCTTAA*TGG*GTTTTGAAGCGCGGGAGAAGCGAAATTCCGTATTCCGGTTTCGGACA
CTCAGGCCTATCGCCAGTTCGGTAACTC*GGT*GGTCGTGCCGGTCTTTGCC*GC*GGT*GG*
CAAAACTGCTTGAGCCAAAAATCAAAC*AGGCGGT*GGCGTTGCGTCAGCAA*GAGG*CACA
ACA*TGG*CCGACGTTCACGATAA (SEQ ID NO:88)
3'

*NGG* – PAM sites are indicated by italic bases
*GNGG* – PAM sites w/ increased efficiency are indicated by italic bases and a bold guanine (G)
|NNNNNNNNNNNNNNNNNNNNG| – gRNA protospacer target sequences are indicated by double underlines. These sequences may be used as the gRNA sequence to guide CRISPR-mediated recombineering.

Protospacer options:
1. 5' AGGTGAGAATCACTGGAGCG*    (SEQ ID NO:89)
2. 5' TTATGATGTTAAAACGTTGG     (SEQ ID NO:90)
3. 5' GATCTATTCGCCGGAATTGG     (SEQ ID NO:91)
* This sequence is used as the gRNA sequence to guide CRISPR-mediated recombineering in the Examples

*FIG. 13*

PAM sites in *E. coli dam* gene

5'
ATGAAGA|AAAATCGCGCTTTTTTGAAG|*T*GGGCAGGGGGCAAGTATC|CCCTGCTTGAT
GATATTAAA|CGGCATTTGCCCAAGGGCGAATGTC*T*GGTTGAGCCTTTTGTA*G*GTGCCG
GGTCGGTGTTTCTCAACACCGACTTTTCTCGTTATATCCTTGCCGATATCAATAGCGAC
CTGATCAGTCTCTATAACATTGTGAAGATGCGTACTGATGAGTACGTACAGGCCGCACG
CGAGCTGTTTGT|TCCCGAAACAAATTGCGCCG|AGGTTTACTATCAGTTCCGCGAAGAG
TTCAACAAAG|CCAGGATCCGTTCCGTCGGG|CGGTACTGTTTTTATATTTGAACCGCT
ACGGTTACAACGGCCTGTGTCGTTACAATCTGC*G*CGGTGAGTTTAACGTGCCGTTCGG
CCGCTACAAAAAACCCTATTTCCCGGAAGCAGAGTTGTATCACTTCGCTGAAAAAGCGC
AGAATGCCTTTTCTATTGTGAGTCTTACGCCGATAGCA*T*GGCGCGCGCAGATGATGCA
TCCGTCGTCTATTGCGATCCGCCTTATGCACCGCTGTCTGCGACCGCCAACTTTACGG
CGTATCACACAAACAGTTTTACGCTTGAACAACAAGCGCATC*T*GGCGGAGATCGCCGA
AGGTC*T*GGTTGAGCGCCATATTCCAGTGCTGATCTCCAATCACGATACGATGTTAACGC
GTGAGTGGTATCAGCGCGCAAAATTGCATGTCGTCAAAGTTCGACGCAGTATAAGCAG
CAACGGCGGCACACGTAAAAAG*G*TGGACGAACTGC*T*GGCTTTGTACAAACCAGGAGTC
GTTTCACCCGCGAAAAATAA (SEQ ID NO:92)
3'

*NGG* — PAM sites are indicated by italic bases
*GNGG* — PAM sites w/ increased efficiency are indicated by italic bases and a bold guanine (G)
|NNNNNNNNNNNNNNNNNNNNG| — gRNA protospacer target sequences are indicated by double underlines. These sequences may be used as the gRNA sequence to guide CRISPR-mediated recombineering.

Protospacer options:
1. 5' CCCTGCTTGATGATATTAAA*   (SEQ ID NO:93)
2. 5' AAAATCGCGCTTTTTTGAAG    (SEQ ID NO:94)
3. 5' TCCCGAAACAAATTGCGCCG    (SEQ ID NO:95)
4. 5' CCAGGATCCGTTCCGTCGGG    (SEQ ID NO:96)
* This sequence is used as the gRNA sequence to guide CRISPR-mediated recombineering in the Examples

*FIG. 14*

SEQUENCE LISTING

<160> NUMBER OF SEQ ID NOS: 109

<210> SEQ ID NO 1
<211> LENGTH: 13
<212> TYPE: DNA
<213> ORGANISM: Artificial Sequence
<220> FEATURE:
<223> OTHER INFORMATION: Recognition sequence
<220> FEATURE:
<221> NAME/KEY: misc_feature
<222> LOCATION: (1)...(13)
<223> OTHER INFORMATION: n = A,T,C or G

<400> SEQUENCE: 1
aacnnnnnng tgc                                                          13

<210> SEQ ID NO 2
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 4
<223> OTHER INFORMATION: n = C or T
<220> FEATURE:
<221> NAME/KEY: misc_feature
<222> LOCATION: (5)...(10)
<223> OTHER INFORMATION: n = A, C, T or G

<400> SEQUENCE: 2
ccannnnnnn tgt                                                          13

<210> SEQ ID NO 3
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 4
<223> OTHER INFORMATION: n = A or G
<220> FEATURE:
<221> NAME/KEY: misc_feature
<222> LOCATION: (5)...(10)
<223> OTHER INFORMATION: n = A, C, T or G

<400> SEQUENCE: 3
ggtnnnnnnn aca                                                          13

<210> SEQ ID NO 4
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)...(8)
<223> OTHER INFORMATION: n = A, C, T or G

<400> SEQUENCE: 4
aggnnnnnga t                                                            11

<210> SEQ ID NO 5
<211> LENGTH: 9
<212> TYPE: PRT
<213> ORGANISM: Artificial Sequence
<220> FEATURE:
<223> OTHER INFORMATION: Synthetic sequence

<400> SEQUENCE: 5

Arg Ile Pro Thr Gln Pro Val Ala Met
1               5

<210> SEQ ID NO 6
<211> LENGTH: 13
<212> TYPE: DNA
<213> ORGANISM: Artificial Sequence
<220> FEATURE:
<223> OTHER INFORMATION: Synthetic sequence Motif
<220> FEATURE:

```
<221> NAME/KEY: misc_feature
<222> LOCATION: (4)...(9)
<223> OTHER INFORMATION: n = A, C, T, or G

<400> SEQUENCE: 6
acannnnnnr tgg                                                          13

<210> SEQ ID NO 7
<211> LENGTH: 11
<212> TYPE: DNA
<213> ORGANISM: Artificial Sequence
<220> FEATURE:
<223> OTHER INFORMATION: Synthetic sequence Motif
<220> FEATURE:
<221> NAME/KEY: misc_feature
<222> LOCATION: (4)...(80)
<223> OTHER INFORMATION: n = A, C, T or G

<400> SEQUENCE: 7
atcnnnnncc t                                                            11

<210> SEQ ID NO 8
<211> LENGTH: 27
<212> TYPE: DNA
<213> ORGANISM: Artificial Sequence
<220> FEATURE:
<223> OTHER INFORMATION: Forward primer sequence

<400> SEQUENCE: 8
ggttagttag gtgaaatttg tgtatat                                           27

<210> SEQ ID NO 9
<211> LENGTH: 23
<212> TYPE: DNA
<213> ORGANISM: Artificial Sequence
<220> FEATURE:
<223> OTHER INFORMATION: Reverse primer sequence

<400> SEQUENCE: 9
aataacaaca aaaaccaca acc                                                23

<210> SEQ ID NO 10
<211> LENGTH: 24
<212> TYPE: DNA
<213> ORGANISM: Artificial Sequence
<220> FEATURE:
<223> OTHER INFORMATION: Forward primer sequence

<400> SEQUENCE: 10
atggatttgg tttttggtta gatt                                              24

<210> SEQ ID NO 11
<211> LENGTH: 25
<212> TYPE: DNA
<213> ORGANISM: Artificial Sequence
<220> FEATURE:
<223> OTHER INFORMATION: Reverse primer sequence

<400> SEQUENCE: 11
caacccttcc aacactttat tcaat                                             25

<210> SEQ ID NO 12
<211> LENGTH: 26
<212> TYPE: DNA
<213> ORGANISM: Artificial Sequence
<220> FEATURE:
<223> OTHER INFORMATION: Forward primer sequence
```

<400> SEQUENCE: 12
tgggttaata ggaggaatta attatg                                          26

<210> SEQ ID NO 13
<211> LENGTH: 25
<212> TYPE: DNA
<213> ORGANISM: Artificial Sequence
<220> FEATURE:
<223> OTHER INFORMATION: Reverse primer sequence

<400> SEQUENCE: 13
cataaaccaa tataccaaaa acatc                                           25

<210> SEQ ID NO 14
<211> LENGTH: 36
<212> TYPE: DNA
<213> ORGANISM: Artificial Sequence
<220> FEATURE:
<223> OTHER INFORMATION: Forward primer sequence

<400> SEQUENCE: 14
taaataatgg atattaatac tgaaactgag atcaag                               36

<210> SEQ ID NO 15
<211> LENGTH: 37
<212> TYPE: DNA
<213> ORGANISM: Artificial Sequence
<220> FEATURE:
<223> OTHER INFORMATION: Reverse primer sequence

<400> SEQUENCE: 15
gtcttaacgc tcatgtctag attaagaaat aatcttc                              37

<210> SEQ ID NO 16
<211> LENGTH: 41
<212> TYPE: DNA
<213> ORGANISM: Artificial Sequence
<220> FEATURE:
<223> OTHER INFORMATION: Forward primer sequence

<400> SEQUENCE: 16
taatctagac atgagcgtta agacccactt tcacatttaa g                         41

<210> SEQ ID NO 17
<211> LENGTH: 39
<212> TYPE: DNA
<213> ORGANISM: Artificial Sequence
<220> FEATURE:
<223> OTHER INFORMATION: Reverse primer sequence

<400> SEQUENCE: 17
tttcagtatt aatatccatt atttacctcc ttaggtcac                            39

<210> SEQ ID NO 18
<211> LENGTH: 27
<212> TYPE: DNA
<213> ORGANISM: Artificial Sequence
<220> FEATURE:
<223> OTHER INFORMATION: Forward primer sequence

<400> SEQUENCE: 18
caattgatcg taaacgatat acgtcta                                         27

<210> SEQ ID NO 19

```
<211> LENGTH: 25
<212> TYPE: DNA
<213> ORGANISM: Artificial Sequence
<220> FEATURE:
<223> OTHER INFORMATION: Reverse primer sequence

<400> SEQUENCE: 19
ctcaagacga tcctgaatgt aataa                                              25

<210> SEQ ID NO 20
<211> LENGTH: 24
<212> TYPE: DNA
<213> ORGANISM: Artificial Sequence
<220> FEATURE:
<223> OTHER INFORMATION: Forward primer sequence

<400> SEQUENCE: 20
tcggtaagcg cttcatccgt cagc                                               24

<210> SEQ ID NO 21
<211> LENGTH: 30
<212> TYPE: DNA
<213> ORGANISM: Artificial Sequence
<220> FEATURE:
<223> OTHER INFORMATION: Reverse primer sequence

<400> SEQUENCE: 21
gaaatctatg catggccgac gttcacgata                                         30

<210> SEQ ID NO 22
<211> LENGTH: 30
<212> TYPE: DNA
<213> ORGANISM: Artificial Sequence
<220> FEATURE:
<223> OTHER INFORMATION: Forward primer sequence

<400> SEQUENCE: 22
gtcggccatg catagatttc accggccatc                                         30

<210> SEQ ID NO 23
<211> LENGTH: 22
<212> TYPE: DNA
<213> ORGANISM: Artificial Sequence
<220> FEATURE:
<223> OTHER INFORMATION: Reverse primer sequence

<400> SEQUENCE: 23
tgtccaggat gcggatcggc tg                                                 22

<210> SEQ ID NO 24
<211> LENGTH: 26
<212> TYPE: DNA
<213> ORGANISM: Artificial Sequence
<220> FEATURE:
<223> OTHER INFORMATION: Forward primer sequence

<400> SEQUENCE: 24
gaagatctag atctagatag taaaac                                             26

<210> SEQ ID NO 25
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 25
```
ggcgtaatca tggtcatagc                                              20

<210> SEQ ID NO 26
<211> LENGTH: 24
<212> TYPE: DNA
<213> ORGANISM: Artificial Sequence
<220> FEATURE:
<223> OTHER INFORMATION: Forward primer sequence

<400> SEQUENCE: 26
tcggtaagcg cttcatccgt cagc                                         24

<210> SEQ ID NO 27
<211> LENGTH: 30
<212> TYPE: DNA
<213> ORGANISM: Artificial Sequence
<220> FEATURE:
<223> OTHER INFORMATION: Reverse primer sequence

<400> SEQUENCE: 27
gaaatctatg catggccgac gttcacgata                                   30

<210> SEQ ID NO 28
<211> LENGTH: 34
<212> TYPE: DNA
<213> ORGANISM: Artificial Sequence
<220> FEATURE:
<223> OTHER INFORMATION: Forward primer sequence

<400> SEQUENCE: 28
ttacgcctgg ttgggcggtg aggacaatac agcc                              34

<210> SEQ ID NO 29
<211> LENGTH: 40
<212> TYPE: DNA
<213> ORGANISM: Artificial Sequence
<220> FEATURE:
<223> OTHER INFORMATION: Reverse primer sequence

<400> SEQUENCE: 29
ctcgttcacc cacgccaatc ataacccaca taaatatatt                        40

<210> SEQ ID NO 30
<211> LENGTH: 37
<212> TYPE: DNA
<213> ORGANISM: Artificial Sequence
<220> FEATURE:
<223> OTHER INFORMATION: Forward primer sequence

<400> SEQUENCE: 30
tatgattggc gtgggtgaac gagcgcagcc aacgcag                           37

<210> SEQ ID NO 31
<211> LENGTH: 34
<212> TYPE: DNA
<213> ORGANISM: Artificial Sequence
<220> FEATURE:
<223> OTHER INFORMATION: Reverse primer sequence

<400> SEQUENCE: 31
tactatctag gatctcaccc gtaaagggct ggtc                              34

<210> SEQ ID NO 32
<211> LENGTH: 36
<212> TYPE: DNA

```
<213> ORGANISM: Artificial Sequence
<220> FEATURE:
<223> OTHER INFORMATION: Forward primer sequence

<400> SEQUENCE: 32
gggtgagatc ctagatagta aaacggacat cactcc                               36

<210> SEQ ID NO 33
<211> LENGTH: 35
<212> TYPE: DNA
<213> ORGANISM: Artificial Sequence
<220> FEATURE:
<223> OTHER INFORMATION: Reverse primer sequence

<400> SEQUENCE: 33
cccaaccagg cgtaatcatg gtcatagctg tttcc                                35

<210> SEQ ID NO 34
<211> LENGTH: 23
<212> TYPE: DNA
<213> ORGANISM: Artificial Sequence
<220> FEATURE:
<223> OTHER INFORMATION: Forward primer sequence

<400> SEQUENCE: 34
tggttgggcg gtgaggacaa tac                                             23

<210> SEQ ID NO 35
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 35
gatctcaccc gtaagggct ggtc                                             24

<210> SEQ ID NO 36
<211> LENGTH: 35
<212> TYPE: DNA
<213> ORGANISM: Artificial Sequence
<220> FEATURE:
<223> OTHER INFORMATION: Forward primer sequence

<400> SEQUENCE: 36
tgattacgcc tttcgccaat gttgttcacc ttcac                                35

<210> SEQ ID NO 37
<211> LENGTH: 39
<212> TYPE: DNA
<213> ORGANISM: Artificial Sequence
<220> FEATURE:
<223> OTHER INFORMATION: Reverse primer sequence

<400> SEQUENCE: 37
agtcagcatg gtttcacccg cgaaaaaata attctcaag                            39

<210> SEQ ID NO 38
<211> LENGTH: 38
<212> TYPE: DNA
<213> ORGANISM: Artificial Sequence
<220> FEATURE:
<223> OTHER INFORMATION: Forward primer sequence

<400> SEQUENCE: 38
gggtgaaacc atgctgacta actaattaca ccttctcc                             38
```

<210> SEQ ID NO 39
<211> LENGTH: 37
<212> TYPE: DNA
<213> ORGANISM: Artificial Sequence
<220> FEATURE:
<223> OTHER INFORMATION: Reverse primer sequence

<400> SEQUENCE: 39
ctagatcttc aaaaaccgca agcaaccgtg aaaacgg                    37

<210> SEQ ID NO 40
<211> LENGTH: 36
<212> TYPE: DNA
<213> ORGANISM: Artificial Sequence
<220> FEATURE:
<223> OTHER INFORMATION: Forward primer sequence

<400> SEQUENCE: 40
tgcggttttt gaagatctag atctagatag taaaac                     36

<210> SEQ ID NO 41
<211> LENGTH: 32
<212> TYPE: DNA
<213> ORGANISM: Artificial Sequence
<220> FEATURE:
<223> OTHER INFORMATION: Reverse primer sequence

<400> SEQUENCE: 41
attggcgaaa ggcgtaatca tggtcatagc tg                         32

<210> SEQ ID NO 42
<211> LENGTH: 23
<212> TYPE: DNA
<213> ORGANISM: Artificial Sequence
<220> FEATURE:
<223> OTHER INFORMATION: Forward primer sequence

<400> SEQUENCE: 42
ttctttaatc agttgcagcg tgc                                   23

<210> SEQ ID NO 43
<211> LENGTH: 23
<212> TYPE: DNA
<213> ORGANISM: Artificial Sequence
<220> FEATURE:
<223> OTHER INFORMATION: Reverse primer sequence

<400> SEQUENCE: 43
aagaccgcag gtaatgttgg ttc                                   23

<210> SEQ ID NO 44
<211> LENGTH: 40
<212> TYPE: DNA
<213> ORGANISM: Artificial Sequence
<220> FEATURE:
<223> OTHER INFORMATION: Forward primer sequence

<400> SEQUENCE: 44
cactggagcc gttttagagc tagaaatagc aagttaaaat                 40

<210> SEQ ID NO 45
<211> LENGTH: 40
<212> TYPE: DNA
<213> ORGANISM: Artificial Sequence
<220> FEATURE:

<223> OTHER INFORMATION: Reverse primer sequence

<400> SEQUENCE: 45
attctcacct actagtatta tacctaggac tgagctagct    40

<210> SEQ ID NO 46
<211> LENGTH: 40
<212> TYPE: DNA
<213> ORGANISM: Artificial Sequence
<220> FEATURE:
<223> OTHER INFORMATION: Forward primer sequence

<400> SEQUENCE: 46
agtgatgagg gttttagagc tagaaatagc aagttaaaat    40

<210> SEQ ID NO 47
<211> LENGTH: 40
<212> TYPE: DNA
<213> ORGANISM: Artificial Sequence
<220> FEATURE:
<223> OTHER INFORMATION: Reverse primer sequence

<400> SEQUENCE: 47
cacgccttct actagtatta tacctaggac tgagctagct    40

<210> SEQ ID NO 48
<211> LENGTH: 40
<212> TYPE: DNA
<213> ORGANISM: Artificial Sequence
<220> FEATURE:
<223> OTHER INFORMATION: Forward primer sequence

<400> SEQUENCE: 48
cgcgaagctg gttttagagc tagaaatagc aagttaaaat    40

<210> SEQ ID NO 49
<211> LENGTH: 40
<212> TYPE: DNA
<213> ORGANISM: Artificial Sequence
<220> FEATURE:
<223> OTHER INFORMATION: Reverse primer sequence

<400> SEQUENCE: 49
accagatcgt actagtatta tacctaggac tgagctagct    40

<210> SEQ ID NO 50
<211> LENGTH: 40
<212> TYPE: DNA
<213> ORGANISM: Artificial Sequence
<220> FEATURE:
<223> OTHER INFORMATION: Forward primer sequence

<400> SEQUENCE: 50
attgccggag gttttagagc tagaaatagc aagttaaaat    40

<210> SEQ ID NO 51
<211> LENGTH: 40
<212> TYPE: DNA
<213> ORGANISM: Artificial Sequence
<220> FEATURE:
<223> OTHER INFORMATION: Reverse primer sequence

<400> SEQUENCE: 51
ttccccgcac actagtatta tacctaggac tgagctagct    40

```
<210> SEQ ID NO 52
<211> LENGTH: 40
<212> TYPE: DNA
<213> ORGANISM: Artificial Sequence
<220> FEATURE:
<223> OTHER INFORMATION: Forward primer sequence

<400> SEQUENCE: 52 tttttttgaag gttttagagc tagaaatagc aagttaaaat                              40

<210> SEQ ID NO 53
<211> LENGTH: 40
<212> TYPE: DNA
<213> ORGANISM: Artificial Sequence
<220> FEATURE:
<223> OTHER INFORMATION: Reverse primer sequence

<400> SEQUENCE: 53
gcgcgatttt actagtatta tacctaggac tgagctagct                              40

<210> SEQ ID NO 54
<211> LENGTH: 40
<212> TYPE: DNA
<213> ORGANISM: Artificial Sequence
<220> FEATURE:
<223> OTHER INFORMATION: Forward primer sequence

<400> SEQUENCE: 54
tgatattaaa gttttagagc tagaaatagc aagttaaaat                              40

<210> SEQ ID NO 55
<211> LENGTH: 40
<212> TYPE: DNA
<213> ORGANISM: Artificial Sequence
<220> FEATURE:
<223> OTHER INFORMATION: Reverse primer sequence

<400> SEQUENCE: 55
tcaagcaggg actagtatta tacctaggac tgagctagct                              40

<210> SEQ ID NO 56
<211> LENGTH: 22
<212> TYPE: DNA
<213> ORGANISM: Artificial Sequence
<220> FEATURE:
<223> OTHER INFORMATION: Forward primer sequence

<400> SEQUENCE: 56
tgctcacatg ttctttcctg cg                                                 22

<210> SEQ ID NO 57
<211> LENGTH: 21
<212> TYPE: DNA
<213> ORGANISM: Artificial Sequence
<220> FEATURE:
<223> OTHER INFORMATION: Reverse primer sequence

<400> SEQUENCE: 57
tcatgacatt gcactccacc g                                                  21

<210> SEQ ID NO 58
<211> LENGTH: 27
<212> TYPE: DNA
<213> ORGANISM: Artificial Sequence
<220> FEATURE:
<223> OTHER INFORMATION: Forward primer sequence
```

<400> SEQUENCE: 58
aacctgcccc gttagttgaa gaaggtt                                              27

<210> SEQ ID NO 59
<211> LENGTH: 18
<212> TYPE: DNA
<213> ORGANISM: Artificial Sequence
<220> FEATURE:
<223> OTHER INFORMATION: Reverse primer sequence

<400> SEQUENCE: 59
gtcgacctgc agccaagc                                                       18

<210> SEQ ID NO 60
<211> LENGTH: 25
<212> TYPE: DNA
<213> ORGANISM: Artificial Sequence
<220> FEATURE:
<223> OTHER INFORMATION: Forward primer sequence

<400> SEQUENCE: 60
cggggcaggt tagtgacatt agaaa                                               25

<210> SEQ ID NO 61
<211> LENGTH: 22
<212> TYPE: DNA
<213> ORGANISM: Artificial Sequence
<220> FEATURE:
<223> OTHER INFORMATION: Reverse primer sequence

<400> SEQUENCE: 61
tgcaggtcga ctctagagga tc                                                  22

<210> SEQ ID NO 62
<211> LENGTH: 39
<212> TYPE: DNA
<213> ORGANISM: Artificial Sequence
<220> FEATURE:
<223> OTHER INFORMATION: Forward primer sequence

<400> SEQUENCE: 62
cgcgacaagc ttctgtaggt ttttaggcat aaaactata                                39

<210> SEQ ID NO 63
<211> LENGTH: 35
<212> TYPE: DNA
<213> ORGANISM: Artificial Sequence
<220> FEATURE:
<223> OTHER INFORMATION: Reverse primer sequence

<400> SEQUENCE: 63
ttggggtcga ctctagagga tccccgggta ccgag                                    35

<210> SEQ ID NO 64
<211> LENGTH: 40
<212> TYPE: DNA
<213> ORGANISM: Artificial Sequence
<220> FEATURE:
<223> OTHER INFORMATION: Forward primer sequence

<400> SEQUENCE: 64
ctagagtcga ccccaactgg ggtaaccttt gagttctctc                               40

<210> SEQ ID NO 65
<211> LENGTH: 28

```
<212> TYPE: DNA
<213> ORGANISM: Artificial Sequence
<220> FEATURE:
<223> OTHER INFORMATION: Reverse primer sequence

<400> SEQUENCE: 65
acagaagctt gtcgcgcccg gggagccc                                      28

<210> SEQ ID NO 66
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(11)
<223> OTHER INFORMATION: n = A,T,C or G

<400> SEQUENCE: 66
nnggatccnn n                                                        11

<210> SEQ ID NO 67
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(11)
<223> OTHER INFORMATION: n = A,T,C or G

<400> SEQUENCE: 67
cagnnnnntt g                                                        11

<210> SEQ ID NO 68
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(11)
<223> OTHER INFORMATION: n = A,T,C or G

<400> SEQUENCE: 68
nnctcgagnn n                                                        11

<210> SEQ ID NO 69
<211> LENGTH: 27
<212> TYPE: DNA
<213> ORGANISM: Artificial Sequence
<220> FEATURE:
<223> OTHER INFORMATION: Synthetic sequence

<400> SEQUENCE: 69
cggatcccca cgcagcctgt ttgcatg                                       27

<210> SEQ ID NO 70
<211> LENGTH: 27
<212> TYPE: DNA
<213> ORGANISM: Artificial Sequence
<220> FEATURE:
<223> OTHER INFORMATION: Synthetic sequence

<400> SEQUENCE: 70
```

```
cgcatacccca cgcaacctgt gtgcatg                                              27

<210> SEQ ID NO 71
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(11)
<223> OTHER INFORMATION: n = A,T,C or G

<400> SEQUENCE: 71
tccnnnnnct a                                                                 11

<210> SEQ ID NO 72
<211> LENGTH: 27
<212> TYPE: DNA
<213> ORGANISM: Escherichia coli

<400> SEQUENCE: 72
tcatcgatag gatgggatg agcggat                                                 27

<210> SEQ ID NO 73
<211> LENGTH: 27
<212> TYPE: DNA
<213> ORGANISM: Artificial Sequence
<220> FEATURE:
<223> OTHER INFORMATION: Synthetic sequence

<400> SEQUENCE: 73
tcatcgatac gatgggcatg agcggat                                                27

<210> SEQ ID NO 74
<211> LENGTH: 27
<212> TYPE: DNA
<213> ORGANISM: Escherichia coli

<400> SEQUENCE: 74
cgtgacacca cgatgcctgt agcaatg                                                27

<210> SEQ ID NO 75
<211> LENGTH: 27
<212> TYPE: DNA
<213> ORGANISM: Artificial Sequence
<220> FEATURE:
<223> OTHER INFORMATION: Synthetic sequence

<400> SEQUENCE: 75
cgtgacacta cgatgccagt agcaatg                                                27

<210> SEQ ID NO 76
<211> LENGTH: 27
<212> TYPE: DNA
<213> ORGANISM: Escherichia coli

<400> SEQUENCE: 76
gaaaaagaag gatatggatc tggagct                                                27

<210> SEQ ID NO 77
<211> LENGTH: 27
<212> TYPE: DNA
<213> ORGANISM: Artificial Sequence
<220> FEATURE:
<223> OTHER INFORMATION: Synthetic sequence
```

```
<400> SEQUENCE: 77
gaaaaagaag catatgcatc tggagct                                          27

<210> SEQ ID NO 78
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(13)
<223> OTHER INFORMATION: n = A,T,C or G

<400> SEQUENCE: 78
gcacnnnnnn gtt                                                         13

<210> SEQ ID NO 79
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(13)
<223> OTHER INFORMATION: n = A,T,C or G

<400> SEQUENCE: 79
aacnnnnnng tgc                                                         13

<210> SEQ ID NO 80
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(13)
<223> OTHER INFORMATION: n = A,T,C or G

<400> SEQUENCE: 80
ctaynnnnnn agt                                                         13

<210> SEQ ID NO 81
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(11)
<223> OTHER INFORMATION: n = A,T,C or G

<400> SEQUENCE: 81
agcnnnnnga t                                                           11

<210> SEQ ID NO 82
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(11)
```

<223> OTHER INFORMATION: n = A,T,C or G

<400> SEQUENCE: 82
agcnnnnnca t                                                                11

<210> SEQ ID NO 83
<211> LENGTH: 1590
<212> TYPE: DNA
<213> ORGANISM: Escherichia coli

<400> SEQUENCE: 83

```
atgaacaata acgatctggt cgcgaagctg tggaagctgt gcgacaacct gcgcgatggc    60
ggcgtttcct atcaaaacta cgtcaatgaa ctcgcctcgc tgctgttttt gaaaatgtgt   120
aaagagaccg gtcaggaagc ggaatacctg ccggaaggtt accgctggga tgacctgaaa   180
tcccgcatcg gccaggagca gttgcagttc taccgaaaaa tgctcgtgca tttaggcgaa   240
gatgacaaaa agctggtaca ggcagttttt cataatgtta gtaccaccat caccgagccg   300
aaacaaataa ccgcactggt cagcaatatg gattcgctgg actggtacaa cggcgcgcac   360
ggtaagtcgc gcgatgactt cggcgatatg tacgaagggc tgttgcagaa aacgcgaat   420
gaaaccaagt ctggtgcagg ccagtacttc accccgcgtc cgctgattaa aaccattatt   480
catctgctga aaccgcagcc gcgtgaagtg gtgcaggacc cggcggcagg tacggcgggc   540
tttttgattg aagccgaccg ctatgttaag tcgcaaacca atgatctgga cgaccttgat   600
ggcgacacgc aggatttcca gatccaccgc gcgtttatcg gcctcgaact ggtgcccggc   660
acccgtcgtc tggcactgat gaactgcctg ctgcacgata ttgaaggcaa cctcgaccac   720
ggcggcgcaa tccgtctggg caacactctg ggtagcgacg gtgaaaacct gccgaaggcg   780
catattgtcg ccactaaccc gccgtttggc agccgcgcag gcaccaacat acccgcacc   840
tttgttcacc cgaccagcaa caaacagttg tgctttatgc agcatattat cgaaacgctg   900
catcccggcg tcgtgcggc ggtggtggtg ccggataacg tgctgtttga aggcggcaaa   960
ggcaccgaca ttcgtcgtga cctgatggat aagtgtcatc tgcacaccat tctgcgtctg  1020
ccgaccggta tttttttacgc tcagggcgtg aagaccaacg tgctgttctt taccaaaggg  1080
acggtggcga acccgaatca ggataagaac tgtaccgatg atgtgtgggt gtatgacctg  1140
cgtaccaata tgccgagttt cggcaagcgc acaccgttta cgacgagca tttgcagccg  1200
tttgagcgcg tgtatggcga agacccgcac ggtttaagcc cgcgcactga aggtgaatgg  1260
agttttaacg ccgaagagac ggaagttgcc gacagcgaag agaacaaaaa caccgaccag  1320
catcttgcta ccagccgctg gcgcaagttc agccgtgagt ggatccgcac cgcaaaatcc  1380
gattcgctgg atatctcctg gctgaaagat aaagacagta ttgatgccga cagcctgccg  1440
gagccggatg tattagcggc agaagcgatg ggcgaactgg tacaggcgct gtctgaactg  1500
gatgcgctga tgcgtgaact gggggcgagc gatgaggccg atttgcagcg tcagttgctg  1560
gaagaagcgt ttggtggggt gaaggaatga                                   1590
```

<210> SEQ ID NO 84
<211> LENGTH: 20
<212> TYPE: DNA
<213> ORGANISM: Escherichia coli

<400> SEQUENCE: 84
acgatctggt cgcgaagctg                                                       20

```
<210> SEQ ID NO 85
<211> LENGTH: 20
<212> TYPE: DNA
<213> ORGANISM: Escherichia coli

<400> SEQUENCE: 85
tgcgacaacc tgcgcgatgg                                              20

<210> SEQ ID NO 86
<211> LENGTH: 20
<212> TYPE: DNA
<213> ORGANISM: Escherichia coli

<400> SEQUENCE: 86
taaagagacc ggtcaggaag                                              20

<210> SEQ ID NO 87
<211> LENGTH: 20
<212> TYPE: DNA
<213> ORGANISM: Escherichia coli

<400> SEQUENCE: 87
gaaaccgcag ccgcgtgaag                                              20

<210> SEQ ID NO 88
<211> LENGTH: 1419
<212> TYPE: DNA
<213> ORGANISM: Escherichia coli

<400> SEQUENCE: 88
atgcaggaaa atatatcagt aaccgattca tacagcaccg ggaatgccgc acaggcaatg    60
ctggagaaac tgctgcaaat ttatgatgtt aaaacgttgg tggcgcagct taatggtgta   120
ggtgagaatc actggagcgc ggcaatttta aaacgtgcgc tggcgaatga ctcggcatgg   180
caccgtttaa gtgagaaaga gttcgcccat ctgcaaacgt tattcccaa ccaccggca    240 catcatccgc attatgcgtt tcgctttatc gatctattcg ccggaattgg cggcatccgt   300
cgcggttttg aatcgattgg cggacagtgc gtgtttacca gcgaatggaa caaacatgcg   360
gtacgcactt ataaagccaa ccattattgc gatccggcga cgcatcattt taatgaagat   420
atccgcgaca tcacccctcag ccataaagaa ggcgtgagtg atgaggcggc ggcggaacat   480
attcgtcaac acattcctga cacgatgtt ttactgccg gtttcccttg tcagccattt    540
tcgctggctg gcgtatcgaa aaagaactcg ctcgggcggg cgcacggttt tgcctgcgat   600
acccagggca cgctgttttt tgatgtggta cgcattatcg acgcgcgtcg tccggcgatg   660
tttgtgctcg aaaacgtcaa aaacctgaaa agtcacgacc agggtaaaac gttccgcatc   720
atcatgcaga cgctggacga actgggctat gacgtggctg atgcagaaga taatgggcca   780
gacgatccga aaatcatcga cggcaaacat tttctgccgc agcaccgtga acgcatcgtg   840
ctggtgggtt tcgtcgcga tctgaatctg aaagccgatt ttaccctgcg tgatatcagc   900
gaatgtttcc ctgcgcagcg agtgacgctg gcgcagctgt tggacccgat ggtcgaggcg   960
aaatatatcc tgacgccggt gctgtggaag tacctctatc gatatgcgaa aaaacatcag  1020
gcgcgcggta acggcttcgg ttatggaatg gtttatccga caatccgca aagcgtcacg  1080 cgtacgctgt ctgcgcgtta ttacaaagat ggcgcggaaa ttttaatcga tcgcggctgg  1140
gatatggcca cgggtgagaa agactttgac gatccgctga atcagcaaca tcgtccacgt  1200
cggttaacgc ctcgggaatg cgcgcgctta atgggttttg aagcgccggg agaagcgaaa  1260
```

```
ttccgtattc cggtttcgga cactcaggcc tatcgccagt tcggtaactc ggtggtcgtg    1320
ccggtctttg ccgcggtggc aaaactgctt gagccaaaaa tcaaacaggc ggtggcgttg    1380
cgtcagcaag aggcacaaca tggccgacgt tcacgataa                           1419

<210> SEQ ID NO 89
<211> LENGTH: 20
<212> TYPE: DNA
<213> ORGANISM: Escherichia coli

<400> SEQUENCE: 89
aggtgagaat cactggagcg                                                  20

<210> SEQ ID NO 90
<211> LENGTH: 20
<212> TYPE: DNA
<213> ORGANISM: Escherichia coli

<400> SEQUENCE: 90
ttatgatgtt aaaacgttgg                                                  20

<210> SEQ ID NO 91
<211> LENGTH: 20
<212> TYPE: DNA
<213> ORGANISM: Escherichia coli

<400> SEQUENCE: 91
gatctattcg ccggaattgg                                                  20

<210> SEQ ID NO 92
<211> LENGTH: 837
<212> TYPE: DNA
<213> ORGANISM: Escherichia coli

<400> SEQUENCE: 92
atgaagaaaa atcgcgcttt tttgaagtgg gcaggggggca agtatcccct gcttgatgat     60
attaaacggc atttgcccaa gggcgaatgt ctggttgagc cttttgtagg tgccgggtcg    120
gtgtttctca acaccgactt ttctcgttat atccttgccg atatcaatag cgacctgatc    180
agtctctata acattgtgaa gatgcgtact gatgagtacg tacaggccgc acgcgagctg    240
tttgttcccg aaacaaattg cgccgaggtt tactatcagt tccgcgaaga gttcaacaaa    300
agccaggatc cgttccgtcg ggcggtactg tttttatatt tgaaccgcta cggttacaac    360
ggcctgtgtc gttacaatct gcgcggtgag tttaacgtgc cgttcggccg ctacaaaaaa    420
ccctatttcc cggaagcaga gttgtatcac ttcgctgaaa aagcgcagaa tgccttttc     480 tattgtgagt cttacgccga tagcatggcg cgcgcagatg atgcatccgt cgtctattgc    540
gatccgcctt atgcaccgct gtctgcgacc gccaactta cggcgtatca cacaaacagt    600
tttacgcttg aacaacaagc gcatctggcg gagatcgccg aaggtctggt tgagcgccat    660
attccagtgc tgatctccaa tcacgatacg atgttaacgc gtgagtggta tcagcgcgca    720
aaattgcatg tcgtcaaagt tcgacgcagt ataagcagca acggcggcac acgtaaaaag    780
gtggacgaac tgctggcttt gtacaaacca ggagtcgttt cacccgcgaa aaaataa       837

<210> SEQ ID NO 93
<211> LENGTH: 20
<212> TYPE: DNA
<213> ORGANISM: Escherichia coli

<400> SEQUENCE: 93
```

```
ccctgcttga tgatattaaa                                            20

<210> SEQ ID NO 94
<211> LENGTH: 20
<212> TYPE: DNA
<213> ORGANISM: Escherichia coli

<400> SEQUENCE: 94
aaaatcgcgc tttttgaag                                             20

<210> SEQ ID NO 95
<211> LENGTH: 20
<212> TYPE: DNA
<213> ORGANISM: Escherichia coli

<400> SEQUENCE: 95
tcccgaaaca aattgcgccg                                            20

<210> SEQ ID NO 96
<211> LENGTH: 20
<212> TYPE: DNA
<213> ORGANISM: Escherichia coli

<400> SEQUENCE: 96
ccaggatccg ttccgtcggg                                            20

<210> SEQ ID NO 97
<211> LENGTH: 8361
<212> TYPE: DNA
<213> ORGANISM: Artificial Sequence
<220> FEATURE:
<223> OTHER INFORMATION: Synthetic sequence

<400> SEQUENCE: 97
acattaccct gttatcccta gatacattac cctgttatcc cagatgacat accctgttat    60
ccctagatga cattaccctg ttatcccaga tgacattacc ctgttatccc tagatacatt   120
accctgttat cccagatgac ataccctgtt atccctagat gacattaccc tgttatccca   180
gatgacatta ccctgttatc cctagataca ttaccctgtt atcccagatg acataccctg   240
ttatccctag atgacattac cctgttatcc cagatgacat accctgttat ccctagata    300 cattaccctg ttatcccaga tgacataccc tgttatccct agatgacatt accctgttat   360
cccagatgac attaccctgt tatccctaga tacattaccc tgttatccca gatgacatac   420
cctgttatcc ctagatgaca ttaccctgtt atcccagatg acattaccct gttatcccta   480
gatacattac cctgttatcc cagatgacat accctgttat ccctagatga cattaccctg   540
ttatcccaga tgacattacc ctgttatccc tagatacatt accctgttat cccagatgac   600
ataccctgtt atccctagat gacattaccc tgttatccca gatgacatta ccctgttatc   660
cctagataca ttaccctgtt atcccagatg acataccctg ttatccctag atgacattac   720
cctgttatcc cagataaact caatgatgat gatgatgatg gtcgagactc agcggccgcg   780
gtgccagggc gtgcccttgg gctcccgggc gcgacaagc ttctgtaggt ttttaggcat   840
aaaactatat gatttacccc taatctttta aaatgcccct aaaattcaa ataaaggca    900 tttaaattt aaatatttct tgtgataaag tttgttaaaa aggagtggtt ttatgactgt    960
tatgtggtta tcgattatag gtatgtggtt ttgtattgga atggcatttt ttgctatcaa  1020
ggttattaaa aataaaaatt agaccacgca tttatgccga gaaatttat tgtgcgttga  1080
```

```
gaagaaccct taactaaact tgcagacgaa tgtcggcata gcgtgagcta ttaagccgac    1140
cattcgacaa gttttgggat tgttaagggt tccgaggctc aacgtcaata aagcaattgg    1200
aataaagaag cgaaaaagga gaagtcggtt cagaaaaaga agcatatgca tctggagctg    1260
taatataaaa accttcttca actaacgggg caggttagtg acattagaaa accgactgta    1320
aaaagtacag tcggcattat ctcatattat aaaagccagt cattaggcct atctgacaat    1380
tcctgaatag agttcataaa caatcctgca tgataaccat cacaaacaga atgatgtacc    1440
tgtaaagata gcggtaaata tattgaatta cctttattaa tgaattttcc tgctgtaata    1500
atgggtagaa ggtaattact attattattg atatttaagt taaacccagt aaatgaagtc    1560
catggaataa tagaaagaga aaaagcattt tcaggtatag gtgttttggg aaacaatttc    1620
cccgaaccat tatatttctc tacatcagaa aggtataaat cataaaactc tttgaagtca    1680
ttctttacag gagtccaaat accagagaat gtttagata caccatcaaa aattgtataa    1740
agtggctcta acttatccca ataacctaac tctccgtcgc tattgtaacc agttctaaaa    1800
gctgtatttg agtttatcac ccttgtcact aagaaaataa atgcagggta aaatttatat    1860
ccttcttgtt ttatgtttcg gtataaaaca ctaatatcaa tttctgtggt tatactaaaa    1920
gtcgtttgtt ggttcaaata atgattaaat atctcttttc tcttccaatt gtctaaatca    1980
attttattaa agttcatttg atatgcctcc taaattttta tctaaagtga atttaggagg    2040
cttacttgtc tgctttcttc attagaatca atccttttt aaaagtcaat attactgtaa    2100
cataaatata tattttaaaa atatcccact ttatccaatt ttcgtttgtt gaactaatgg    2160
gtgctttagt tgaagaataa aagaccacat taaaaaatgt ggtcttttgt gttttttaa    2220 aggatttgag cgtagcgaaa atccttttc tttcttatct tgataataag ggtaactatt    2280
gccggcgagg ctagttaccc ttaagttatt ggtatgactg gttttaagcg caaaaaagt    2340 tgcttttcg tacctattaa tgtatcgttt taaatgaata gtaaaaaaca tacatagaaa    2400
ggggaaaaag caacttttt tattgtcata gtttgtgaaa actaagttgt ttttatgtgt    2460
tataacatgg aaaagtatac tgagaaaaaa caaagaaatc aagtatttca gaaatttatt    2520
aaacgtcata ttggagagaa tcaaatggat ttagttgaag attgcaatac atttctgtct    2580
tttgtagctg ataaaactt agaaaaacag aaattatata aagctaattc ttgtaaaaat    2640
cgattttgtc ctgtctgtgc ttggagaaaa gctagaaaag atgcattggg tttatctttg    2700
atgatgcaat atattaagca gcaagagaaa aaggagttta tcttttaac tttgactaca    2760 cctaatgtaa tgagtgatga attagaaaat gaaataaaac gttataataa ttcttttaga    2820
aaacttataa agagaaaaaa agtaggtagt gttataaagg gatatgttcg taagttagag    2880
attacatata ataaaaaaag agatgattat aatcctcatt ttcatgtgtt aattgcagta    2940
aataaatcgt atttcacaga taaagatat tatattagcc aacaagaatg gttagattta    3000
tggcgtgatg taacgggcat ttcagaaata acacaagttc aagttcaaaa aataagacaa    3060
aataataata aagaattata tgaaatggct aagtattctg gtaaagatag tgattattta    3120
ataaatcaaa aagtctttga tgcattttat aaatcactta aaggtaaaca ggtattagtt    3180
tattcaggat tatttaaaga ggctaaaaag aaattaaaaa atggggattt agattactta    3240
aaagaaattg atccaaccga atatatctat caaatttttt atatttggaa acaaaaagag    3300
tatttagcta gtgaacttta tgacttaaca gaacaagaaa aaagagaaat taatcacaaa    3360
atgatagacg aaatcgagga agaacaataa caaaatataa gtgctaacag tcgtctgcaa    3420
gtttagttaa gggttcttct caacgcacaa taaattttct cggcataaat gcgtggtcta    3480
```

```
attttttattt ttaataacct tgatagcaaa aaatgccatt ccaatacaaa accacatacc   3540
tataatcgat aaccacataa cagtcataaa accactcctt tttaacaaac tttatcacaa   3600
gaaatatttt ggcattctac gactataact taaatttata ttttttactt tataatatat   3660
aattgattat agaataatgt tgctcatatc gtttgccaac atctagtact caaattacac   3720
tatgttacac ttggtaatat taaccgaact tcccctgtcc aaattagata agaggtaata   3780
ataaatggaa ataattttta tagtaaatga aaatgagaag cgtgtattaa aacaaatttt   3840
caataacagc aatatttcac gaacacaaat atcgaagaat ttagaactta ataaagctac   3900
tatttctaac attctgaaca acttaaaaca caagagttta gttaatgaag taggagaagg   3960
taatagtact aaaagtggtg gacgaaagcc tattttactc gaaattaacc aaaaatatgg   4020
ctactatatt tctatggatt taacatatga ttccgttgaa ttaatgtaca actactttga   4080
tgctactata ttaaagcaag attcctacga attaaatgat aaaaatgtaa gcagtatatt   4140
acaaatttta aaatctaata taaacgtctc agaaaaatat gatacgttat atgggttact   4200
tggtatatct atatccatac acggtatcgt tgacgatgag caaaacataa tcaatcttcc   4260
ttttcataaa aatgagaaac gcacatttac cgatgaatta aagtcattca caaatgttcc   4320
tgtcgttata gaaaatgaag caaatttatc agcgctatat gaaaaaagtt tatatattaa   4380
ttcaaacata aataatttga ttactttaag tattcacaag ggtataggcg ctggcatcct   4440
aataaataaa aaactttatc gtggctcaaa tggagaggct ggagagatag gtaagacatt   4500
ggttttggaa tctataaata acaatgacaa caaatattat aaaatcgaag atatatgctc   4560
ccaagacgct ttaatacaga aaataaataa taggttgggc gtcacattga cgtttacaga   4620
actaatccaa tattcaaacg aaggaaattc aattgttgct catgaaatta acaatttat   4680
taataaaatg acagttctga ttcataattt gaatacacaa tttaacccag cgctatttta  4740
tattaactgt cctttaatta tgaattacc aaatatttta aatgaaatta agagcaatt   4800
ctcctgtttt tctcaaggca gtccagttca attacattta actactaatg taaaacaagc   4860
tactttattg ggtggcactt tagcaataat gcaaaaaaca ttaaatataa ataacattca   4920
aatgaatatt aaataattac agcagtctga gttataaaat agatatctcg gaccgtcata   4980
aaaaatttat ttgctttcag gaaaattttt ctgtataata gattcaagtt agtttgttta   5040
ttaaattaac caactaaaat gtagaattcg agctcggtac ccggggatcc tctagagtcg   5100
accccaactg gggtaacctt tgagttctct cagttggggg taatcagcat catgatgtgg   5160
taccacatca tgatgctgat tataagaatg cggccgccac actctagtgg atctcgagtt   5220
aataattcag aagaactcgt caagaaggcg atagaaggcg atgcgctgcg aatcgggagc   5280
ggcgataccg taaagcacga ggaagcggtc agcccattcg ccgccaagct cttcagcaat   5340
atcacgggta gccaacgcta tgtcctgata gcggtccgcc acacccagcc ggccacagtc   5400
gatgaatcca gaaaagcggc catttttcac catgatattc ggcaagcagg catcgccatg   5460
ggtcacgacg agatcctcgc cgtcgggcat gctcgccttg agcctggcga acagttcggc   5520
tggcgcgagc ccctgatgct cttcgtccag atcatcctga tcgacaagac cggcttccat   5580
ccgagtacgt gctcgctcga tgcgatgttt cgcttggtgg tcgaatgggc aggtagccgg   5640
atcaagcgta tgcagccgcc gcattgcatc agccatgatg gatactttct cggcaggagc   5700
aaggtgagat gacaggagat cctgccccgg cacttcgccc aatagcagcc agtcccttcc   5760
cgcttcagtg acaacgtcga gcacagctgc gcaaggaacg cccgtcgtgg ccagccacga   5820
```

-continued

| | | | | | |
|---|---|---|---|---|---|
| tagccgcgct | gcctcgtctt | gcagttcatt | cagggcaccg | gacaggtcgg | tcttgacaaa | 5880 |
| aagaaccggg | cgcccctgcg | ctgacagccg | gaacacggcg | gcatcagagc | agccgattgt | 5940 |
| ctgttgtgcc | cagtcatagc | cgaatagcct | ctccacccaa | gcggccggag | aacctgcgtg | 6000 |
| caatccatct | tgttcaatca | tgcgaaacga | tcctcatcct | gtctcttgat | cagagcttga | 6060 |
| tccccctgcgc | catcagatcc | ttggcggcga | gaaagccatc | cagtttactt | tgcagggctt | 6120 |
| cccaacctta | ccagagggcg | ccccagctgg | caattccggt | tcgcttgctg | tccataaaac | 6180 |
| cgcccagtct | agctatcgcc | atgtaagccc | actgcaagct | acctgctttc | tctttgcgct | 6240 |
| tgcgttttcc | cttgtccaga | tagcccagta | gctgacattc | atccggggtc | agcaccgttt | 6300 |
| ctgcggactg | gctttctacg | tgctcgaggg | gggccaaacg | gtctccagct | tggctgtttt | 6360 |
| ggcggatgag | agaagatttt | cagcctgata | cagattaaat | cagaacgcag | aagcggtctg | 6420 |
| ataaaacaga | atttgcctgg | cggcagtagc | gcggtggtcc | cacctgaccc | catgccgaac | 6480 |
| tcagaagtga | aacgccgtag | cgccgatggt | agtgtggggt | ctccccatgc | gagagtaggg | 6540 |
| aactgccagg | catcaaataa | aacgaaaggc | tcagtcgaaa | gactgggcct | ttcgttttat | 6600 |
| ctgttgtttg | tcggtgaacg | ctctcctgag | taggacaaat | ccgccgggag | cggatttgaa | 6660 |
| cgttgcgaag | caacggcccg | gagggtggcg | ggcaggacgc | ccgccataaa | ctgccaggca | 6720 |
| tcaaattaag | cagaaggcca | tcctgacgga | tggcctttt | gcgtttctac | aaactctttt | 6780 |
| gtttattttt | ctaaatacat | tcaaatatgt | atccgctcat | gaccaaaatc | ccttaacgtg | 6840 |
| agttttcgtt | ccactgagcg | tcagaccccg | tagaaaagat | caaaggatct | tcttgagatc | 6900 |
| ctttttttct | gcgcgtaatc | tgctgcttgc | aaacaaaaaa | accaccgcta | ccagcggtgg | 6960 |
| tttgtttgcc | ggatcaagag | ctaccaactc | tttttccgaa | ggtaactggc | ttcagcagag | 7020 |
| cgcagatacc | aaatactgtc | cttctagtgt | agccgtagtt | aggccaccac | ttcaagaact | 7080 |
| ctgtagcacc | gcctacatac | ctcgctctgc | taatcctgtt | accagtggct | gctgccagtg | 7140 |
| gcgataagtc | gtgtcttacc | gggttggact | caagacgata | gttaccggat | aaggcgcagc | 7200 |
| ggtcgggctg | aacggggggt | tcgtgcacac | agcccagctt | ggagcgaacg | acctacaccg | 7260 |
| aactgagata | cctacagcgt | gagctatgag | aaagcgccac | gcttcccgaa | gggagaaagg | 7320 |
| cggacaggta | tccggtaagc | ggcagggtcg | gaacaggaga | gcgcacgagg | gagcttccag | 7380 |
| ggggaaacgc | ctggtatctt | tatagtcctg | tcgggtttcg | ccacctctga | cttgagcgtc | 7440 |
| gatttttgtg | atgctcgtca | ggggggcgga | gcctatggaa | aaacgccagc | aacgcggcct | 7500 |
| ttttacggtt | cctggccttt | tgctggcctt | ttgctcacat | gttctttcct | gcgttatccc | 7560 |
| ctgattctgt | ggataaccgt | attaccgcct | ttgagtgagc | tgataccgct | cgccgcagcc | 7620 |
| gaacgaccga | gcgcagcgag | tcagtgagcg | aggaagcgga | agagcgcctg | atgcggtatt | 7680 |
| ttctccttac | gcatctgtgc | ggtatttcac | accgcatatg | gtgcactctc | agtacaatct | 7740 |
| gctctgatgc | cgcatagtta | agccagtata | cactccgcta | tcgctacgtg | actgggtcat | 7800 |
| ggctgcgccc | cgacacccgc | caacacccgc | tgacgcgccc | tgacgggctt | gtctgctccc | 7860 |
| ggcatccgct | tacagacaag | ctgtgaccgt | ctccgggagc | tgcatgtgtc | agaggttttc | 7920 |
| accgtcatca | ccgaaacgcg | cgaggcagca | gatcaattcg | cgcgcgaagg | cgaagcggca | 7980 |
| tgcataatgt | gcctgtcaaa | tggacgaagc | agggattctg | caaaccctat | gctactccgt | 8040 |
| caagccgtca | attgtctgat | tcgttaccaa | ttatgacaac | ttgacggcta | catcattcac | 8100 |
| tttttcttca | caaccggcac | ggaactcgct | cgggctggcc | ccggtgcatt | ttttaaatac | 8160 |
| ccgcgagaaa | tagagttgat | cgtcaaaacc | aacattgcga | ccgacggtgg | cgataggcat | 8220 |

```
ccgggtggtg ctcaaaagca gcttcgcctg gctgatacgt tggtcctcgc gccagcttaa    8280
gacgctaatc cctaactgct ggcggaaaag atgtgacaga cgcgacggcg acaagcaaac    8340
atgctgtgcg acgctggcga t                                              8361
```

<210> SEQ ID NO 98
<211> LENGTH: 4322
<212> TYPE: DNA
<213> ORGANISM: Artificial Sequence
<220> FEATURE:
<223> OTHER INFORMATION: Synthetic sequence

<400> SEQUENCE: 98

```
gggctccccg gcgcgacaa gcttctgtag gttttaggc ataaaactat atgatttacc       60
cctaaatctt taaatgccc cttaaaattc aaaataaagg catttaaaat ttaaatatt     120 cttgtgataa agtttgttaa aaaggagtgg ttttatgact gttatgtggt tatcgattat    180
aggtatgtgg ttttgtattg gaatggcatt ttttgctatc aaggttatta aaataaaaa     240 ttagaccacg catttatgcc gagaaattt attgtgcgtt gagaagaacc cttaactaaa     300
cttgcagacg aatgtcggca tagcgtgagc tattaagccg accattcgac aagttttggg    360
attgttaagg gttccgaggc tcaacgtcaa taaagcaatt ggaataaaga agcgaaaaag    420
gagaagtcgg ttcagaaaaa gaagcatatg catctggagc tgtaatataa aaaccttctt    480
caactaacgg ggcaggttag tgacattaga aaaccgactg taaaaagtac agtcggcatt    540
atctcatatt ataaaagcca gtcattaggc ctatctgaca attcctgaat agagttcata    600
aacaatcctg catgataacc atcacaaaca gaatgatgta cctgtaaaga tagcggtaaa    660
tatattgaat tacctttatt aatgaatttt cctgctgtaa taatgggtag aaggtaatta    720
ctattattat tgatatttaa gttaaaccca gtaaatgaag tccatggaat aatagaaaga    780
gaaaaagcat tttcaggtat aggtgttttg ggaaacaatt ccccgaacc attatatttc     840 tctacatcag aaaggtataa atcataaaac tctttgaagt cattctttac aggagtccaa    900
ataccagaga atgttttaga tacaccatca aaaattgtat aaagtggctc taacttatcc    960
caataaccta actctccgtc gctattgtaa ccagttctaa aagctgtatt tgagtttatc   1020
acccttgtca ctaagaaaat aaatgcaggg taaaatttat atccttcttg ttttatgttt   1080
cggtataaaa cactaatatc aatttctgtg ttatactaa aagtcgtttg ttggttcaaa    1140
taatgattaa atatctcttt tctcttccaa ttgtctaaat caatttttatt aaagttcatt   1200 tgatatgcct cctaaatttt tatctaaagt gaatttagga ggcttacttg tctgctttct   1260
tcattagaat caatcctttt ttaaaagtca atattactgt aacataaata tatattttaa   1320
aaatatccca ctttatccaa ttttcgtttg ttgaactaat gggtgcttta gttgaagaat   1380
aaaagaccac attaaaaaat gtggtctttt gtgttttttt aaaggatttg agcgtagcga   1440
aaaatccttt tctttcttat cttgataata agggtaacta ttgccggcga ggctagttac   1500
ccttaagtta ttggtatgac tggttttaag cgcaaaaaaa gttgcttttt cgtacctatt   1560
aatgtatcgt tttaaatgaa tagtaaaaaa catacataga aaggggaaaa agcaactttt   1620
tttattgtca tagtttgtga aaactaagtt gttttttatgt gttataacat ggaaaagtat   1680
actgagaaaa aacaaagaaa tcaagtattt cagaaattta ttaaacgtca tattggagag   1740
aatcaaatgg atttagttga agattgcaat acatttctgt cttttgtagc tgataaaact   1800
ttagaaaaac agaaattata taaagctaat tcttgtaaaa atcgattttg tcctgtctgt   1860
```

```
gcttggagaa aagctagaaa agatgcattg ggtttatctt tgatgatgca atatattaag    1920
cagcaagaga aaaaggagtt tatctttta actttgacta cacctaatgt aatgagtgat    1980
gaattagaaa atgaaataaa acgttataat aattctttta gaaaacttat aaagagaaaa   2040
aaagtaggta gtgttataaa gggatatgtt cgtaagttag agattacata taataaaaaa   2100
agagatgatt ataatcctca tttcatgtg ttaattgcag taaataaatc gtatttcaca    2160
gataaaagat attatattag ccaacaagaa tggttagatt tatggcgtga tgtaacgggc   2220
atttcagaaa taacacaagt tcaagttcaa aaaataagac aaaataataa taagaatta    2280 tatgaaatgg ctaagtattc tggtaaagat agtgattatt taataaatca aaagtctt     2340 gatgcatttt ataaatcact taaaggtaaa caggtattag tttattcagg attatttaaa   2400
gaggctaaaa agaaattaaa aaatgggat ttagattact taaagaaat tgatccaacc     2460 gaatatatct atcaaatttt ttatatttgg aaacaaaaag agtatttagc tagtgaactt   2520
tatgacttaa cagaacaaga aaaagagaa attaatcaca aaatgataga cgaaatcgag    2580
gaagaacaat aacaaaatat aagtgctaac agtcgtctgc aagtttagtt aagggttctt   2640
ctcaacgcac aataaatttt ctcggcataa atgcgtggtc taattttttat tttaataac   2700 cttgatagca aaaaatgcca ttccaataca aaaccacata cctataatcg ataaccacat   2760
aacagtcata aaaccactcc ttttaacaa actttatcac aagaaatatt ttggcattct    2820
acgactataa cttaaattta tattttac tttataatat ataattgatt atagaataat     2880
gttgctcata tcgtttgcca acatctagta ctcaaattac actatgttac acttggtaat   2940
attaaccgaa cttccctgt ccaaattaga taagaggtaa taataaatgg aaaataattt    3000
tatagtaaat gaaatgaga agcgtgtatt aaaacaaatt ttcaataaca gcaatatttc    3060
acgaacacaa atatcgaaga atttagaact taataaagct actatttcta acattctgaa   3120
caacttaaaa cacaagagtt tagttaatga agtaggagaa ggtaatagta ctaaaagtgg   3180
tggacgaaag cctattttac tcgaaattaa ccaaaaatat ggctactata tttctatgga   3240
tttaacatat gattccgttg aattaatgta caactacttt gatgctacta tattaaagca   3300
agattcctac gaattaaatg ataaaaatgt aagcagtata ttacaaattt taaaatctaa   3360
tataaacgtc tcagaaaaat atgatacgtt atatgggtta cttggtatat ctatatccat   3420
acacggtatc gttgacgatg agcaaaaacat aatcaatctt cctttcata aaaatgagaa   3480 acgcacattt accgatgaat aaagtcatt cacaaatgtt cctgtcgtta tagaaaatga   3540
agcaaattta tcagcgctat atgaaaaaag tttatatatt aattcaaaca taaataattt   3600
gattacttta agtattcaca agggtatagg cgctggcatc ctaataaata aaaaacttta   3660
tcgtggctca aatggagagg ctggagagat aggtaagaca ttggttttgg aatctataaa   3720
taacaatgac aacaaatatt ataaaatcga agatatatgc tcccaagacg ctttaataca   3780
gaaaataaat aataggttgg gcgtcacatt gacgtttaca gaactaatcc aatattacaa   3840
cgaaggaaat tcaattgttg ctcatgaaat taaacaattt attaataaaa tgacagttct   3900
gattcataat ttgaatacac aatttaaccc agacgctatt tatattaact gtcctttaat   3960
taatgaatta ccaaatattt taaatgaaat taaagagcaa ttctcctgtt tttctcaagg   4020
cagtccagtt caattacatt taactactaa tgtaaaacaa gctactttat ggtggcac     4080 tttagcaata atgcaaaaaa cattaaatat aaataacatt caaatgaata ttaaataatt   4140
acagcagtct gagttataaa atagatatct cggaccgtca taaaaatttt atttgctttc   4200
aggaaaattt ttctgtataa tagattcaag ttagtttgtt tattaaatta accaactaaa   4260
```

-continued

```
atgtagaatt cgagctcggt acccggggat cctctagagt cgaccccaac tggggtaacc    4320
tt                                                                  4322
```

<210> SEQ ID NO 99
<211> LENGTH: 8361
<212> TYPE: DNA
<213> ORGANISM: Artificial Sequence
<220> FEATURE:
<223> OTHER INFORMATION: Synthetic sequence

<400> SEQUENCE: 99

```
acattaccct gttatcccta gatacattac cctgttatcc cagatgacat accctgttat     60
ccctagatga cattaccctg ttatcccaga tgacattacc ctgttatccc tagatacatt    120
accctgttat cccagatgac ataccctgtt atccctagat gacattaccc tgttatccca    180
gatgacatta ccctgttatc cctagataca ttaccctgtt atcccagatg acataccctg    240
ttatccctag atgacattac cctgttatcc cagatgacat accctgtta tccctagata    300 cattaccctg ttatcccaga tgacataccc tgttatccct agatgacatt accctgttat    360
cccagatgac attaccctgt tatccctaga tacattaccc tgttatccca gatgacatac    420
cctgttatcc ctagatgaca ttaccctgtt atcccagatg acattaccct gttatcccta    480
gatacattac cctgttatcc cagatgacat accctgttat ccctagatga cattaccctg    540
ttatcccaga tgacattacc ctgttatccc tagatacatt accctgttat cccagatgac    600
ataccctgtt atccctagat gacattaccc tgttatccca gatgacatta ccctgttatc    660
cctagataca ttaccctgtt atcccagatg acataccctg ttatccctag atgacattac    720
cctgttatcc cagataaact caatgatgat gatgatgatg tcgagactc agcggccgcg    780 gtgccagggc gtgcccttgg gctccccggg cgcgacaagc ttctgtaggt ttttaggcat    840
aaaactatat gatttacccc taatctttta aaatgcccct taaaattcaa ataaaggca    900 tttaaaattt aaatatttct tgtgataaag tttgttaaaa aggagtggtt ttatgactgt    960
tatgtggtta tcgattatag gtatgtggtt ttgtattgga atggcatttt ttgctatcaa   1020
ggttattaaa aataaaaatt agaccacgca tttatgccga gaaaatttat tgtgcgttga   1080 gaagaacccct taactaaact tgcagacgaa tgtcggcata gcgtgagcta ttaagccgac   1140
cattcgacaa gttttgggat tgttaagggt tccgaggctc aacgtcaata aagcaattgg   1200
aataaagaag cgaaaaggaa gaagtcggtt cagaaaaaga aggatatgga tctggagctg   1260
taatataaaa accttcttca actaacgggg caggttagtg acattagaaa accgactgta   1320
aaaagtacag tcggcattat ctcatattat aaaagccagt cattaggcct atctgacaat   1380
tcctgaatag agttcataaa caatcctgca tgataaccat cacaaacaga atgatgtacc   1440
tgtaaagata gcggtaaata tattgaatta cctttattaa tgaattttcc tgctgtaata   1500
atgggtagaa ggtaaattact attattattg atatttaagt taaacccagt aaatgaagtc   1560
catggaataa tagaaagaga aaaagcattt tcaggtatag gtgttttggg aaacaatttc   1620
cccgaaccat tatatttctc tacatcagaa aggtataaat cataaaactc tttgaagtca   1680
ttctttacag gagtccaaat accagagaat gttttagata caccatcaaa aattgtataa   1740
agtggctcta acttatccca ataacctaac tctccgtcgc tattgtaacc agttctaaaa   1800
gctgtatttg agtttatcac ccttgtcact aagaaaataa atgcagggta aaatttatat   1860
ccttcttgtt ttatgtttcg gtataaaaca ctaatatcaa tttctgtggt tatactaaaa   1920
```

```
gtcgtttgtt ggttcaaata atgattaaat atctcttttc tcttccaatt gtctaaatca    1980 atttttattaa agttcatttg atatgcctcc taaattttta tctaaagtga atttaggagg    2040
cttacttgtc tgctttcttc attagaatca atcctttttt aaaagtcaat attactgtaa    2100
cataaatata tattttaaaa atatcccact ttatccaatt ttcgtttgtt gaactaatgg    2160
gtgctttagt tgaagaataa aagaccacat taaaaaatgt ggtcttttgt gttttttaa     2220 aggatttgag cgtagcgaaa atccttttc tttcttatct tgataataag ggtaactatt      2280
gccggcgagg ctagttaccc ttaagttatt ggtatgactg gttttaagcg caaaaaagt      2340 tgcttttttcg tacctattaa tgtatcgttt taaatgaata gtaaaaaaca tacatagaaa    2400
ggggaaaaag caactttttt tattgtcata gtttgtgaaa actaagttgt ttttatgtgt    2460
tataacatgg aaaagtatac tgagaaaaaa caagaaatc aagtatttca gaaatttatt      2520
aaacgtcata ttggagagaa tcaaatggat ttagttgaag attgcaatac atttctgtct   2580
tttgtagctg ataaaacttt agaaaaacag aaattatata aagctaattc ttgtaaaaat    2640
cgattttgtc ctgtctgtgc ttggagaaaa gctagaaaaa atgcattggg tttatctttg    2700
atgatgcaat atattaagca gcaagagaaa aaggagttta tcttttttaac tttgactaca   2760 cctaatgtaa tgagtgatga attagaaaat gaaataaaac gttataataa ttcttttaga    2820
aaacttataa agagaaaaaa agtaggtagt gttataaagg gatatgttcg taagttagag    2880
attacatata ataaaaaaag agatgattat aatcctcatt ttcatgtgtt aattgcagta    2940
aataaatcgt atttcacaga taaaagatat tatattagcc aacaagaatg gttagattta   3000
tggcgtgatg taacgggcat ttcagaaata acacaagttc aagttcaaaa aataagacaa   3060
aataataata aagaattata tgaaatggct aagtattctg gtaaagatag tgattatta    3120 ataaatcaaa aagtctttga tgcattttat aaatcactta aaggtaaaca ggtattagtt    3180
tattcaggat tatttaaaga ggctaaaaag aaattaaaaa atggggattt agattactta    3240
aaagaaattg atccaaccga atatatctat caaatttttt atatttggaa acaaaaagag    3300
tatttagcta gtgaacttta tgacttaaca gaacaagaaa aagagaaat taatcacaaa     3360 atgatagacg aaatcgagga agaacaataa caaaatataa gtgctaacag tcgtctgcaa    3420
gtttagttaa gggttcttct caacgcacaa taaattttct cggcataaat gcgtggtcta    3480
atttttattt ttaataacct tgatagcaaa aaatgccatt ccaatacaaa accacatacc    3540
tataatcgat aaccacataa cagtcataaa accactcctt tttaacaaac tttatcacaa    3600
gaaatatttt ggcattctac gactataact taaatttata tttttttactt tataatatat    3660 aattgattat agaataatgt tgctcatatc gtttgccaac atctagtact caaattacac    3720
tatgttacac ttggtaatat taccgaact tcccctgtcc aaattagata agaggtaata     3780
ataaatggaa aataatttta tagtaaatga aaatgagaag cgtgtattaa aacaaatttt    3840
caataacagc aatatttcac gaacacaaat atcgaagaat ttagaactta ataaagctac    3900
tatttctaac attctgaaca acttaaaaca caagagttta gttaatgaag taggagaagg    3960
taatagtact aaaagtggtg gacgaaagcc tattttactc gaaattaacc aaaaatatgg    4020
ctactatatt tctatggatt taacatatga ttccgttgaa ttaatgtaca actactttga    4080
tgctactata ttaaagcaag attcctacga attaaatgat aaaaatgtaa gcagtatatt    4140
acaaatttta aaatctaata taaacgtctc agaaaaatat gatacgttat atgggttact    4200
tggtatatct atatccatac acggtatcgt tgacgatgag caaaacataa tcaatcttcc    4260
ttttcataaa aatgagaaac gcacattta cgatgaatta aagtcattca caaatgttcc    4320
```

```
tgtcgttata gaaaatgaag caaatttatc agcgctatat gaaaaaagtt tatatattaa    4380
ttcaaacata aataatttga ttactttaag tattcacaag ggtataggcg ctggcatcct    4440
aataaataaa aaactttatc gtggctcaaa tggagaggct ggagagatag gtaagacatt    4500
ggttttggaa tctataaata acaatgacaa caaatattat aaaatcgaag atatatgctc    4560
ccaagacgct ttaatacaga aaataaataa taggttgggc gtcacattga cgtttacaga    4620
actaatccaa tattcaacg aaggaaattc aattgttgct catgaaatta aacaatttat     4680
taataaaatg acagttctga ttcataattt gaatacacaa tttaacccag acgctattta    4740
tattaactgt cctttaatta atgaattacc aaatattta aatgaaatta aagagcaatt     4800
ctcctgtttt tctcaaggca gtccagttca attacattta actactaatg taaaacaagc    4860
tactttattg ggtggcactt tagcaataat gcaaaaaaca ttaaatataa ataacattca    4920
aatgaatatt aataattac agcagtctga gttataaaat agatatctcg gaccgtcata    4980
aaaaatttat ttgctttcag gaaaattttt ctgtataata gattcaagtt agtttgttta    5040
ttaaattaac caactaaaat gtagaattcg agctcggtac ccggggatcc tctagagtcg    5100
accccaactg gggtaacctt tgagttctct cagttggggg taatcagcat catgatgtgg    5160
taccacatca tgatgctgat tataagaatg cggccgccac actctagtgg atctcgagtt    5220
aataattcag aagaactcgt caagaaggcg atagaaggcg atgcgctgcg aatcgggagc    5280
ggcgataccg taaagcacga ggaagcggtc agcccattcg ccgccaagct cttcagcaat    5340
atcacgggta gccaacgcta tgtcctgata gcggtccgcc acacccagcc ggccacagtc    5400
gatgaatcca gaaaagcggc cattttccac catgatattc ggcaagcagg catcgccatg    5460
ggtcacgacg agatcctcgc cgtcgggcat gctcgccttg agcctggcga acagttcggc    5520
tggcgcgagc ccctgatgct cttcgtccag atcatcctga tcgacaagac cggcttccat    5580
ccgagtacgt gctcgctcga tgcgatgttt cgcttggtgg tcgaatgggc aggtagccgg    5640
atcaagcgta tgcagccgcc gcattgcatc agccatgatg gatactttct cggcaggagc    5700
aaggtgagat gacaggagat cctgccccgg cacttcgccc aatagcagcc agtcccttcc    5760
cgcttcagtg acaacgtcga gcacagctgc gcaaggaacg cccgtcgtgg ccagccacga    5820
tagccgcgct gcctcgtctt gcagttcatt cagggcaccg gacaggtcgg tcttgacaaa    5880
aagaaccggg cgcccctgcg ctgacagccg gaacacggcg gcatcagagc agccgattgt    5940
ctgttgtgcc cagtcatagc cgaatagcct ctccacccaa gcggccggag aacctgcgtg    6000
caatccatct tgttcaatca tgcgaaacga tcctcatcct gtctcttgat cagagcttga    6060
tcccctgcgc catcagatcc ttggcggcga aaagccatc cagtttactt gcagggctt      6120 cccaacctta ccgagggcg cccagctgg caattccggt tcgcttgctg tccataaaac      6180
cgcccagtct agctatcgcc atgtaagccc actgcaagct acctgctttc tctttgcgct    6240
tgcgttttcc cttgtccaga tagcccagta gctgacattc atccgggtc agcaccgttt     6300 ctgcggactg gctttctacg tgctcgaggg gggccaaacg gtctccagct tggctgtttt    6360
ggcggatgag agaagatttt cagcctgata cagattaaat cagaacgcag aagcggtctg    6420
ataaaacaga atttgcctgg cggcagtagc gcggtggtcc cacctgaccc catgccgaac    6480
tcagaagtga aacgccgtag cgccgatggt agtgtggggt ctccccatgc gagagtaggg    6540
aactgccagg catcaaataa aacgaaaggc tcagtcgaaa gactgggcct ttcgttttat    6600
ctgttgtttg tcggtgaacg ctctcctgag taggacaaat ccgccgggag cggatttgaa    6660
```

| | |
|---|---|
| cgttgcgaag caacggcccg agggtggcg gcaggacgc ccgccataaa ctgccaggca | 6720 |
| tcaaattaag cagaaggcca tcctgacgga tggccttttt gcgtttctac aaactctttt | 6780 |
| gtttattttt ctaaatacat tcaaatatgt atccgctcat gaccaaaatc ccttaacgtg | 6840 |
| agttttcgtt ccactgagcg tcagacccg tagaaaagat caaggatct tcttgagatc | 6900 |
| cttttttct gcgcgtaatc tgctgcttgc aaacaaaaaa accaccgcta ccagcggtgg | 6960 |
| tttgtttgcc ggatcaagag ctaccaactc tttttccgaa ggtaactggc ttcagcagag | 7020 |
| cgcagatacc aaatactgtc cttctagtgt agccgtagtt aggccaccac ttcaagaact | 7080 |
| ctgtagcacc gcctacatac ctcgctctgc taatcctgtt accagtggct gctgccagtg | 7140 |
| gcgataagtc gtgtcttacc gggttggact caagacgata gttaccggat aaggcgcagc | 7200 |
| ggtcgggctg aacggggggt tcgtgcacac agcccagctt ggagcgaacg acctacaccg | 7260 |
| aactgagata cctacagcgt gagctatgag aaagcgccac gcttcccgaa gggagaaagg | 7320 |
| cggacaggta tccggtaagc ggcagggtcg aacaggaga gcgcacgagg gagcttccag | 7380 |
| gggaaacgc ctggtatctt tatagtcctg tcgggtttcg ccacctctga cttgagcgtc | 7440 |
| gattttgtg atgctcgtca ggggggcgga gcctatggaa aaacgccagc aacgcggcct | 7500 |
| ttttacggtt cctggccttt tgctggcctt ttgctcacat gttctttcct gcgttatccc | 7560 |
| ctgattctgt ggataaccgt attaccgcct ttgagtgagc tgataccgct cgccgcagcc | 7620 |
| gaacgaccga gcgcagcgag tcagtgagcg aggaagcgga agagcgcctg atgcggtatt | 7680 |
| ttctccttac gcatctgtgc ggtatttcac accgcatatg gtgcactctc agtacaatct | 7740 |
| gctctgatgc cgcatagtta agccagtata cactccgcta tcgctacgtg actgggtcat | 7800 |
| ggctgcgccc cgacacccgc caacacccgc tgacgcgccc tgacgggctt gtctgctccc | 7860 |
| ggcatccgct tacagacaag ctgtgaccgt ctccgggagc tgcatgtgtc agaggttttc | 7920 |
| accgtcatca ccgaaacgcg cgaggcagca gatcaattcg cgcgcgaagg cgaagcggca | 7980 |
| tgcataatgt gcctgtcaaa tggacgaagc agggattctg caaaccctat gctactccgt | 8040 |
| caagccgtca attgtctgat tcgttaccaa ttatgacaac ttgacggcta catcattcac | 8100 |
| tttttcttca caaccggcac ggaactcgct cgggctggcc ccgtgcatt ttttaaatac | 8160 |
| ccgcgagaaa tagagttgat cgtcaaaacc aacattgcga ccgacggtgg cgataggcat | 8220 |
| ccgggtggtg ctcaaaagca gcttcgcctg gctgatacgt tggtcctcgc gccagcttaa | 8280 |
| gacgctaatc cctaactgct ggcggaaaag atgtgacaga cgcgacggcg acaagcaaac | 8340 |
| atgctgtgcg acgctggcga t | 8361 |

<210> SEQ ID NO 100
<211> LENGTH: 6850
<212> TYPE: DNA
<213> ORGANISM: Artificial Sequence
<220> FEATURE:
<223> OTHER INFORMATION: Synthetic sequence

<400> SEQUENCE: 100

| | |
|---|---|
| ggcggccgca ctggcttact atgttggcac tgatgagggt gtcagtgaag tgcttcatgt | 60 |
| ggcaggagaa aaaggctgc accggtgcgt cagcagaata tgtgatacag gatatattcc | 120 |
| gcttcctcgc tcactgactc gctacgctcg gtcgttcgac tgcggcgagc ggaaatggct | 180 |
| tacgaacggg gcggagattt cctggaagat gccaggaaga tacttaacag ggaagtgaga | 240 |
| gggccgcggc aaagccgttt ttccataggc tccgcccccc tgacaagcat cacgaaatct | 300 |
| gacgctcaaa tcagtggtgg cgaaacccga caggactata aagataccag gcgtttcccc | 360 |

```
ctggcggctc cctcgtgcgc tctcctgttc ctgcctttcg gtttaccggt gtcattccgc    420
tgttatggcc gcgtttgtct cattccacgc ctgacactca gttccgggta ggcagttcgc    480
tccaagctgg actgtatgca cgaaccccc gttcagtccg accgctgcgc cttatccggt     540
aactatcgtc ttgagtccaa cccggaaaga catgcaaaag caccactggc agcagccact    600
ggtaattgat ttagaggagt tagtcttgaa gtcatgcgcc ggttaaggct aaactgaaag    660
gacaagtttt ggtgactgcg ctcctccaag ccagttacct cggttcaaag agttggtagc    720
tcagagaacc ttcgaaaaac cgccctgcaa ggcggttttt tcgttttcag agcaagagat    780
tacgcgcaga ccaaaacgat ctcaagaaga tcatcttatg cggccgcttc tttcctgcgt    840
tatcccctga ttctgtggat aaccgtatta ccgcctttga gtgagctgat accgctcgcc    900
gcagccgaac gaccgagcgc agcgagtcag tgagcgagga agcggaagag cgcctgatgc    960
ggtattttct ccttacgcat ctgtgcggta tttcacaccg cataggaaga tccctcgacc   1020
tgcaggcatg caagcttctg taggtttttta ggcataaaac tatatgattt acccctaaat   1080
ctttaaaatg ccccttaaaa ttcaaaataa aggcatttaa aatttaaata tttcttgtga   1140
taaagtttgt taaaaaggag tggttttatg actgttatgt ggttatcgat ataggtatg   1200 tggttttgta ttggaatggc atttttgct atcaaggtta ttaaaaataa aaattagacc   1260
acgcatttat gccgagaaaa tttattgtgc gttgagaaga acccttaact aaacttgcag   1320
acgaatgtcg gcatagcgtg agctattaag ccgaccattc gacaagtttt gggattgtta   1380
agggttccga ggctcaacgt caataaagca attggaataa agaagcgaaa aaggagaagt   1440
cggttcagaa aaagaaggat atggatctgg agctgtaata taaaaaccctt cttcaactaa   1500 cggggcaggt tagtgacatt agaaaaccga ctgtaaaaag tacagtcggc attatctcat   1560
attataaaag ccagtcatta ggcctatctg acaattcctg aatagagttc ataaacaatc   1620
ctgcatgata accatcacaa acagaatgat gtacctgtaa agatagcggt aaatatattg   1680
aattaccttt attaatgaat tttcctgctg taataatggg tagaaggtaa ttactattat   1740
tattgatatt taagttaaac ccagtaaatg aagtccatgg aataatagaa agagaaaaag   1800
cattttcagg tataggtgtt tgggaaaca atttccccga accattatat ttctctacat   1860
cagaaaggta taaatcataa aactctttga agtcattctt tacaggagtc caaataccag   1920
agaatgtttt agatacacca tcaaaaattg tataaagtgg ctctaactta tcccaataac   1980
ctaactctcc gtcgctattg taaccagttc taaaagctgt atttgagttt atcacccttg   2040
tcactaagaa aataaatgca gggtaaaatt tatatccttc ttgttttatg tttcggtata   2100
aaacactaat atcaatttct gtggttatac taaaagtcgt tgttggttc aaataatgat    2160 taaatatctc ttttctcttc caattgtcta aatcaatttt attaagttc atttgatatg   2220 cctcctaaat ttttatctaa agtgaattta ggaggcttac ttgtctgctt tcttcattag   2280
aatcaatcct ttttttaaaag tcaatattac tgtaacataa atatatattt taaaaatatc   2340
ccactttatc caattttcgt tgttgaact aatgggtgct ttagttgaag aataaaagac    2400
cacattaaaa aatgtggtct tttgtgtttt tttaaaggat ttgagcgtag cgaaaaatcc   2460
ttttctttct tatcttgata ataagggtaa ctattgccgg cgaggctagt tacccttaag   2520
ttattggtat gactggtttt aagcgcaaaa aaagttgctt tttcgtacct attaatgtat   2580
cgttttaaat gaatagtaaa aaacatacat agaaagggga aaaagcaact tttttattg    2640 tcatagtttg tgaaaactaa gttgttttta tgtgttataa catggaaaag tatactgaga   2700
```

-continued

```
aaaaacaaag aaatcaagta tttcagaaat ttattaaacg tcatattgga gagaatcaaa    2760
tggatttagt tgaagattgc aatacatttc tgtcttttgt agctgataaa actttagaaa    2820
aacagaaatt atataaagct aattcttgta aaaatcgatt ttgtcctgtc tgtgcttgga    2880
gaaaagctag aaaagatgca ttgggtttat ctttgatgat gcaatatatt aagcagcaag    2940
agaaaaagga gtttatcttt ttaactttga ctacacctaa tgtaatgagt gatgaattag    3000
aaaatgaaat aaaacgttat aataattctt ttagaaaact tataaagaga aaaaagtag     3060
gtagtgttat aaagggatat gttcgtaagt tagagattac atataataaa aaaagagatg    3120
attataatcc tcattttcat gtgttaattg cagtaaataa atcgtatttc acagataaaa    3180
gatattatat tagccaacaa gaatggttag atttatggcg tgatgtaacg ggcatttcag    3240
aaataacaca agttcaagtt caaaaaataa gacaaaataa taataaagaa ttatatgaaa    3300
tggctaagta ttctggtaaa gatagtgatt atttaataaa tcaaaaagtc tttgatgcat    3360
tttataaatc acttaaaggt aaacaggtat tagtttattc aggattattt aaagaggcta    3420
aaaagaaatt aaaaaatggg gatttagatt acttaaaaga aattgatcca accgaatata    3480
tctatcaaat ttttttatatt tggaaacaaa aagagtattt agctagtgaa ctttatgact    3540
taacagaaca agaaaaaaga gaaattaatc acaaaatgat agacgaaatc gaggaagaac    3600
aataacaaaa tataagtgct aacagtcgtc tgcaagttta gttaagggtt cttctcaacg    3660
cacaataaat tttctcggca taaatgcgtg gtctaattt tattttaat aaccttgata    3720
gcaaaaaatg ccattccaat acaaaaccac atacctataa tcgataacca cataacagtc    3780
ataaaaccac tcctttttaa caaactttat cacaagaaat attttggcat tctacgacta    3840
taacttaaat ttatatttt tactttataa tatataattg attatagaat aatgttgctc    3900
atatcgtttg ccaacatcta gtactcaaat tacactatgt tacacttggt aatattaacc    3960
gaacttcccc tgtccaaatt agataagagg taataataaa tggaaaataa ttttatagta    4020
aatgaaaatg agaagcgtgt attaaaacaa atttccaata acagcaatat ttcacgaaca    4080
caaatatcga agaatttaga acttaataaa gctactattt ctaacattct gaacaactta    4140
aaacacaaga gtttagttaa tgaagtagga gaaggtaata gtactaaaag tggtggacga    4200
aagcctattt tactcgaaat taaccaaaaa tatggctact atatttctat ggatttaaca    4260
tatgattccg ttgaattaat gtacaactac tttgatgcta ctatattaaa gcaagattcc    4320
tacgaattaa atgataaaaa tgtaagcagt atattacaaa ttttaaaatc taatataaac    4380
gtctcagaaa aatatgatac gttatatggg ttacttggta tatctatatc catacacggt    4440
atcgttgacg atgagcaaaa cataatcaat cttccttttc ataaaaatga gaaacgcaca    4500
tttaccgatg aattaaagtc attcacaaat gttcctgtcg ttatagaaaa tgaagcaaat    4560
ttatcagcgc tatatgaaaa aagtttatat attaattcaa acataaataa tttgattact    4620
ttaagtattc acaagggtat aggcgctggc atcctaataa ataaaaaact ttatcgtggc    4680
tcaaatggag aggctggaga gataggtaag acattggttt tggaatctat aaataacaat    4740
gacaacaaat attataaaat cgaagatata tgctcccaag acgctttaat acagaaaata    4800
aataataggt tgggcgtcac attgacgttt acagaactaa tccaatatta caacgaagga    4860
aattcaattg ttgctcatga aattaaacaa tttattaata aaatgacagt tctgattcat    4920
aatttgaata cacaatttaa cccagacgct atttatatta actgtccttt aattaatgaa    4980
ttaccaaata tttttaaatga aattaaagag caattctcct gttttttctca aggcagtcca    5040
gttcaattac atttaactac taatgtaaaa caagctactt tattgggtgg cactttagca    5100
```

```
ataatgcaaa aaacattaaa tataaataac attcaaatga atattaaata attacagcag    5160
tctgagttat aaaatagata tctcggaccg tcataaaaaa tttatttgct ttcaggaaaa    5220
tttttctgta taatagattc aagttagttt gtttattaaa ttaaccaact aaaatgtaga    5280
attcgagctc ggtacccggg gatcctctag agtcgacctg cagccaagct tgggcttttc    5340
agcctgatac agattaaatc agaacgcaga agcggtctga taaaacagaa tttgcctggc    5400
ggcagtagcg cggtggtccc acctgacccc atgccgaact cagaagtgaa acgccgtagc    5460
gccgatggta gtgtggggtc tccccatgcg agagtaggga actgccaggc atcaaataaa    5520
acgaaaggct cagtcgaaag actgggcctt tcgttttatc tgttgtttgt cggtgaacgc    5580
tctcctgagt aggacaaatc cgccgggagc ggatttgaac gttgcgaagc aacggcccgg    5640
agggtggcgg gcaggacgcc cgccataaac tgccaggcat caaattaagc agaaggccat    5700
cctgacggat ggcctttttg cgtttctaca aactcttttg tttattttc taaatacatt    5760 caaatatgta tccgctcatc cccatcctat cgatgataag ctgtcaaaca tgagaattaa    5820
atcaatctaa agtatatatg agtaaacttg gtctgacagt taccaatgct taatcagtga    5880
ggcacctatc tcagcgatct gtctatttcg ttcatccata gttgcctgac tccccgtcgt    5940
gtagataact acgatacggg agggcttacc atctggcccc agtgctgcaa tgataccgcg    6000
agacccacgc tcaccggctc cagatttatc agcaataaac cagccagccg aagggccga    6060 gcgcagaagt ggtcctgcaa cttatccgc ctccatccag tctattaatt gttgccggga    6120
agctagagta gtagttcgc cagttaatag tttgcgcaac gttgttgcca ttgctacagg    6180
catcgtggtg tcacgctcgt cgtttggtat ggcttcattc agctccggtt cccaacgatc    6240
aaggcgagtt acatgatccc ccatgttgtg caaaaaagcg gttagctcct tcggtcctcc    6300
gatcgttgtc agaagtaagt tggccgcagt gttatcactc atggttatgg cagcactgca    6360
taattctctt actgtcatgc catccgtaag atgcttttct gtgactggtg agtactcaac    6420
caagtcattc tgagaatagt gtatgcggcg accgagttgc tcttgcccgg cgtcaacacg    6480
ggataatacc gcgccacata gcagaacttt aaaagtgctc atcattggaa acgctcttc    6540 ggggcgaaaa ctctcaagga tcttaccgct gttgagatcc agttcgatgt aacccactcg    6600
tgcacccaac tgatcttcag catcttttac tttcaccagc gtttctgggt gagcaaaaac    6660
aggaaggcaa aatgccgcaa aaaagggaat aagggcgaca cggaaatgtt gaatactcat    6720
actcttcctt tttcaatatt attgaagcat ttatcagggt tattgtctca tgagcggata    6780
catatttgaa tgtatttaga aaaataaaca ataggggtt ccgcgcacat ttccccgaaa    6840
agtgccacct                                                          6850
```

<210> SEQ ID NO 101
<211> LENGTH: 6850
<212> TYPE: DNA
<213> ORGANISM: Artificial Sequence
<220> FEATURE:
<223> OTHER INFORMATION: Synthetic sequence

<400> SEQUENCE: 101

```
ggcggccgca ctggcttact atgttggcac tgatgagggt gtcagtgaag tgcttcatgt     60
ggcaggagaa aaaaggctgc accggtgcgt cagcagaata tgtgatacag gatatattcc    120
gcttcctcgc tcactgactc gctacgctcg gtcgttcgac tgcggcgagc ggaaatggct    180
tacgaacggg gcggagattt cctggaagat gccaggaaga tacttaacag ggaagtgaga    240
```

-continued

```
gggccgcggc aaagccgttt ttccataggc tccgccccccc tgacaagcat cacgaaatct    300
gacgctcaaa tcagtggtgg cgaaacccga caggactata aagataccag gcgtttcccc    360
ctggcggctc cctcgtgcgc tctcctgttc ctgcctttcg gtttaccggt gtcattccgc    420
tgttatggcc gcgtttgtct cattccacgc ctgacactca gttccgggta ggcagttcgc    480
tccaagctgg actgtatgca cgaaccccccc gttcagtccg accgctgcgc cttatccggt    540
aactatcgtc ttgagtccaa cccggaaaga catgcaaaag caccactggc agcagccact    600
ggtaattgat ttagaggagt tagtcttgaa gtcatgcgcc ggttaaggct aaactgaaag    660
gacaagtttt ggtgactgcg ctcctccaag ccagttacct cggttcaaag agttggtagc    720
tcagagaacc ttcgaaaaac cgccctgcaa ggcggttttt tcgttttcag agcaagagat    780
tacgcgcaga ccaaaacgat ctcaagaaga tcatcttatg cggccgcttc tttcctgcgt    840
tatcccctga ttctgtggat aaccgtatta ccgcctttga gtgagctgat accgctcgcc    900
gcagccgaac gaccgagcgc agcgagtcag tgagcgagga agcggaagag cgcctgatgc    960
ggtattttct ccttacgcat ctgtgcggta tttcacaccg cataggaaga tccctcgacc   1020
tgcaggcatg caagcttctg taggttttta ggcataaaac tatatgattt acccctaaat   1080
ctttaaaatg ccccttaaaa ttcaaaataa aggcatttaa aatttaaata tttcttgtga   1140
taaagtttgt taaaaggag tggttttatg actgttatgt ggttatcgat tataggtatg   1200
tggttttgta ttggaatggc atttttttgct atcaaggtta ttaaaaataa aaattagacc   1260
acgcatttat gccgagaaaa tttattgtgc gttgagaaga acccttaact aaacttgcag   1320
acgaatgtcg gcatagcgtg agctattaag ccgaccattc gacaagtttt gggattgtta   1380
agggttccga ggctcaacgt caataaagca attggaataa agaagcgaaa aaggagaagt   1440
cggttcagaa aaagaagcat atgcatctgg agctgtaata taaaaaccttt cttcaactaa   1500
cggggcaggt tagtgacatt agaaaaccga ctgtaaaaag tacagtcggc attatctcat   1560
attataaaag ccagtcatta ggcctatctg acaattcctg aatagagttc ataaacaatc   1620
ctgcatgata accatcacaa acagaatgat gtacctgtaa agatagcggt aaatatattg   1680
aattaccttt attaatgaat tttcctgctg taataatggg tagaaggtaa ttactattat   1740
tattgatatt taagttaaac ccagtaaatg aagtccatgg aataatagaa agagaaaaag   1800
cattttcagg tataggtgtt ttgggaaaca atttccccga accattatat ttctctacat   1860
cagaaaggta taaatcataa aactctttga agtcattctt tacaggagtc caaataccag   1920
agaatgtttt agatacacca tcaaaaattg tataaagtgg ctctaactta tcccaataac   1980
ctaactctcc gtcgctattg taaccagttc taaaagctgt atttgagttt atcacccttg   2040
tcactaagaa aataaatgca gggtaaaatt tatatccttc ttgttttatg tttcggtata   2100
aaacactaat atcaatttct gtggttatac taaaagtcgt ttgttggttc aaataatgat   2160
taaatatctc ttttctcttc caattgtcta aatcaatttt attaaagttc atttgatatg   2220
cctcctaaat ttttatctaa agtgaattta ggaggcttac ttgtctgctt tcttcattag   2280
aatcaatcct tttttaaaag tcaatattac tgtaacataa atatatattt taaaaatatc   2340
ccactttatc caattttcgt ttgttgaact aatgggtgct ttagttgaag aataaaagac   2400
cacattaaaa aatgtggtct tttgtgtttt tttaaaggat ttgagcgtag cgaaaaatcc   2460
ttttctttct tatcttgata ataagggtaa ctattgccgg cgaggctagt tacccttaag   2520
ttattggtat gactggtttt aagcgcaaaa aaagttgctt tttcgtacct attaatgtat   2580
cgttttaaat gaatagtaaa aaacatacat agaaagggga aaaagcaact ttttttattg   2640
```

```
tcatagtttg tgaaaactaa gttgttttta tgtgttataa catggaaaag tatactgaga    2700
aaaaacaaag aaatcaagta tttcagaaat ttattaaacg tcatattgga gagaatcaaa    2760
tggatttagt tgaagattgc aatacatttc tgtcttttgt agctgataaa actttagaaa    2820
aacagaaatt atataaagct aattcttgta aaaatcgatt ttgtcctgtc tgtgcttgga    2880
gaaaagctag aaaagatgca ttgggtttat ctttgatgat gcaatatatt aagcagcaag    2940
agaaaaagga gtttatcttt ttaactttga ctacacctaa tgtaatgagt gatgaattag    3000
aaaatgaaat aaaacgttat aataattctt ttagaaaact tataaagaga aaaaaagtag    3060
gtagtgttat aaagggatat gttcgtaagt tagagattac atataataaa aaagagatg     3120
attataatcc tcattttcat gtgttaattg cagtaaataa atcgtatttc acagataaaa    3180
gatattatat tagccaacaa gaatggttag atttatggcg tgatgtaacg ggcatttcag    3240
aaataacaca agttcaagtt caaaaaataa gacaaaataa taataaagaa ttatatgaaa    3300
tggctaagta ttctggtaaa gatagtgatt atttaataaa tcaaaaagtc tttgatgcat    3360
tttataaatc acttaaaggt aaacaggtat tagtttattc aggattattt aaagaggcta    3420
aaaagaaatt aaaaaatggg gatttagatt acttaaaaga aattgatcca accgaatata    3480
tctatcaaat tttttatatt tggaaacaaa aagagtattt agctagtgaa ctttatgact    3540
taacagaaca agaaaaaaga gaaattaatc acaaaatgat agacgaaatc gaggaagaac    3600
aataacaaaa tataagtgct aacagtcgtc tgcaagttta gttaagggtt cttctcaacg    3660
cacaataaat tttctcggca taaatgcgtg gtctaatttt tatttttaat aaccttgata    3720
gcaaaaaatg ccattccaat acaaaaccac atacctataa tcgataacca cataacagtc    3780
ataaaaccac tccttttttaa caaactttat cacaagaaat attttggcat tctacgacta    3840
taacttaaat ttatattttt tacttttataa tatataattg attatagaat aatgttgctc    3900
atatcgtttg ccaacatcta gtactcaaat tacactatgt tacacttggt aatattaacc    3960
gaacttcccc tgtccaaatt agataagagg taataataaa tggaaaataa ttttatagta    4020
aatgaaaatg agaagcgtgt attaaaacaa attttcaata acagcaatat ttcacgaaca    4080
caaatatcga agaatttaga acttaataaa gctactattt ctaacattct gaacaactta    4140
aaacacaaga gtttagttaa tgaagtagga gaaggtaata gtactaaaag tggtggacga    4200
aagcctattt tactcgaaat taaccaaaaa tatggctact atatttctat ggatttaaca    4260
tatgattccg ttgaattaat gtacaactac tttgatgcta ctatattaaa gcaagattcc    4320
tacgaattaa atgataaaaa tgtaagcagt atattacaaa ttttaaaatc taatataaac    4380
gtctcagaaa aatatgatac gttatatggg ttacttggta tatctatatc catacacggt    4440
atcgttgacg atgagcaaaa cataatcaat cttccttttc ataaaaatga gaaacgcaca    4500
tttaccgatg aattaaagtc attcacaaat gttcctgtcg ttatagaaaa tgaagcaaat    4560
ttatcagcgc tatatgaaaa aagtttatat attaattcaa acataaataa tttgattact    4620
ttaagtattc acaagggtat aggcgctggc atcctaataa ataaaaaact ttatcgtggc    4680
tcaaatggag aggctggaga gataggtaag acattggttt tggaatctat aaataacaat    4740
gacaacaaat attataaaat cgaagatata tgctcccaag acgctttaat acagaaaata    4800
aataataggt tgggcgtcac attgacgttt acagaactaa tccaatatta caacgaagga    4860
aattcaattg ttgctcatga aattaaacaa tttattaata aaatgacagt tctgattcat    4920
aatttgaata cacaatttaa cccagacgct atttatatta actgtccttt aattaatgaa    4980
```

```
ttaccaaata ttttaaatga aattaaagag caattctcct gttttcctca aggcagtcca    5040
gttcaattac atttaactac taatgtaaaa caagctactt tattgggtgg cactttagca    5100
ataatgcaaa aacattaaa tataaataac attcaaatga atattaaata attacagcag     5160
tctgagttat aaaatagata tctcggaccg tcataaaaaa tttatttgct ttcaggaaaa    5220
tttttctgta taatagattc aagttagttt gtttattaaa ttaaccaact aaaatgtaga    5280
attcgagctc ggtacccggg gatcctctag agtcgacctg cagccaagct tgggcttttc    5340
agcctgatac agattaaatc agaacgcaga agcggtctga taaaacagaa tttgcctggc    5400
ggcagtagcg cggtggtccc acctgacccc atgccgaact cagaagtgaa acgccgtagc    5460
gccgatggta gtgtggggtc tccccatgcg agagtaggga actgccaggc atcaaataaa    5520
acgaaaggct cagtcgaaag actgggcctt tcgttttatc tgttgtttgt cggtgaacgc    5580
tctcctgagt aggacaaatc cgccgggagc ggatttgaac gttgcgaagc aacggcccgg    5640
agggtggcgg gcaggacgcc cgccataaac tgccaggcat caaattaagc agaaggccat    5700
cctgacggat ggcctttttg cgtttctaca actcttttg tttattttc taaatacatt      5760
caaatatgta tccgctcatg cccatcgtat cgatgataag ctgtcaaaca tgagaattaa    5820
atcaatctaa agtatatatg agtaaacttg gtctgacagt taccaatgct taatcagtga    5880
ggcacctatc tcagcgatct gtctatttcg ttcatccata gttgcctgac tccccgtcgt    5940
gtagataact acgatacggg agggcttacc atctggcccc agtgctgcaa tgataccgcg    6000
agacccacgc tcaccggctc cagatttatc agcaataaac cagccagccg aagggccga    6060
gcgcagaagt ggtcctgcaa ctttatccgc ctccatccag tctattaatt gttgccggga    6120
agctagagta agtagttcgc cagttaatag tttgcgcaac gttgttgcca ttgctactgg    6180
catcgtagtg tcacgctcgt cgtttggtat ggcttcattc agctccggtt cccaacgatc    6240
aaggcgagtt acatgatccc ccatgttgtg caaaaaagcg gttagctcct tcggtcctcc    6300
gatcgttgtc agaagtaagt tggccgcagt gttatcactc atggttatgg cagcactgca    6360
taattctctt actgtcatgc catccgtaag atgcttttct gtgactggtg agtactcaac    6420
caagtcattc tgagaatagt gtatgcggcg accgagttgc tcttgcccgg cgtcaacacg    6480
ggataatacc gcgccacata gcagaacttt aaaagtgctc atcattggaa aacgctcttc    6540
ggggcgaaaa ctctcaagga tcttaccgct gttgagatcc agttcgatgt aacccactcg    6600
tgcacccaac tgatcttcag catctttac tttcaccagc gtttctgggt gagcaaaaac      6660
aggaaggcaa aatgccgcaa aaagggaat aaggcgaca cggaaatgtt gaatactcat       6720
actcttcctt tttcaatatt attgaagcat ttatcagggt tattgtctca tgagcggata    6780
catatttgaa tgtatttaga aaaataaaca ataggggtt ccgcgcacat ttccccgaaa      6840
agtgccacct                                                            6850
```

<210> SEQ ID NO 102
<211> LENGTH: 9
<212> TYPE: PRT
<213> ORGANISM: Artificial Sequence
<220> FEATURE:
<223> OTHER INFORMATION: Synthetic sequence

<400> SEQUENCE: 102

Arg Asp Thr Thr Met Pro Val Ala Met
1               5

<210> SEQ ID NO 103

<211> LENGTH: 56
<212> TYPE: DNA
<213> ORGANISM: Escherichia coli

<400> SEQUENCE: 103
accgaaccga cctggttccc ggatagccag aacctggcat ttacttctga ccaggc    56

<210> SEQ ID NO 104
<211> LENGTH: 56
<212> TYPE: DNA
<213> ORGANISM: Escherichia coli

<400> SEQUENCE: 104
attgaattga tytggttttt ggatagttag aatytggtat ttattttga tyaggt    56

<210> SEQ ID NO 105
<211> LENGTH: 56
<212> TYPE: DNA
<213> ORGANISM: Escherichia coli

<400> SEQUENCE: 105
attgaattga tctggttttt ggatagttag aatctggtat ttattttga tcaggt    56

<210> SEQ ID NO 106
<211> LENGTH: 56
<212> TYPE: DNA
<213> ORGANISM: Escherichia coli

<400> SEQUENCE: 106
aaccgacctg gttcccggat agccagaacc tggcatttac ttctgaccag gccggt    56

<210> SEQ ID NO 107
<211> LENGTH: 56
<212> TYPE: DNA
<213> ORGANISM: Escherichia coli

<400> SEQUENCE: 107
aaccgacctg gttcccggat agccagaacc tggcatttac ttctgaccag gccggt    56

<210> SEQ ID NO 108
<211> LENGTH: 56
<212> TYPE: DNA
<213> ORGANISM: Escherichia coli

<400> SEQUENCE: 108
aattgatctg gttttggat agttagaatc tggtatttat ttttgatcag gttggt    56

<210> SEQ ID NO 109
<211> LENGTH: 56
<212> TYPE: DNA
<213> ORGANISM: Escherichia coli

<400> SEQUENCE: 109
aattgatttg gttttggat agttagaatt tggtatttat ttttgattag gttggt    56

MINICIRCLE PRODUCING BACTERIA ENGINEERED TO DIFFERENTIALLY METHYLATE NUCLEIC ACID MOLECULES THEREIN

STATEMENT OF RIGHTS TO INVENTIONS MADE UNDER FEDERALLY SPONSORED RESEARCH

This invention was made with government support under DE027850 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is txt 360056 489USPC CORRECTED SEQUENCE LISTING.txt. The text file is 67.3 KB, was created on Aug. 17, 2021, and is being submitted electronically via EFS-Web.

BACKGROUND

Technical Field

The present disclosure relates generally to engineered, minicircle-producing bacteria that differentially methylate DNA therein, and methods of using these bacteria for producing minicircle DNA and for increasing the transformation efficiency of exogenous DNA when transformed into bacteria, as well as kits for use in such methods.

Description of the Related Art

Genetic engineering is a powerful approach for harnessing bacterial abilities and for discovering fundamental aspects of bacterial function. In recent years, the genetic toolkit at the disposal of researchers has massively expanded. The application of these tools is largely limited to bacterial strains with high transformation efficiency. However, relative to the wealth and diversity of known bacterial species, there are currently only a small number of such highly genetically tractable strains. A strain that is not amenable to alterations of its genome or to the introduction of new genetic information during genetic engineering is termed genetically intractable.

At present, genetic intractability is a pervasive and widespread problem across all fields of microbiology; most bacteria that can be grown in a laboratory remain beyond the power of genetics for elucidating function or engineering for human use. Even within species that are genetically tractable, this tractability is often restricted to a small number of domesticated strains, while new primary isolates of the species with disparate phenotypic traits of interest are either poorly tractable or currently intractable. As a result, researchers have had to engage in expensive generation of ad hoc genetic systems for each distinct species, often with further laborious modifications for each distinct wild strain isolate.

In their natural environment, bacteria acquire new genetic information through horizontal gene transfer (HGT) by three distinct means: conjugation, transduction, and transformation. During conjugation, DNA is transferred from one organism to another by direct cell-to-cell contact. During transduction DNA is carried by bacteriophages, viruses that invade by injecting DNA into host bacterial cells. These two natural processes involve multifaceted interactions requiring complex machinery and therefore are of limited value in modern bacterial genetics where DNA should ideally be easily and rapidly transferable into any given bacterial strain. During transformation however, naked DNA is directly acquired and incorporated into the host genome by recombination with homologous sequences or, in the case of plasmids, by establishing a new episome (extra-chromosomal DNA that replicates autonomously), resulting in genetic alteration of the cell. Genetic competence is the cellular state that enables bacteria to undergo natural transformation, a transient 'window of opportunity' for DNA internalization. However, while there are over 6,600 validated cultured type strains of bacterial species, and approximately 30,000 formally named species that are in pure culture, natural transformation and competence has been observed in only a small handful, approximately 80 bacterial species. This may even be an overestimation, as in several cases only a single report documents transformation and molecular evidence of natural transformation is lacking. For the remaining cultivated bacterial species that are of interest, microbiologists must instead develop 'artificial' transformation and individualized genetic systems, often at the strain level: a process continually stymied by genetically intractable phenotypes.

Accordingly, the known methods fall far short of being facile and rapidly application to a wide diversity of bacteria. Improved methods for overcoming barriers in genetic engineering of intractable bacteria are needed.

BRIEF SUMMARY

As described further below, provided herein is an engineered, minicircle (MC)-producing bacterium that is deficient in an endogenous methyltransferase and thereby has reduced DNA-methylation capability. Such bacteria produce differentially methylated (e.g., methylation-free) MC DNA that can then be transformed into other bacteria, e.g., intractable bacteria.

More specifically, the present disclosure features engineered, (MC)-producing *Escherichia coli* that differentially methylate DNA therein, as well as methods of using these bacteria for producing MC DNA and for increasing the transformation efficiency of exogenous DNA when transformed into bacteria, including intractable bacteria.

Accordingly, aspects of the present disclosure include an engineered bacterium comprising a parental plasmid that comprises a minicircle nucleic acid sequence comprising an exogenous nucleic acid sequence, wherein the engineered bacterium is deficient in at least one endogenous methyltransferase such that the engineered bacterium has reduced DNA-methylation capability.

Additional aspects of the disclosure include a kit comprising an engineered bacterium described herein. In another aspect, described herein is a minicircle (MC) plasmid produced from an engineered bacterium or a kit described herein.

Further aspects of the disclosure include a method, comprising:

producing a minicircle comprising an exogenous DNA sequence in a first bacterium that is an engineered bacterium as described herein; and transforming the minicircle into a second bacterium, the minicircle resisting degradation when transformed into the second bacterium.

Additionally, aspects of the present disclosure include an engineered bacterium comprising: a minicircle plasmid comprising an exogenous nucleic acid sequence, wherein the engineered bacterium is deficient in at least one endogenous methyltransferase such that the engineered bacterium has reduced DNA-methylation capability.

The present disclosure further describes a host cell, comprising: a plasmid comprising a nucleic acid sequence that is exogenous to the host cell, wherein the exogenous nucleic acid sequence lacks methylation at a plurality of methylation cites that would be methylated in a reference *Escherichia coli* bacterium.

In further aspects, the present disclosure describes a method, comprising: transforming a parental plasmid into an engineered bacterium that is deficient in at least one endogenous methyltransferase, the parental plasmid comprising a minicircle nucleic acid sequence comprising an exogenous nucleic acid sequence; and producing a minicircle comprising the minicircle nucleic acid sequence.

BRIEF DESCRIPTION OF THE DRAWINGS

The sizes and relative positions of elements in the figures are not necessarily drawn to scale. For example, the shapes of various elements and angles are not drawn to scale and some of these elements are arbitrarily enlarged and positioned to improve figure legibility. Further, the particular shapes of the elements as drawn, are not intended to convey any information regarding the actual shape of the particular elements, and have been solely selected for ease of recognition in the figures.

FIG. 1A. Identification of RM system target motifs by SMRTseq. Methylome analysis of polymerase kinetics during sequencing permits detection of methylated sites at single-nucleotide resolution across the genome, revealing the exact motifs targeted by innate RM systems (indicated by underlined nucleotides, N is any nucleotide) (Kinetic trace image adapted from world wide website of PACBIO®).

FIG. 1B. Assembly in silico of a genetic tool with a desired functionality, followed by screening for the presence of RM target sequences and sequence adaptation, using SNPs or synonymous codon substitutions in coding regions, to create an RM-silent template which is synthetized de novo to assemble a SyngenicDNA tool.

FIG. 1C. Artificial transformation of the target bacterium. Inappropriately methylated target motifs of the original genetic tool are recognized as nonself-DNA and degraded by RM systems. In contrast, the SyngenicDNA variant retains the form and functionality of the genetic tool, but is uniquely designed at the nucleotide level to evade the RM systems and can operate as desired within the target bacterial host.

FIG. 2A. JE2 maintains two Type I RM systems and a Type IV restriction system. Restriction endonucleases (HsdR and SauUSI), methyltransferase (HsdM) genes, and specificity subunit (HsdS) genes are shown. RM system operons and their corresponding target motifs were identified by SMRTseq and REBASE analysis.

FIG. 2B. Construction of pEPSA5SynJE2, which is an RM-silent variant of the pEPSA5 plasmid tailored to JE2. Six nucleotide substitutions (two synonymous codon substitutions and four SNPs) eliminated all Type I RM system targets from pEPSA5 sequence.

FIG. 2C. Plasmid propagation scheme. *E. coli* host strains produce DNA susceptible (DH5a; Dcm+) or resistant (*E. coli* ER2796; Dcm−) to the *S. aureus* JE2 Type IV restriction system.

FIG. 2D. Comparison of plasmid transformation efficiency (CFU/µg DNA) with pEPSA5 and the SyngenicDNA-variant pEPSA5SynJE2.

FIGS. 3A-3C show the SyngenicDNA Minicircle (MC) Plasmid (SyMPL) approach applied to *S. aureus* JE2.

FIG. 3A. Propagation of MCs (pEPSA5MC and pEPSA5SynJE2MC) lacking Dcm-methylated sites within SyMPL producer strain *E. coli* JMC1.

FIG. 3B. Comparison of SyngenicDNA and pEPSA5-based SyMPL plasmid transformation efficiency (CFU/µg DNA) with JE2. Data are means+SEM from nine independent experiments (three biological replicates with three technical replicates each).

FIG. 3C. Secondary analysis of SyngenicDNA and pEPSA5-based SyMPL plasmid transformation efficiencies in CFU/pmol DNA. Data are means+SEM from nine independent experiments (three biological replicates with three technical replicates each).

FIG. 4A. Current MC strategies (Kay, et al., (2010) *Nat Biotechnol* 28(12):1287-1289) are applied to produce small circular expression cassettes for stable transgene expression in eukaryote hosts. Typically, a transgene cassette containing a eukaryote promoter, transgene, and polyA tail is attached to an *E. coli* plasmid backbone within a multiple cloning site flanked by attB and attP sites (bacterial and phage attachment recognition sites of the φC31 integrase enzyme, illustrated as circles) to form a parent plasmid (PP). The *E. coli* backbone also contains the antibiotic-selection marker Kan$^R$, a pUC origin for high-copy-number autonomous replication in *E. coli*, and 32× tandem repeats of the I-SceI homing endonuclease recognition site for I-SceI targeted degradation after MC induction. The φC31 integrase and I-SceI enzymes are arabinose inducible and encoded on the chromosome of *E. coli* 10 ZYCY10P3S2T ((Kay, et al., (2010) *Nat Biotechnol* 28(12):1287-1289)).

FIG. 4B. In the repurposed bacterial MC strategy, a functional bacterial replicon/genetic tool takes the place of the eukaryotic transgene cassette. This allows for high-yield production of minimalistic genetic tools, which lack an *E. coli* replicon, for application in bacteria other than *E. coli*. The *S. aureus* replicon of the pEPSA5 plasmid was used to form a pEPSA5 MC that is 38% smaller than pEPSA5.

FIG. 4C. Restriction enzyme digestion of pEPSA5 PP and pEPSA5 MC following isolation from *E. coli* MC (ZYCY10P3S2T, a MC-producing strain). Plasmid DNA (500 ng), isolated prior to arabinose induction (PP) or 4-hours post induction (MC), was linearized with 1 U of the unique cutter HindIII for 1 hour and resolved on a 1% agarose gel. Lane M, marker DNA (1 kb Ladder; NEB); lane PP, uninduced pEPSA5PP; lane MC, induced pEPSA5MC.

FIGS. 5A-5C show the methylation signatures present on *E. coli* MC (ZYCY10P3S2T) genomic DNA and the organization of responsible methyltransferase gene clusters.

FIG. 5A. Detailed summary of 6-methyladenine (n$^6$A)-modified motifs across the genome of *E. coli* MC (ZYCY10P3S2T, a MC-producing strain) detected by SMRTseq and Basemod analysis (the PacBio DNA modification sequence analysis pipeline, at the website of PACBIO®). RM systems were designated as Type I or II based on gene characterization through REBASE. The modified base within each motif is bolded while the modified base in the complementary strand is italicized. The total number includes motifs occurring on the "+" and "−" strands.

FIG. 5B. Summary of 5-methylcytosine (m$^5$C) CCWGG-modified motifs on the *E. coli* MC genome. Sequence comparison and alignment of *E. coli* MC genomic region before and after bisulfite conversion. Unmethylated cytosine residues converted to thymine during bisulfite treatment are indicated by white arrows; m$^5$C methylated cytosines protected from deamination are indicated by black arrows (present within CCWGG motifs, where W=A or T, but not CCCGG motifs).

FIG. 5C. A schematic representation showing the structure and genomic context of *E. coli* MC RM systems and orphan methyltransferases. Gene assignments, nomenclature and genome coordinates publicly available at REBASE.

FIG. 6A. The original dual plasmid (pCas and pTarget) CRISPR-Cas9/λ-Red system developed by Jiang, et al. ((2015) *Appl Environ Microbiol* 81(7):2506-2514), with an arabinose inducible regulatory promoter/repressor module (araC-Pbad) controlling the λ-Red system (Gam, Beta, Exo).

FIG. 6B. Construction of the pCasTet-λ plasmid, a modified version of pCas. An 818-bp tetracycline-inducible regulatory promoter/repressor unit, TetR/Ptet0, was amplified from pCKTRBS and spliced to a linear amplicon of pCas lacking the araC-Pbad module. The resultant plasmid, pCasTet-λ, contains λ-Red genes under transcriptional control of the TetR/PtetO regulatory cassette and can be used in combination with the original pTarget.

FIG. 6C. Assembly of DNA editing templates for methyltransferase gene recombineering in *E. coli* MC. Approximately a 400-bp region from 5' and 3' of each 40 methyltransferase gene were spliced together onto a pRRS plasmid backbone to form the methyltransferase deletion template plasmids (pRRSDcmET, pRRSHsdET, and 41 pRRSDamET; where ET is editing template). These plasmids were used to amplify each methyltransferase editing template prior to λ-Red recombineering.

FIGS. 8A-8F provide schematic representations showing the context of genome editing in *E. coli* JMC-series strains along with phenotypic confirmation of methyltransferase deficiencies.

FIG. 8A. Sequence confirmed Dcm deletion in *E. coli* JMC1.

FIG. 8B. Comparison of Dcm activity in *E. coli* MC and *E. coli* JMC1 strains. Alignment of genomic regions before and after bisulfite conversion, highlighting the absence of $^{m5}$C-modified CCWGG motifs on *E. coli* JMC1 gDNA (where W is A or T). White arrows indicate unmethylated cytosine residues converted to thymine during bisulfite treatment. Black arrows indicate in $^5$C methylated cytosines protected from deamination.

FIG. 8C. Sequence confirmed Hsd deletion in *E. coli* JMC2.

FIG. 8D. SMRTseq/Base mod summary of modified $^{m6}$A motifs across the *E. coli* JMC2 genome, demonstrating the absence of methylated HsdS motifs (compared to the *E. coli* MC strain shown in FIG. 2A).

FIG. 8E. Sequence confirmed dam deletion in *E. coli* JMC3.

FIG. 8F. DpnI restriction of gDNA isolated from *E. coli* strains MC, JMC1, JMC2 and JMC3. Genomic DNA from the methyl-deficient *E. coli* ER2796 (NEB) is included as control. DpnI is a methyl-directed endonuclease that requires Gm$^6$ATC for activity. JMC3 gDNA is resistant to DpnI cleavage indicating it is unmethylated at Dam (GATC) sites.

FIG. 9A. provide a schematic diagram showing the original pEPSA5 *S. aureus-E. coli* shuttle vector (Forsyth R A, et al. (2002) *Mol Microbiol* 43(6):1387-1400). This plasmid contains 11 individual *S. aureus* JE2 RM target motifs (Type I; n=3, and Type IV; n=8) that will be recognized and targeted for degradation upon transformation.

FIG. 9B pEPSA5SynJE2 was assembled by replacing a 3-kbp fragment of pEPSA5 that contained three JE2 RM target motifs with a de novo synthesized RM-silent fragment. Black arrows indicate JE2 RM target motifs. Arrows indicate those modified sites on the RM-silent fragment. Underlined letters indicate modified nucleotides. Type IV system targets are not shown, as these can be eliminated by propagation in a Dcm-deficient *E. coli* host. Both plasmids are 6850 bp in length and differed by only six nucleotides (99.91% nucleotide identity).

FIGS. 10A-10B show Assembly and propagation of pEPSA5- and pEPSA5Syn-based MCs in *E. coli* JMC1.

FIG. 10A. The *S. aureus* functional replicon of pEPSA5, containing a single JE2 RM system target, was amplified to remove the original *E. coli* replicon. The *S. aureus* replicon was spliced to the pMC plasmid to form the pEPSA5 parental plasmid, which was transformed into competent *E. coli* JMC1 cells followed by arabinose induction of MC assembly. pEPSA5MC has a single JE2 RM system target.

FIG. 10B. This process was repeated for pEPSA5SynJE2, which is RM-silent with respect to JE2. pEPSA5MC and pEPSA5SynJE2MC plasmids differ by only the two nucleotides, which are underlined.

FIG. 12 shows the annotated coding sequence of the *E. coli* HsdM methyltransferase, where the PAM sites, PAM sites with increased efficiency, the gRNA protospacer target sequences are indicated. The *E. coli* HsdM protein in UniProtKB is B1VCK6 (B1VCK6 ECOLX) and the HsdM gene is Gene ID: 6276026.

FIG. 13 shows the annotated coding sequence of the *E. coli* Dcm methyltransferase, where the PAM sites, PAM sites with increased efficiency, the gRNA protospacer target sequences are indicated. The *E. coli* Dcm protein in UniProtKB is POAED9 (DCM ECOLI) and the Dcm gene is Gene ID: 946479.

FIG. 14 shows the annotated coding sequence of the *E. coli* dam methyltransferase, where the PAM sites, PAM sites with increased efficiency, the gRNA protospacer target sequences are indicated. The *E. coli* Dcm protein in UniProtKB is POAEE8 (DMA ECOLI) and the dam gene is Gene ID: 947893.

DETAILED DESCRIPTION

Figure 1A:
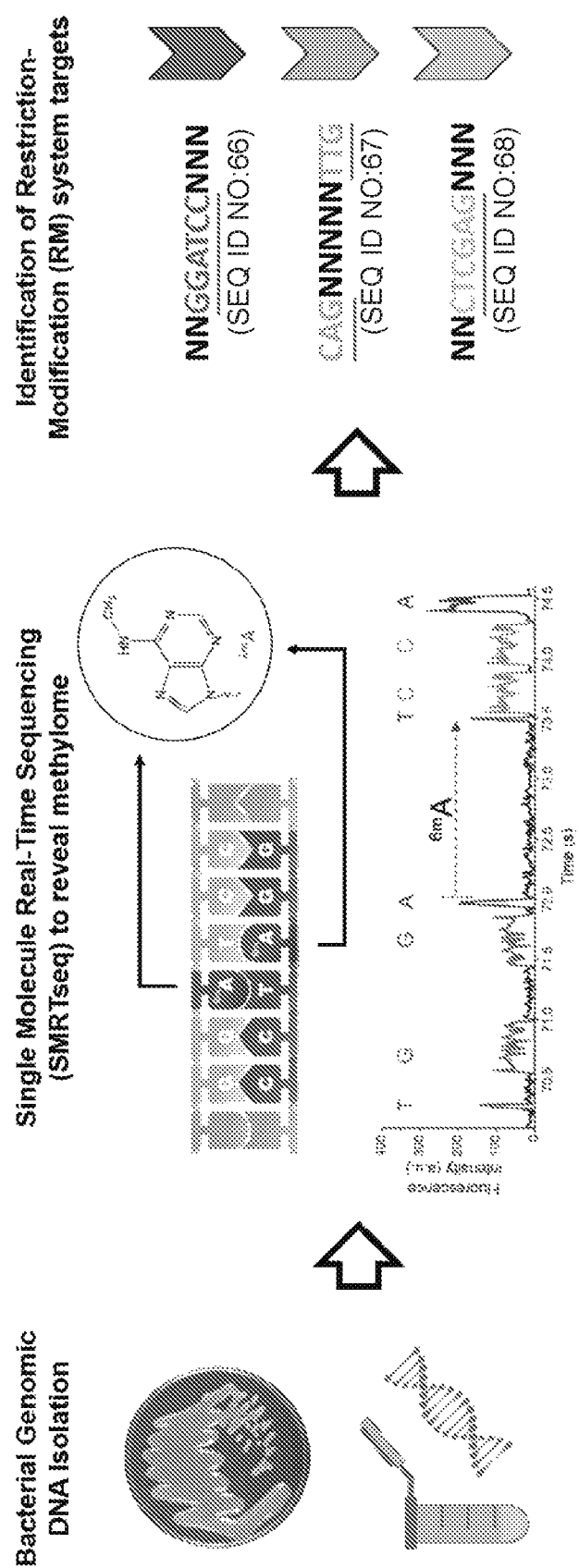
FIGS. 1A-1C show schematic representations of the SyngenicDNA approach to overcoming the restriction modification (RM) system inherent in a bacterium.

In certain aspects, the present disclosure provides engineered, minicircle (MC)-producing bacteria (e.g., *Escherichia coli*) that differentially methylate DNA therein, such that the MCs produced are not degraded by bacterial restriction-modification (RM) systems. Related engineered constructs are also described. Further, described herein are methods of using these engineered *E. coli* for producing MC DNA and for increasing the transformation efficiency of exogenous DNA into a target bacterium, as well as kits for use in such methods. The methods, synthetic constructs, and kits described herein can be used to overcome a target bacterium's RM system during genetic engineering. Advantageously, the methods, synthetic constructs, and kits described herein allow transformation of cells that were previously intractable.

Prior to setting forth this disclosure in more detail, it may be helpful to an understanding thereof to provide definitions of certain terms to be used herein. Additional definitions are set forth throughout this disclosure.

As used herein, "nucleic acid" or "nucleic acid molecule" refers to deoxyribonucleic acid (DNA), ribonucleic acid (RNA), or a combination thereof. For example, nucleic acid molecules (e.g., oligonucleotides), including those generated by the polymerase chain reaction (PCR) or by in vitro transcription, and to those generated by any of ligation, scission, endonuclease action, or exonuclease action. In certain embodiments, the nucleic acids of the present disclosure are produced by PCR. Nucleic acids can be composed of monomers that are naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. In embodiments, modified nucleic acids are peptide nucleic acids (PNA). Modified nucleic acids can include modified backbone residues or linkages that are synthetic, naturally occurring, or non-naturally occurring, and which have similar binding properties as a reference naturally occurring nucleic acid, and which are metabolized in a manner similar to the reference nucleic acid. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, methyl phosphonate (e.g., chiral methyl phosphonate), 2-0-methyl ribonucleotide, and the like. In various embodiments, modified internucleotide linkages are used. Modified internucleotide linkages are well known in the art and include methylphosphonates, phosphorothioates, phosphorodithionates, phosphoroamidites and phosphate ester linkages. Nucleic acid molecules can be either single stranded or double stranded. Additionally, nucleic acid molecules can refer to sense or anti-sense strands, cDNA, genomic DNA, recombinant DNA, RNA, mRNA, naturally occurring molecules, and wholly or partially synthesized nucleic acid molecules.

The terms "nucleotide sequence" or "nucleic acid sequence" refer to the order of nucleotides in a heteropolymer of nucleotides.

As used herein, the terms "peptide" refers to a compound comprised of amino acid residues covalently linked by peptide bonds. A peptide must contain at least two amino acids, and no limitation is placed on the maximum number of amino acids. "Peptides" include, for example, biologically active fragments, substantially homologous peptides, oligopeptides, homodimers, heterodimers, variants of peptides, modified peptides, derivatives, analogs, fusion proteins, among others. The peptides include natural peptides, recombinant peptides, synthetic peptides, or a combination thereof.

A "peptide sequence" refers to the order of amino acids present in a peptide.

A "variant" is a nucleotide or peptide sequence that comprises one or more alterations. In other words, a variant differs from a reference sequence in one or more deletions, substitutions, additions, or modifications. Such alterations are readily introduced using standard mutagenesis techniques, such as oligonucleotide-directed site-specific mutagenesis as described, for example, in Adelman et al., 1983, DNA 2:183. Nucleotide variants may be naturally-occurring allelic variants or non-naturally occurring variants. In embodiments, variant sequences exhibit at least about 70%, 75%, 80%, 85%, 90%, 95%, 98%, 99%, or 100% sequence identity to the reference sequence. The complement of a variant nucleotide sequence hybridizes to the reference nucleotide sequence under stringent hybridization conditions.

By "alteration" is meant a change in a nucleic acid or amino acid sequence as detected by standard art known methods such as those described herein. Alteration(s) may independently be a substitution, deletion, addition, or other modification. In some embodiments, an alteration in the amino acid sequence comprises a conservative substitution, which typically includes substitutions within the following groups: glycine, alanine; valine, isoleucine, leucine; aspartic acid, glutamic acid, asparagine, glutamine; serine, threonine; lysine, arginine; and phenylalanine, tyrosine. In other embodiments, an alteration in a nucleic acid sequence results in a conservative substitution in the corresponding amino acid sequence. As used herein, an alteration may include a 5% change, a 10% change, a 25% change, a 40% change, or a 50% change in a sequence relative to a reference sequence. In various embodiments, an alteration includes a change of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or even 100% of the sequence. In embodiments, an alteration includes a change in a nucleic acid sequence of a RM target sequence.

"Sequence identity," as used herein, refers to the percentage of nucleic acid or amino acid residues in one sequence that are identical with the residues in a reference sequence after aligning the sequences and introducing gaps, if necessary, to achieve the maximum percent sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

"Substantially identical" refers to a peptide or nucleic acid molecule exhibiting at least 50% identity to a reference amino acid sequence or nucleic acid sequence, respectively. In embodiments, such a sequence is at least 60%, 80%, 85%, 90%, 95%, or 99% identical at the amino acid or nucleic acid level to the reference sequence.

Nucleic acid molecules having "substantial identity" to a target sequence are typically capable of hybridizing with the target sequence.

"Reference" refers to a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. In various embodiments, the reference sequence is the unaltered nucleotide or amino acid sequence.

The terms "target, "target sequence", "target region", and "target nucleic acid," as used herein, refer to a region or subsequence of a nucleic acid (e.g., a region of a nucleic acid that is recognized and bound by a particular methyl transferase).

The term "hybridization" as used herein refers to any process by which a first strand of nucleic acid binds with a second strand of nucleic acid through base pairing. (See, e.g., Wahl, G. M. and S. L. Berger, 1987, *Methods Enzymol.* 152:399; Kimmel, A. R., 1987, *Methods Enzymol.* 152:507). Hybridization can occur between fully complementary nucleic acid strands or between "substantially complementary" nucleic acid strands that contain minor regions of mismatch. "Hybridization" may refer to hydrogen bonding, which may be Watson-Crick, Hoogsteen, or reversed Hoogsteen hydrogen bonding, between complementary nucleobases. For example, adenine and thymine are complementary nucleobases that pair through the formation of hydrogen bonds.

In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C., and two washes of 30 minutes each in 0.2×SSC, 0.1% SDS at 65° C.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 20011 g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Unless otherwise indicated, a particular nucleic acid sequence may also refer to conservatively modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with suitable mixed base and/or deoxyinosine residues (Batzer et al., 1991, *Nucleic Acid Res,* 19:081; Ohtsuka et al., 1985, 1 *Biol. Chem.,* 260:2600-2608; Rossolini et al., 1994, *Mol. Cell Probes,* 8:91-98).

A "fragment" is a portion of a peptide or a nucleic acid molecule. Such a portion contains, for example, at least 10%, 20%, 30%, 40%, 50%, 60%, 70%, 80%, or 90% of the entire length of the reference peptide or nucleic acid molecule.

The term "isolated" means that the material is removed from its original environment (e.g., the natural environment if it is naturally occurring). Thus, an isolated biological material can be free of some or all cellular components, i.e., components of the cells in which the native material occurs naturally (e.g., cytoplasmic or membrane component). For example, a naturally occurring nucleic acid present in a microorganism is not isolated, but the same nucleic acid, separated from some or all of the co-existing materials in the natural system, is isolated. A material shall be deemed isolated if it is present in a cell extract or supernatant. In the case of nucleic acid molecules, an isolated nucleic acid includes a PCR product, an isolated mRNA, a cDNA, or a restriction fragment.

As used herein, "isolated nucleic acid" refers to a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids.

"Isolated nucleic acid molecule" also refers to a nucleic acid (e.g., a DNA molecule) that is free of the genes which, in the naturally-occurring genome of the organism from which the nucleic acid molecule is derived, flank the gene. In embodiments, an isolated nucleic acid is excised from the chromosome. In some embodiments, an isolated nucleic acid is no longer joined or proximal to other genes located upstream or downstream of the gene contained by the isolated nucleic acid molecule when found in the chromosome. In further embodiments, an isolated nucleic acid is no longer joined or proximal to non-coding regions, but may be joined to its native regulatory regions or portions thereof. In yet another embodiment, the isolated nucleic acid lacks one or more introns. Isolated nucleic acids include, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, isolated nucleic acid molecules include an RNA molecule that is transcribed from a DNA molecule, as well as a recombinant DNA molecule that is part of a hybrid gene encoding additional peptide sequence. Isolated nucleic acid molecules also include sequences inserted into plasmids, cosmids, artificial chromosomes, and the like.

Nucleic acids can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide encoded by the nucleic acid are maintained.

An "isolated peptide" is a peptide that has been separated from components that naturally accompany it. Typically, a peptide is considered to be "isolated" when it is at least 60%, by weight, free from other peptides and naturally-occurring organic molecules with which it is naturally associated. In embodiments, the preparation is at least 75%, at least 90%, or at least 99%, by weight, a peptide of the invention. An isolated peptide of the invention may be obtained, for example, by extraction from a natural source, by expression of a recombinant nucleic acid encoding such a peptide; or by chemically synthesizing the peptide. Purity can be measured by any appropriate method, for example, column chromatography, polyacrylamide gel electrophoresis, or by HPLC analysis.

The term "purified" as used herein refers to material that has been isolated under conditions that reduce or eliminate the presence of unrelated materials, i.e. contaminants, including native materials from which the material is obtained. For example, a purified DNA is preferably substantially free of cell or culture components, including tissue culture components, contaminants, and the like. As used herein, the term "substantially free" is used operationally, in the context of analytical testing of the material. In embodiments, purified material is substantially free of contaminants if it is at least 50% pure, at least 75% pure, at least 90% pure, or at least 99% pure. Purity can be evaluated by chromatography (e.g., high performance liquid chromatography), gel electrophoresis (e.g., polyacrylamide gel electrophoresis), immunoassay, composition analysis, biological assay, and other methods known in the art. In embodiments, a "purified" nucleic acid or peptide gives rise to essentially one band in an electrophoretic gel. For a peptide that can be subjected to modifications, for example, phosphorylation or glycosylation, different modifications may give rise to different isolated peptides, which can be separately purified.

Techniques to isolate and purify specific nucleic acids and peptides are well known to those of skill in the art. In accordance with the present disclosure there may be employed conventional molecular biology, microbiology, and recombinant DNA techniques within the skill of the art. Such techniques are explained fully in the literature. See, e.g., Sambrook et al., Molecular Cloning: A Laboratory Manual, Second Edition (Cold Spring Harbor, NY: Cold Spring Harbor Laboratory Press, 1989).

"Detect" refers to identifying the presence, absence, or amount of the analyte to be detected.

As used herein, "in silico" is an adjective used to describe an action performed on a computer or via computer simulation. For example, "in silico analysis of the human genome," is a human genome analysis performed with a computer.

The term "endogenous" refers to material (e.g., nucleic acid, amino acid, etc.) that is found innately or naturally in the bacteria. For example, an "endogenous" enzyme is naturally encoded in the genome and expressed in the target bacteria.

The term "exogenous" refers to material that is not found innately or naturally in the target bacteria. For example, an "exogenous" nucleic acid material is derived from outside the target bacteria and is being introduced into the target bacteria.

A "syngenic" nucleic acid refers to an exogenous nucleic acid molecule that includes modifications or alterations relative to an endogenous reference sequence, wherein the modifications or alterations are sufficient to ensure that the nucleic acid molecule is not degraded when introduced into a bacterial cell of interest. A syngenic nucleic acid molecule may refer to a synthetic nucleic acid molecule that has been engineered with sufficient sequence and epigenetic compatibility to allow it to function as an endogenous nucleic acid molecule within a specific bacterial host, upon artificial transformation, and to be accepted by the bacterial RM defenses.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

"Operably linked" means that a first nucleic acid molecule is positioned adjacent to a second nucleic acid molecule that directs transcription of the first nucleic acid molecule when appropriate molecules (e.g., transcriptional activator proteins) are bound to the second nucleic acid molecule.

"Promoter" refers to a nucleic acid sequence that is used to initiate transcription. As used herein, a promoter refers to a nucleic acid sequence that directs transcription of at least a portion of a nucleic acid molecule to which the promoter is operatively linked. In embodiments, the promoter includes a nucleic acid sequence that is sufficient for RNA polymerase recognition, binding, and transcription initiation. In addition, the promoter may include sequences that modulate transcription initiation, such as cis acting elements which may be responsive to trans acting factors. Exemplary promoters include nucleic acid sequences of about 100, 250, 300, 400, 500, 750, 900, 1000, 1250, and 1500 nucleotides that are upstream (e.g., immediately upstream) of the translation start site.

A "plasmid" is a circular nucleic acid molecule that is separate from the chromosomal DNA and can replicate independently. A plasmid may comprise a selectable marker to indicate the success of transformation or other procedures meant to introduce the plasmid into a cell. Additionally, a plasmid may comprise a multiple cloning site that includes multiple restriction enzyme consensus sites to enable the insertion of a nucleic acid sequence. Plasmid vectors may be "cloning vectors" or "donor vectors," which are used to ease cloning and to amplify a sequence of interest. Other plasmid vectors, which are referred to as "expression vectors" or "acceptor vectors," are used for the expression of a gene of interest in a defined target cell. Expression vectors generally include an expression cassette, which comprises or consists of a promoter, a transgene, and a terminator sequence. In embodiments, expression vectors can be shuttle plasmids that contain elements that enable their propagation and selection in different host cells.

"Minicircles" (MCs) are small excised, circular DNA fragments from a PP that no longer contain antibiotic resistance markers or the bacterial origin of replication. These are small, non-viral, episomal expression vectors that can be used in vivo or in vitro and provide for long-term transient expression of one or more transgenes without the risk of immunogenic responses that can be caused by the bacterial backbone in standard plasmids. MCs are excised from PP via a site-specific recombination reaction. MCs do not replicate with the host cell, expression can last for 14 days or longer in dividing cells, and can continue for months in non-dividing cells.

As used herein, the term "minicircle-producing" bacterium refers to a bacterium that allows both the propagation of a parental plasmid (PP) and the production of the minicircles (MCs) from the PP. The PP is a bacterial plasmid that contains a transgene insert that is flanked by two recombinase-target sequences at both ends of the insert. The two recombinase-target sequences facilitate recombinase-mediated excision of the insert when the recombinase is induced in the bacterium. The PP is a self-replicating episomal plasmid having its bacterial origin of replication and additionally antibiotic resistance markers. The PP also contains several restriction sites of a specific restriction enzyme that is inducible in the bacterium while the transgene insert does not have any restriction site of the specific restriction enzyme. When the recombinase and the specific restriction enzyme are induced in a MC-producing bacterium, the transgene insert is excised as MCs by recombination and the remaining PP is degraded by the induced specific restriction enzyme. This ensures that MCs do not have any contamination of the host PP DNA.

A "host cell" may be any prokaryotic or eukaryotic cell that contains a cloning vector or an expression vector. This term also includes prokaryotic or eukaryotic cells that have been genetically engineered to contain the cloned gene(s) in the chromosome or genome of the host cell.

"Methyltransferase" refers to an enzyme that methylates its substrate, i.e., adds a methyl group ($-CH_3$) to the substrate. In embodiments, a methyltransferase is an enzyme that adds a methyl group ($-CH_3$) to adenine or cytosine bases within a recognition sequence, which protects the recognition sequence from certain endonucleases that cleave only in the absence of a methyl group in the recognition sequence. Examples of recognition sequences are CC̲WGG, where the W is A or T, GA̲TC, and AA̲CN$_6$GTGC (SEQ ID NO:1), where N is any nucleotide and the underlined base is methylated by the methyltransferase.

DAM methyltransferase, an abbreviation for deoxyadenosine methyltransferase, is an enzyme that is encoded by the dam gene, Gene ID 947893. DAM adds a methyl group to the adenine of the sequence 5'-GATC-3' in newly synthesized DNA. DAM, (EC:2.1.1.72), transfers a methyl group from —S-adenosylmethionine (SAM) to the N6 position of the adenine residues in the sequence GATC. The protein ID of DAM on UniProt is P0AEE8 or DMA ECOLI.

Dcm methyltransferase, an abbreviation for deoxycytosine methyltransferase, is also known as Mec methyltransferase, is an enzyme that is encoded by the Dcm gene, Gene ID 946479. Dcm is an enzyme, (EC:2.1.1.37), that adds a methyl group to the internal (second) cytosine residues in the sequences 5'-CCAGG-3' and 5'-CCTGG-3' [5'-CC(A/T)GG-3] at the C5 position. The protein ID of Dcm on UniProt is P0AED9 or Dcm ECOLI.

HsdM methyltransferase is part of the Type I RM system in bacteria, the DNA-methyltransferase subunit M, and the enzyme adds a methyl group to the second adenine in the sequence 5'-AACNNNNNNGTGC-3' (SEQ ID NO:1). The gene ID for HsdM is 6276026. The protein ID of HsdM on UniProt is B1VCK6 or B1VCK6 ECOLX.

A bacterium is "deficient" in a methyltransferase if the methyltransferase is substantially absent or non-functional. In some embodiments, a methyltransferase is substantially absent or non-functional if at least 90% of the activity of the methyltransferase has been eliminated. In further embodiments, a methyltransferase is substantially absent or non-functional if at least 95% of the activity of the methyltransferase has been eliminated. In specific embodiments, a bacterium is deficient in a methyltransferase if the methyltransferase is absent or non-functional. Various techniques to reduce the presence or activity of an enzyme, as well as to knock out an enzyme are known to those of skill in the art. Additionally, techniques to assess (e.g., quantify) the presence or activity of an enzyme are well known.

As used herein, "non-functional" in the context of methyltransferase refers to an enzyme that is catalytically inactive. In other words, the enzyme is incapable of performing its enzymatic catalytic reaction, i.e., it does not add a methyl group ($-CH_3$) to its substrate.

The term "recombineering" refers for in vivo homologous recombination-mediated genetic engineering, for example, in dam, Dcm, or HsdM gene editing of the described engineered bacteria. In "CRISPR-mediated recombineering," the homologous recombination is mediated by the Clustered Regularly Interspaced Short Palindromic Repeat (CRISPR)/CRISPR-associated cleavage enzyme system, for example, the CRISPR/Cas9. The CRISPR system facilitates DNA double-strand break at a defined site in the genome. This then activate the cell's innate DNA repair mechanism in the presence of a homologous repair template that was introduced into the cell. The double-strand break is repaired by homologous recombination with the modified template that contains a desired genome modification. In this way, DNA insertions, deletions, point mutants, in-frame transgene fusions, or any other modification can be engineered into a genome.

Certain tools of statistical analysis (e.g., two-sided one-sample t-test, two-tailed Fisher's exact test) are referred to herein. In certain embodiments, modified statistical tools are referred to, which are described in detail herein.

Unless clearly indicated otherwise, as used herein, the term "or" is understood to be inclusive. Unless specifically stated or obvious from context, as used herein, the terms "a", "an", and "the" are understood to be singular or plural.

Unless clearly indicated otherwise, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. In other words, the term "consisting essentially of" limits the scope of a claim to the specified materials or steps, or to those that do not materially affect the basic characteristics of a claimed invention. For example, a peptide domain, region, or module (e.g., a binding domain, hinge region, linker module) or a peptide (which may have one or more domains, regions, or modules) "consists essentially of" a particular amino acid sequence when the amino acid sequence of a domain, region, module, or peptide includes extensions, deletions, mutations, or a combination thereof (e.g., amino acids at the amino- or carboxy-terminus or between domains) that, in combination, contribute to at most 20% (e.g., at most 15%, 14%, 13%, 12%, 11%, 10%, 9%, 8%, 7% 6%, 5%, 4%, 3%, 2% or 1%) of the length of a domain, region, module, or peptide and do not substantially affect (i.e., do not reduce the activity by more than 50%, such as no more than 40%, 30%, 25%, 20%, 15%, 10%, 5%, or 1%) the activity of the domain(s), region(s), module(s), or peptide (e.g., the target binding affinity of a binding peptide).

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof Any compositions or methods provided herein can be combined with one or more of any of the other compositions and methods provided herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

"Optional" or "optionally" means that the subsequently described event or circumstances may or may not occur, and that the description includes instances where said event or circumstance occurs and instances in which it does not.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the nucleic acid molecules and peptides of the invention, and, as such, may be considered in making and practicing the invention. Particularly useful techniques for particular embodiments will be discussed in the sections that follow.

Engineered Bacteria and Minicircles Produced Therein

Described herein is a versatile strategy to overcome restriction-modification (RM) system barriers, which is suitable for use in a broad range of bacterial species. In embodiments, the problem to be solved is that the number of RM systems present and the target sequences recognized are hyper-variable and highly species, often even strain, specific. Accordingly, described herein are engineered, MC-producing bacteria (e.g., *Escherichia coli*) that are deficient in at least one methyltransferase, such that DNA therein is differentially methylated (e.g., methylation-free), as well as methods of using these bacteria for producing MC DNA and for increasing the transformation efficiency of exogenous DNA when transformed into target bacteria. Also described are kits for use in such methods.

By way of content, genetic intractability is a barrier in basic, synthetic, and translational microbiology research and development beyond a few model organisms. Restriction-modification (RM) systems are the most common underlying cause of genetic intractability in bacterial species. RM systems are found in bacteria and other prokaryotic organisms, and provides a defense against foreign DNA, such as that borne by bacteriophages. RM systems enable bacteria to distinguish endogenous (i.e., 'self') from exogenous (i.e., 'non-self') DNA. RM systems are organized in different architectures (convergent or divergent) and are characterized by different features, e.g., binding cooperativities, dissociation constants of dimerization, and translation rates, which ensure this tight regulation. RM systems hinder the use of genetic approaches in most of bacteria, and exhibit strain-level variation.

RM systems generally function via two enzymes: a restriction endonuclease and a modification methyltransferase. Restriction endonucleases cleave double stranded DNA at specific points into fragments, which are then degraded further by other endonucleases. This prevents infection by effectively destroying the foreign DNA introduced by an infectious agent (such as a bacteriophage). As the sequences recognized by the restriction enzymes are very short, the bacterium itself will almost certainly contain some within its genome. In order to prevent destruction of its own DNA by the restriction enzymes, methyl groups are added. These modifications must not interfere with the DNA base-pairing, and therefore, usually only a few specific bases are modified on each strand. The restriction endonuclease recognizes the methylation status of DNA at a highly specific DNA target sequence and degrades unmethylated or inappropriately methylated targets, which are identified as exogenous. Restriction endonucleases cleave internal phosphodiester bonds only after recognizing specific sequences in DNA which are usually 4-6 base pairs long, and often palindromic. Restriction endonuclease enzymes are highly specific in target sequence recognition. RM target motifs vary greatly in sequence and length, ranging from 4-18 base pairs (bp), with more than 450 different motifs identified to date. A cognate methyltransferase protects the same target sequence across the host's genome via addition of a methyl group, marking each site as endogenous.

RM systems are an extremely diverse group of enzymes that are differentiated into four types (Type I, II, III, and IV), based on their recognized target motifs, subunit composition, cleavage position, cofactor requirements, and substrate specificity. The four categories of RM systems are: Type I, Type II, Type III, all with restriction enzyme activity and a methyltransferase activity, and Type IV with only restriction enzyme activity (and no methyltransferase activity).

Type I systems are the most complex, consisting of three peptides: R (restriction), M (modification), and S (specificity). The resulting complex can both cleave and methylate DNA. Both reactions require ATP, and cleavage often occurs a considerable distance from the recognition site. The S subunit determines the specificity of both restriction and methylation. Cleavage occurs at variable distances from the recognition sequence, so discrete bands are not easily visualized by gel electrophoresis.

Type II systems are the simplest and the most prevalent. Instead of working as a complex, the methyltransferase and endonuclease are encoded as two separate peptides and act independently (there is no specificity peptide). Both peptides recognize the same recognition site, and therefore compete for activity. The methyltransferase acts as a monomer, methylating the duplex one strand at a time. The endonuclease acts as a homodimer, which facilitates the cleavage of both strands. Cleavage occurs at a defined position close to or within the recognition sequence, thus producing discrete fragments during gel electrophoresis. For this reason, Type II systems are used in labs for DNA analysis and gene cloning.

Type III systems have R (res) and M (mod) peptides that form a complex of modification and cleavage. The M peptide, however, can methylate on its own. Methylation also only occurs on one strand of the DNA unlike most other known mechanisms. The heterodimer formed by the R and M peptides competes with itself by modifying and restricting the same reaction. This results in incomplete digestion.

Type IV systems are not true RM systems because they only contain a restriction enzyme and not a methyltransferase. Unlike the other types, Type IV restriction enzymes recognize and cut only modified DNA, most commonly, methylated DNA. Thus, the Type IV restriction enzymes are modification-dependent enzymes.

Most, if not all, of the currently available approaches to overcome RM systems during genetic engineering are inspired by bacteriophage anti-restriction mechanisms. Bacteriophage mechanisms that involve methyl-modification of the phage genome to subvert the host's RM activities have already been translated into in vitro engineering approaches. These can all be referred to as mimicry-by-methylation, as they essentially seek to modify the methylation pattern of a genetic tool to match the desired host and achieve molecular mimicry. There are two common mimicry-by-methylation approaches. (A) Methylate target sites on tools by using in vitro methylation with recombinant methyltransferase enzymes, which are currently commercially available for only 37 of more than 450 known targets. (B) Alternatively, achieve in vivo methylation by passaging a plasmid through a related strain that is either restriction enzyme deficient or a surrogate strain that has been extensively engineered to match the methylation profile of the strain of interest, referred to as plasmid artificial modification (PAM). Although these are effective in some cases, owing to the labor-intensive and rigid nature of their underlying design, they are not readily adaptable to other strains due to RM system diversity.

Advantageously, the present inventors have discovered that if exogenous DNA lacks the highly specific target recognition motifs for a host's RM systems, it is invisible to these systems and will not be degraded during artificial transformation. Because RM defenses recognize genetic tools as xenogeneic DNA by virtue of the methylation status of highly specific target motifs (Vasu K, et al., (2012) Promiscuous restriction is a cellular defense strategy that confers fitness advantage to bacteria. *Proc Natl Acad Sci USA* 109(20):E12871293), the systematic identification and elimination of such target motifs from the nucleotide sequence of a genetic tool therefore facilitates the engineering of an artificial syngeneic DNA molecule that is RM-silent upon transformation. Accordingly, it is possible to prevent degradation of exogenous DNA in intractable bacteria by eliminating methylation at the adenosine and cytosine residues in certain sequence motifs that are specifically recognized by the bacterial innate genetic defenses, even in the Type IV RM system of the intractable bacteria. This, in turn, improves the transformation efficiency of exogenous DNA in the intractable bacteria, and facilitates genetic manipulation of the intractable bacteria.

Accordingly, provided herein is an engineered, MC-producing bacterium that is deficient in an endogenous methyltransferase and thereby has reduced DNA-methylation capability (e.g., relative to wildtype). Such bacteria produce differentially methylated (e.g., methylation-free) MC DNA that can then be transformed into other bacteria, e.g., intractable bacteria.

The bacterial strains described herein are useful for circumventing the RM systems, including the Type IV RM system. The restriction endonucleases of the Type IV RM system specialize in degrading methyl-modified nucleic acid at endonuclease-recognized sequences. By propagating nucleic acids in the new bacteria strain that is deficient in an endogenous methyltransferase, the nucleic acids do not have the native methylation pattern of the bacteria, and as such, are essentially invisible to the Type IV RM system.

In embodiments, the engineered, MC-producing bacterium is deficient in at least one endogenous methyltransferase. In some embodiments, the at least one endogenous methyltransferase methylates a cytosine residue of a sequence CCWGG, wherein the W is A or T. In particular embodiments, the at least one endogenous methyltransferase methylates an adenosine residue of a sequence GATC, a sequence AACN$_6$GTGC (SEQ ID NO:1), or both. In further embodiments, the at least one endogenous methyltransferase methylates a cytosine residue and an adenosine residue.

In some embodiments, the engineered, MC-producing bacterium is deficient in at least one endogenous Dam, Dcm, or HsdM methyltransferase. These methyltransferases add methyl groups to the adenosine and cytosine residues in specific DNA motif sequences. Specifically, Dam adds a methyl group to the adenine of the sequence 5'-GATC-3' in newly synthesized DNA, Dcm adds a methyl group to the internal (second) cytosine residues in the sequences 5'-CCAGG-3' and 5'-CCTGG-3' [5'-CC(A/T)GG-3'] at the C5 position, and HsdM methyltransferase adds a methyl group to the second adenine in the sequence 5'-AACNNNNNNGTGC-3' (SEQ ID NO:1). In various embodiments, the engineered MC-producing bacterium is deficient in Dam. In further embodiments, the engineered MC-producing bacterium is deficient in Dcm. In additional embodiments, the engineered MC-producing bacterium is deficient in HsdM. In specific embodiments, the engineered MC-producing bacterium is Dam−/Dcm+/HsdM+. In further embodiments, the engineered MC-producing bacterium is Dam+/Dcm−/HsdM+. In other embodiments, the engineered MC-producing bacterium is Dam+/Dcm+/HsdM−. In still further embodiments, the engineered MC-producing bacterium is Dam−/Dcm−/HsdM+. In additional embodiments, the engineered MC-producing bacterium is Dam−/Dcm+/HsdM−. In particular embodiments, the engineered MC-producing bacterium is Dam+/Dcm−/HsdM−. In yet further embodiments, the engineered MC-producing bacterium is Dam−/Dcm−/HsdM−. As used herein, the negative sign indicates that the bacterium is deficient in the respective methyltransferase, and the positive sign indicates that the bacterium is not-deficient in the respective methyltransferase.

In embodiments, the one or more endogenous methyltransferase are absent in the engineered MC-producing bacterium. In some embodiments, the engineered MC-producing bacterium does not express one or more of the Dam, Dcm, and HsdM methyltransferases. That is, the genes encoding these methyltransferases are not expressed. In various embodiments, the dam, Dcm, and/or HsdM methyltransferase genes are modified (e.g., mutated) in the bacterial genome, e.g., by insertions, deletions, point mutants, or the like. In some embodiments, the modification is such that no amino acid sequence is transcribed and translated from the gene. In other embodiments, the one or more endogenous methyltransferase are not functional in the engineered MC-producing bacterium. In embodiments, the engineered, MC-producing bacterium expresses one or more of the Dam, Dcm, and HsdM methyltransferases that are non-functional, e.g., the methyltransferase is truncated.

The methyltransferase genes (dam, Dcm, HsdM) or associated genes required for their function (for example, HsdS, the specificity subunit of the Hsd system, which encodes the sequence motif target) may be targeted for deletion or gene inactivation using a number of genetic engineering techniques including CRISPR-Cas engineering, recombineering, suicide vector or interruption using homologous recombination with linear/circular DNA cassettes which introduce indels or new genes into the sequences of methyltransferase open reading frames (ORF). These methods are known in the art. See, WO2014043637, WO2014143381, US20110027313, U.S. Pat. No. 6,872,547 and US20030121068 as examples. The contents, and in particular, the relevant disclosure of these publications are hereby incorporated by reference in their entirety.

In some embodiments of the engineered, MC-producing bacterium, the methyltransferase genes or associated genes are mutated by gene editing. For example, by recombineering. In one embodiment, the recombineering is mediated by CRISPR technology that is known in the art, such as Cas9-triggered homologous recombination. See, WO2014143381, WO2014093694, WO2015017866, WO2015065964, and US20150031134, the contents, and in particular, the relevant disclosure of which are hereby incorporated by reference.

In particular embodiments, a combination of λ-Red recombineering to delete the methyltransferase ORFs in a scarless fashion, followed by a selection for successful mutants using CRISPR targeting of methyltransferase genes (toxic to clones containing methyltransferase gene but allowing successfully recombineered methyltransferase deficient clones to grow) is used. Advantageously, such a combination allows for creation of engineered MC-producing strains of bacteria (e.g., E. coli), without the need for continued antibiotic selection.

Additionally, as noted above, the bacterium of the present disclosure produce minicircles (MCs). MCs are small (~4 kb) circular plasmid derivatives that have are free from all prokaryotic vector parts. In other words, the circular DNA elements no longer contain antibiotic resistance markers or the bacterial origin of replication. These small vectors can be used in vivo or in vitro and provide for long-term transient expression of one or more transgenes without the risk of immunogenic responses that can be caused by the bacterial backbone in standard plasmids.

MCs are produced using a parent plasmid (PP) and an engineered bacterial strain (e.g., an E. coli strain) that allows both propagation of the PP and production of the MC. Accordingly, described herein is an engineered bacterium comprising: a PP comprising a MC nucleic acid sequence comprising an exogenous nucleic acid sequence, wherein the engineered bacterium is deficient in at least one endogenous methyltransferase. Embodiments further include an engineered bacterium comprising a PP comprising a MC nucleic acid sequence comprising an exogenous nucleic acid sequence, wherein the engineered bacterium is deficient in at least one endogenous methyltransferase such that the engineered bacterium has reduced DNA-methylation capability.

In various embodiments, the preparation of MCs is as follows: (1) production and propagation of a PP, which is bacterial plasmid with eukaryotic inserts (e.g., the exogenous DNA molecule to be introduced into the intractable bacteria) in E. coli; (2) the induction of a site-specific recombinase while in E. coli; (3) the excision of prokaryotic vector parts via recombinase-target sequences at the ends of the insert in the PP; and (4) recovery of the resulting MCs by capillary gel electrophoresis (CGE).

In some embodiments, MC are generated by the expression of an inducible ΦC31 integrase via intramolecular (cis-) recombination. The full-size MC-DNA construct is grown in a host bacterial strain (e.g., an E. coli strain) that harbors an arabinose-inducible system to express the ΦC31 integrase and the I-SceI endonuclease simultaneously. The ΦC31 integrase produces the MC-DNA molecules from the full-size PP-DNA upon arabinose induction. The PP-DNA contains a number of engineered I-SceI restriction sites that are subject to I-SceI endonuclease digestion and ultimate destruction of the PP-DNA. The MC-DNA lacks I-SceI restriction site so that it remains intact. By including several I-SceI sites in the PP-DNA enables production of super clean MC-DNA without PP-DNA contamination. In embodiments, the engineered bacterial strain produces purified MC-DNA in a time frame and quantity similar to those of routine plasmid DNA preparation. Methods of making MCs are known in the art. For example, US20060211117, US20070031378, U.S. Pat. No. 8,945,885, and US20150031134, the entire contents, and in particular, the relevant disclosure of which are hereby incorporated by reference.

Accordingly, the engineered, MC-producing bacterium comprises a PP that comprises an exogenous DNA molecule that is to be introduced into an intractable bacterium, such that the engineered, MC-producing bacterium is capable of propagating the PP therein and supporting the production of MC comprising the exogenous DNA sequence from the PP upon induction. In some embodiments, the engineered, MC-producing bacterium comprises an inducible ΦC31 integrase. In particular embodiments, the inducible ΦC31 integrase is induced by arabinose. The induced expressed ΦC31 integrase would excise the MC, which contains the exogenous DNA sequence, from the PP. In some embodiments, the engineered, MC-producing bacterium comprises an inducible I-SceI homing endonuclease. In such embodiments, the induced I-SceI homing endonuclease degrades the PP DNA after the MC has been excised, which prevents the MC from being contaminated by bacterial DNA. In specific embodiments, the inducible I-SceI homing endonuclease is induced by arabinose. In some embodiments, the exogenous DNA sequence in the PP does not contain an I-SceI homing endonuclease recognition sequences. This ensures that the MCs produced are not degraded with the remains of the PP. In some embodiments, the exogenous DNA sequence in the PP does not contain a Type I RM restriction endonuclease recognition sequence. For example, the 5'-CCAYN$_6$TGT-3' (SEQ ID NO:2) or 5'-GGTRN$_6$ACA-3' (SEQ ID NO:3) where Y=C or T and R=A or G.

Further embodiments include an engineered bacterium comprising: a MC plasmid comprising an exogenous nucleic acid sequence, wherein the engineered bacterium is deficient in at least one endogenous methyl transferase. Embodiments also include an engineered bacterium comprising a MC plasmid comprising an exogenous nucleic acid sequence, wherein the engineered bacterium is deficient in at least one endogenous methyltransferase such that the engineered bacterium has reduced DNA-methylation capability.

Additionally, provided herein is a MC produced from an engineered, MC-producing bacterium described herein, or from a kit comprising an engineered, MC-producing bacterium described herein.

Embodiments further include a host cell, comprising: a plasmid comprising a nucleic acid sequence that is exogenous to the host cell, wherein the exogenous nucleic acid sequence lacks methylation at a plurality of methylation cites that would be methylated in a reference *E. coli* bacterium.

Methods of Using an Engineered Bacterium

Also provided herein are various methods of using the engineered bacteria described herein. For example, provided are methods comprising:

transforming a parental plasmid into an engineered bacterium that is deficient in at least one endogenous methyltransferase, the parental plasmid comprising a minicircle nucleic acid sequence comprising an exogenous nucleic acid sequence; and producing a minicircle comprising the minicircle nucleic acid sequence.

Further methods described herein comprise:

producing a MC comprising an exogenous nucleic acid sequence in an engineered bacterium described herein; and transforming the MC into a second bacterium, the MC resisting degradation when transformed into the second bacterium.

Further described are methods for generating an exogenous DNA molecule that resists degradation when transformed into a bacterium of interest, the method comprising providing an engineered, MC-producing bacterium that is deficient in at least one methyltransferase and thereby has reduced DNA-methylation capability, and producing the exogenous DNA as MCs from the engineered, MC-producing bacterium described herein wherein the MCs comprise the exogenous DNA. In one embodiment, the bacterium of interest is an intractable bacterium. In one embodiment, the resistance to degradation is conferred by methyl-free or differential methylation status at the adenosine and cytosine residues in certain DNA motifs that are specifically recognized by the Type IV restriction-modification (RM) systems of the intractable bacteria. For examples, the second cytosine in the sequence 5'-CC(A/T)GG-3' wherein W=A or T, and the adenosine in the sequences 5'-GATC-3' or 5'-AACN$_6$GTGC-3' (SEQ ID NO:1) are not methylated. In one embodiment, the engineered, MC-producing bacterium that is deficient in at least one methyltransferase as described herein comprises a parent plasmid (PP) which comprises the exogenous DNA insert. In one embodiment, the exogenous DNA insert in the PP is flanked by two recombinase-target sequences at both ends of the insert. In one embodiment, the recombinase is ΦC31 integrase that is inducible in the engineered, MC-producing bacterium. In one embodiment, the PP in the engineered, MC-producing bacterium contains several engineered I-SceI restriction sites that are subject to I-SceI endonuclease digestion and ultimate destruction of the PP-DNA. In one embodiment, the exogenous DNA insert in the PP lacks I-SceI restriction site so that it remains intact in the presence of I-SceI endonuclease when its expression is induced. In one embodiment, the engineered, MC-producing bacterium comprises an inducible ΦC31 integrase. In one embodiment, the engineered, MC-producing bacterium comprises an inducible I-SceI endonuclease.

In another aspect, the invention provides a method for generating a exogenous DNA that resists degradation when transformed into a bacterium of interest, the method comprises (a) providing an engineered, MC-producing bacterium that is deficient in at least one methyltransferase and thereby has reduced DNA-methylation capability as described herein, wherein the bacterium comprises a PP, which comprises the exogenous DNA insert flanked by two recombinase-target sequences at both ends of the insert; (b) inducing the expression of the recombinase in the bacterium; and (b) producing the exogenous DNA as MC from the engineered, MC-producing bacterium described herein, wherein the MC comprise the exogenous DNA. In one embodiment, the method further comprises inducing expression of an endonuclease to degrade the remaining PP DNA after the recombination reaction producing the MCs.

In another aspect a method of improving the transformation efficiency of a exogenous DNA when it is transformed into a bacterium of interest, the method comprises producing the exogenous DNA as MC from an engineered, MC-producing bacterium described herein wherein the MC comprise the exogenous DNA, and transforming the MC into the bacterium of interest. In one embodiment, the bacterium of interest is an intractable bacterium. While not wishing to be bound by theory, the improved the transformation efficiency is due to reduced degradation by the recipient bacterium's Type IV RM system. The recipient's Type IV RM system requires methylation at specific recognition sequences. Absent such methylation, the recipient bacterium fails to recognize that the transformed exogenous DNA as foreign DNA and therefore, does not degrade the exogenous DNA. In one embodiment, the failure to degrade or protection for the Type IV RM system in the recipient bacterium is conferred by methyl-free or differential methylation status at the adenosine and cytosine residues in certain DNA motifs that are specifically recognized by the Type IV restriction-modification (RM) systems of the intractable bacteria. For examples, the second cytosine in the sequence 5'-CC(A/T)WGG-3' wherein W=A or T and the adenosine in the sequences 5'-GATC-3' or 5'-AACN$_6$GTGC-3' (SEQ ID NO:1) are not methylated. In one embodiment, the engineered, MC-producing bacterium that is deficient in at least one methyltransferase as described herein comprises a PP, which comprises the exogenous DNA insert. In one embodiment, the exogenous DNA insert in the PP is flanked by two recombinase-target sequences at both ends of the insert. In one embodiment, the recombinase is ΦC31 integrase that is inducible in the engineered, MC-producing bacterium. In one embodiment, the PP in the engineered, MC-producing bacterium contains several engineered I-SceI restriction sites that are subject to I-SceI endonuclease digestion and ultimate destruction of the PP-DNA. In one embodiment, the exogenous DNA insert in the PP lacks I-SceI restriction site so that it remains intact in the presence of I-SceI endonuclease when its expression is induced. In one embodiment, the engineered, MC-producing bacterium comprises an inducible ΦC31 integrase. In one embodiment, the engineered, MC-producing bacterium comprises an inducible I-SceI endonuclease.

In various embodiments, the methods described herein further comprise engineering the engineered, MC-producing bacterium, such that the bacterium is deficient in at least one endogenous methyltransferase. In some embodiments, the engineering comprises editing the gene encoding the at least one methyltransferase by CRISPR-mediated recombineering.

Methods of Identifying Restriction-Modification (RM) System Target Motifs in a Bacterial Strain Also described herein are methods of identifying RM system target motifs in a particular bacterial strain. Post-replicative modification of DNA by methyltransferases in bacteria results in three types of epigenetic markers: N6-methyladenine ($^{m6}$A), N4-methylcytosine ($^{m4}$C), and 5-methylcytosine ($^{m5}$C) (Johnston C D, et al., (2017) Restriction-modification mediated barriers to exogenous DNA uptake and incorporation employed by *Prevotella intermedia*. *PLoS One* 12(9):e0185234). The complete set of methylations across a bacterial genome is referred to as the methylome. Methylome analysis can be accomplished by using single molecule real-time sequencing (SMRTseq; PACBIO®) (Davis B M, et al., (2013) Entering the era of bacterial epigenomics with single molecule real time DNA sequencing. *Current opinion in microbiology* 16(2):192-198). During SMRTseq, a polymerase adds fluorescently labelled bases to a DNA template while the sequencing instrument records both the sequence of bases added and the kinetic information (milliseconds) between successive additions, forming a sequencing trace. DNA templates containing a methylated base cause the polymerase to stall at those sites, leading to a delay in the sequence trace. This kinetic information is used to identify the specific sites of methylation in genomic DNA ($^{m6}$A, $^{m4}$C or $^{m5}$C) based on their characteristic trace (Davis B M, et al., (2013) Entering the era of bacterial epigenomics with single molecule real time DNA sequencing. *Current opinion in microbiology* 16(2): 192-198). SMRTseq analysis software summarizes the exact sequence of the methylated motifs, the number of motifs present on the genome and the percentage of motifs that are methylated.

Figure 2A:
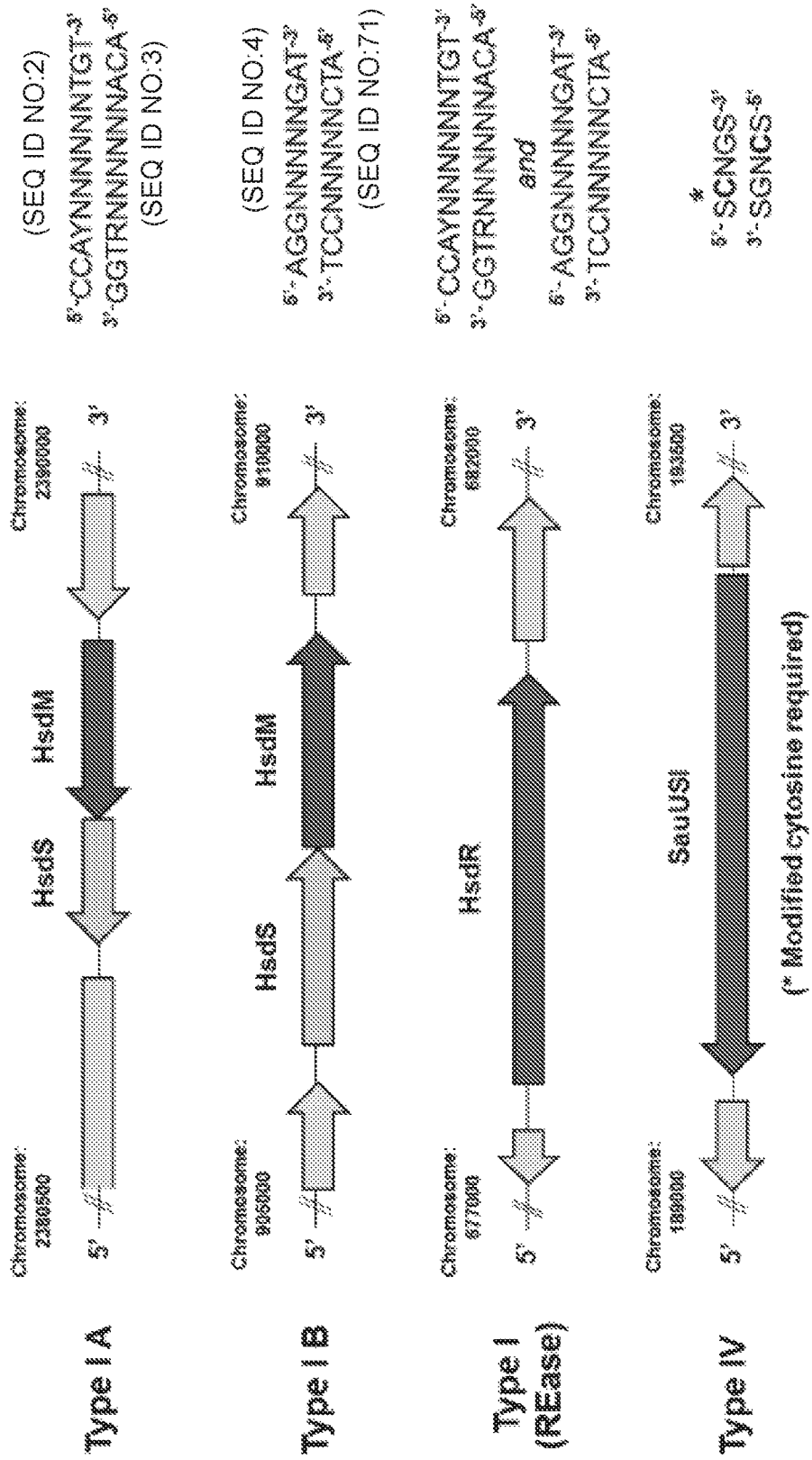
FIGS. 2A-2D show the SyngenicDNA approach applied to *Staphylococcus aureus* JE2.

Accordingly, in various embodiments, SMRTseq-generated methylome data is used to identify active RM systems, and infer the specific target recognized by the restriction endonuclease of each system. In a bacterial genome, a methylated motif represents either an RM system's target recognition sequence methylated by a methyltransferase to protect the site from its cognate restriction endonuclease, or a modification introduced by an orphan methyltransferase, which lacks a cognate restriction endonuclease and may be involved in regulatory activity (Murphy J, et al., (2013) Bacteriophage orphan DNA methyl transferases: insights from their bacterial origin, function, and occurrence. *Applied and environmental microbiology* 79(24):7547-7555). To differentiate between these two possibilities, the quantitative SMRTseq methylome data is evaluated. An active RM system methylates approximately 100% of its target motifs in the genome, because unmethylated motifs are substrates for the cognate restriction endonuclease, which introduces chromosomal breaks resulting in bacterial cell death (Takahashi N, et al., (2002) *Journal of bacteriology* 184(22):6100-6108; Kobayashi I (1998) *Trends Genet* 14(9):368-374). Allowing for a small margin of incomplete post-replicative methylation in actively dividing cells during DNA isolation, a sequence can be assumed to be a target recognition sequence for an active RM system if, in some embodiments, at least 95% of the motifs are methylated. Therefore, in some embodiments, the methods described herein include determining a methylated motif is a target recognition sequence for an active RM system if at least 95% of the motifs are methylated (FIG. 2A). In further embodiments, a methylated motif is determined to be a target recognition sequence for an active RM system if at least 97% of the motifs are methylated. In yet further embodiments, a methylated motif is determined to be a target recognition sequence for an active RM system if at least 99% of the motifs are methylated.

A REBASE analysis, as described further below, is used to confirm suspected orphan methyltransferases (Roberts R J, et al., (2015) REBASE—a database for DNA restriction and modification: enzymes, genes and genomes. *Nucleic Acids Res* 43(Database issue):D298-299). Thus, in some embodiments, methods of the present disclosure further comprise confirming that a methyltransferase is an orphan. In embodiments, confirming that a methyltransferase is an orphan comprises determining that a restriction endonuclease gene homolog with the same target site is detected no less than 10 genes away from the methyltransferase, based on genomic coordinates (Johnston C D, et al., (2017) *PLoS One* 12(9):e0185234; Seshasayee A S N, et al., (2012)

*Nucleic acids research* 40(15):7066-7073). Thus, a concise list of the target sequences of a strain's active RM systems is generated in silico targets that need to be eliminated from the DNA sequence of the selected genetic tool.

Additional methods of determining the methylome of a bacteria strain of interest and methods for preparing a modified nucleic acid molecule are known in the art. For example, see WO 2018/071841, the entire content, and in particular the relevant disclosure, of which is hereby incorporated by reference.

Figure 2B:
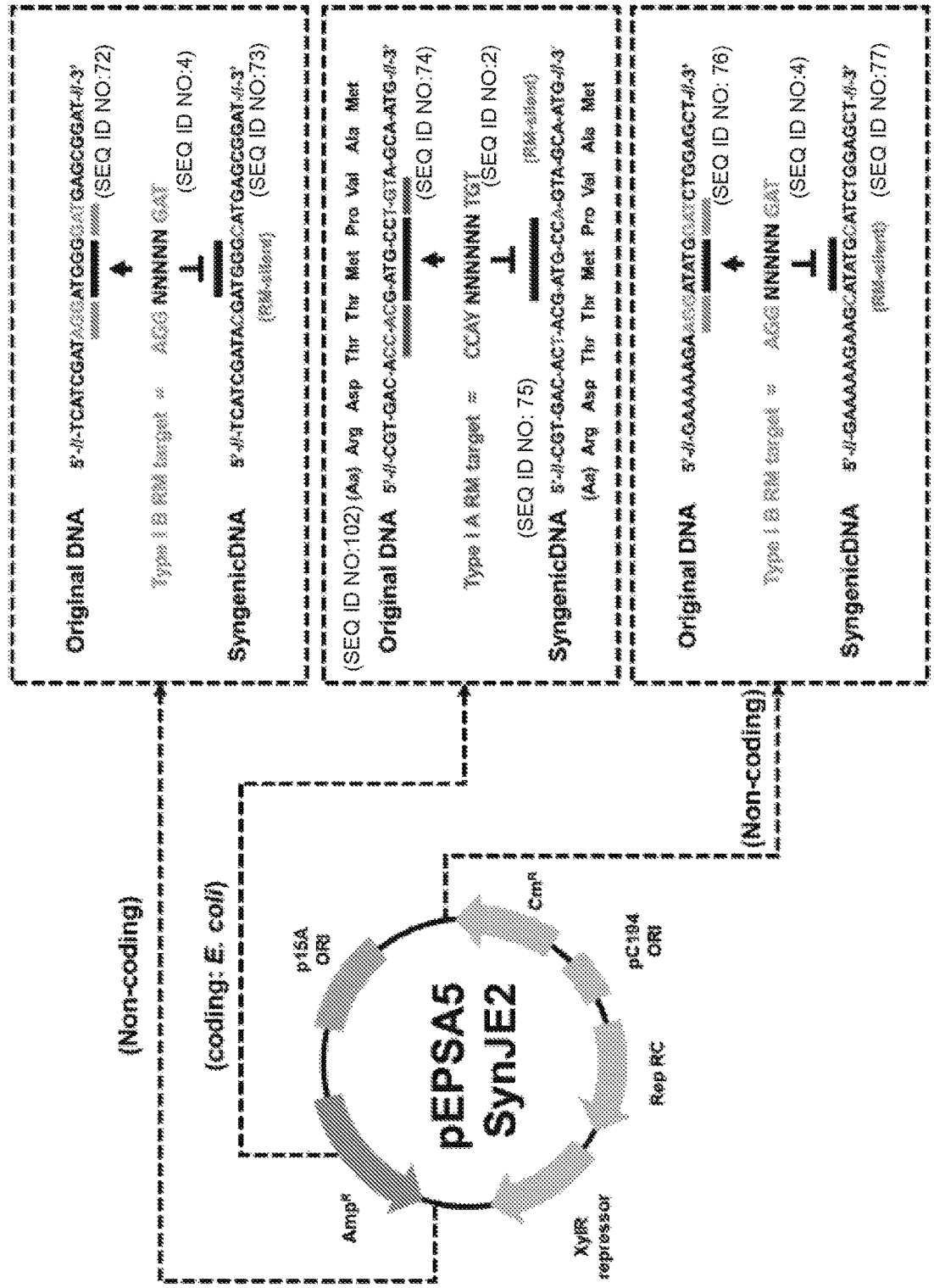

In various embodiments, methods of the present disclosure further comprise an in silico sequence adaptation of a genetic tool comprising an exogenous nucleic acid molecule to be transformed into a bacterium. The frequency with which an RM target occurs in the DNA sequence of a genetic tool depends on the length and base composition (GC vs AT content) of the target motif. As discussed above, target motifs vary greatly in sequence and length, ranging from 4-18 base pairs (bp), with >450 different motifs identified to date (Roberts R J, et al., (2015) *Nucleic Acids Res* 43(Database issue):D298-299). RM systems are classified into four types (Type I, II, III, and IV), based on their target motifs recognized and, also, their subunit composition, cleavage position, cofactor requirements, and substrate specificity (Vasu K, et al., (2013) *Microbiol Mol Biol Rev* 77(1):53-72). Type I-III systems, with exceptions, recognize and cut a target sequence if it lacks an appropriate methyl group. Characteristically, Type I systems target discontinuous bipartite DNA motifs comprising two specific half-sequences separated by a nonspecific spacer gap of 6 to 8 bp. One of the best characterized examples is the EcoKI system that recognizes $AACN_6GTGC$, where N is any base, (SEQ ID NO:1) (Murray N E (2000) *Microbiol Mol Biol Rev* 64(2):412-434). Type II systems are a conglomeration of many different subsystems that target both continuous and noncontinuous motifs ranging from 4 bp (e.g., AGCT of the AluI system (Zhang B, et al., (1993) Nucleic acids research 21(4):905-911)) to 15 bp (e.g., $CCAN_9TGG$ of the XcmI system (Gormley N A, et al., (2000) *Journal of Biological Chemistry* 275(10):69286936)). Type III systems recognize short continuous asymmetric targets ranging from 4 bp (e.g., CGCC of the TmeBIV system (Roberts R J, et al., (2015) *Nucleic Acids Res* 43(Database issue):D298-299)) to 7 bp (e.g., AGCCGCC of the Bpe1371 system (Roberts R J, et al., (2015) *Nucleic Acids Res* 43(Database issue):D298-299)). Type I-III RM system targets that occur within non-coding regions can be eliminated readily using single nucleotide polymorphisms (SNPs), whereas those that occur in coding regions require synonymous codon switches (FIG. 2B).

Many genetic tools are dual host-range plasmids (i.e., shuttle vectors) composed of two different functional replicons (origin of replication and accessory genes) permitting them to operate in multiple bacterial species (usually a laboratory strain of *E. coli* and another desired host species). The activity of the two replicons is usually partitioned depending on the bacterial host strain. The *E. coli* replicon is active when propagating the genetic tool in *E. coli* while the other replicon remains inactive until transferred to the desired host strain, whereupon the *E. coli* replicon then becomes inactive.

Notably, bacteria use synonymous codons at unequal frequencies, with some favored over others by natural selection for translation efficiency and accuracy, known as codon bias (Ermolaeva M D (2001) *Curr Issues Mol Biol* 3(4):91-97). Therefore, to avoid the introduction of rare or unfavorable codons when eliminating RM targets within a genetic tool in silico, in embodiments, methods of the present disclosure further comprise distinguishing on which replicon each target motif is present and introducing synonymous substitutions corresponding to the codon bias of that specific host. Codon bias can be determined by annotation and analysis of the host's genome generated by SMRTseq.

Figure 9A:
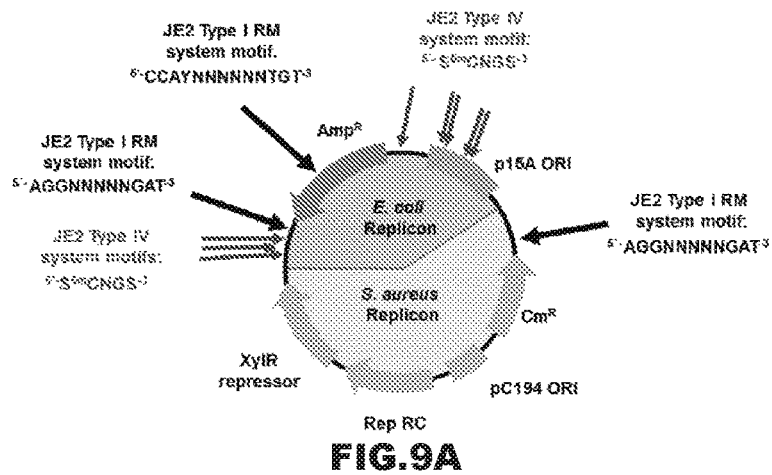
FIGS. 9A-9B show the schematic of pEPSA5 plasmid with *S. aureus* JE2 RM targets and construction of pEPSA5SynJE2.

For example, the pEPSA5 plasmid (Forsyth R A, et al. (2002) *Mol Microbiol* 43(6):1387-1400) is an *E. coli-S. aureus* shuttle vector containing a 2.5 kb *E. coli* replicon (ampicillin-resistance gene and low copy number pl5a origin for autonomous replication) and a 4.3 kb *S. aureus* replicon (chloramphenicol-resistance gene, pC194-derived origin, and a xylose repressor protein gene, xylR) (FIG. 9A). The *S. aureus* replicon is nonfunctional when pEPSA5 is maintained and propagated within *E. coli*, and vice versa. Therefore, RM targets that occur within a coding region of the pEPSA5 *E. coli* replicon are modified with synonymous substitutions adhering to *E. coli* codon bias that is known in the art and described herein. Additionally, if an RM target motif corresponds to a commercially available methyltransferase enzyme, in vitro methylation (downstream of de novo synthesis) rather than elimination of such targets via nucleotide substitution could be used. This would decrease the total number of necessary substitutions and reduce the likelihood of introducing unfavorable alterations. However, of the motifs identified to date, only 37 of these targets are represented by available methyltransferase enzymes. Furthermore, only 16 of those available commercially are isolated methyltransferase enzymes that are useful for in vitro DNA methylation (Table 6). The remaining 21 enzymes exist as RM complexes, with methyltransferase and restriction endonuclease subunits that compete for enzymatic modification and restriction activities, respectively (Roberts R J, et al., (2015) REBASE—a database for DNA restriction and modification: enzymes, genes and genomes. *Nucleic Acids Res* 43(Database issue):D298-299). Nevertheless, in cases where an methyltransferase is available, all other RM targets could be eliminated in silico to generate a genetic tool, followed by in vitro methylation prior to transformation.

Figure 2D:
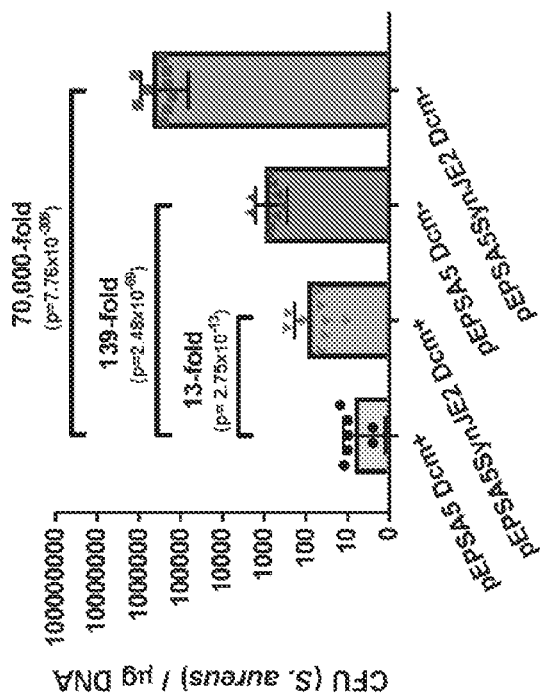
Figure 2C:
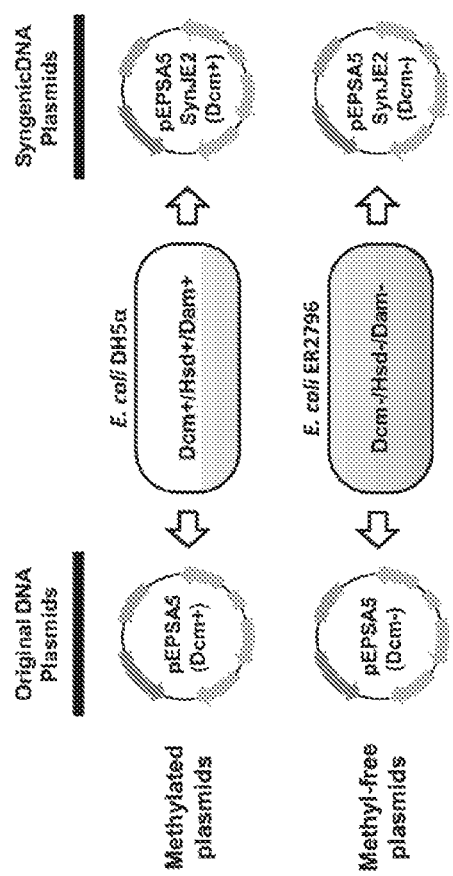

In contrast to Type I-III systems detailed above, Type IV restriction systems lack methyltransferases and instead are composed of methyl-dependent restriction endonuclease enzymes that only cleave DNA sequences with methylated, hydroxymethylated, or glucosyl-hydroxymethylated bases within their short target motifs. These systems are exemplified by the *Staphylococcus aureus* system SauUSI (Xu S Y, et al. (2011) *Nucleic Acids Res* 39(13):5597-5610) (FIG. 2A); a modified cytosine restriction system targeting $S^{5m}CNGS$ (either $^{m5}C$ or $^{5hm}C$) where S is C or G. The presence of such systems in a bacterial host have significant implications for genetic engineering due to their repressive effect on transformation efficiency (FIG. 2D). It is relatively simple to detect the presence of a Type IV system in a genome by screening for homologs to the putative Type IV restriction endonucleases in REBASE (Roberts R J, et al., (2015) *Nucleic Acids Res* 43(Database issue):D298-299). However, identification of Type IV system target motifs is inherently more difficult than for Type I-III systems because their targets motifs cannot be determined through SMRTseq and methylome analysis owing to the absence of an indicative epigenetic modification on host genomic DNA (Johnston C D, et al. (2017) PLoS One 12(9):e0185234). Nevertheless, the unintentional activation of Type IV systems can be avoided by the propagation of SyngenicDNA based tools in an intermediate *E. coli* host that does not methylate DNA (Dam-, Dcm-, HsdRMS-) (Anton B P, et al. (2015) *PLoS One* 10(5):e0127446), thus avoiding recognition and degradation by any Type IV systems present. As such, the systematic identification of the specific RM barriers present within a bacterial host facilitates the development of a tailored strategy to evade these barriers during genetic engineering. Once developed, this strategy can then be reapplied to create additional SyngenicDNA based genetic tools for the same host strain.

Kits

The present disclosure further provides kits that can be used to produce differentially methylated (e.g., methylation-free) MCs. Such kits comprise: an engineered, MC-producing bacterium as described herein. In embodiments, the kits further comprise written instructions for using the engineered, MC-producing bacterium to produce differentially methylated MCs. In various embodiments, the written instructions can be in the form of printed instructions provided within the kit, or the written instructions can be printed on a portion of the container housing the kit. Written instructions may be in the form of a sheet, pamphlet, brochure, CD-Rom, or computer-readable device, or can provide directions to locate instructions at a remote location, such as a website. The written instructions may be in English and/or in a national or regional language.

Such kits can further comprise one or more additional reagents, assay controls, or other supplies necessary for producing MCs, such as ampules, vials, tubes, tubing, pipettes, facemasks, a needleless fluid transfer device, sponges, sterile adhesive strips, Chloraprep, gloves, and the like. Variations in contents of any of the kits described herein can be made. In various embodiments, content of the kit is provided in a compact container.

EMBODIMENTS

Various embodiments of the disclosure are described herein. It will be recognized that features specified in each embodiment may be combined with other specified features to provide further embodiments of the present disclosure.

1. An engineered bacterium comprising:
a parental plasmid comprising a minicircle nucleic acid sequence comprising an exogenous nucleic acid sequence,
wherein the engineered bacterium is deficient in at least one endogenous methyltransferase such that the engineered bacterium has reduced DNA-methylation capability.

2. An engineered bacterium comprising:
a minicircle plasmid comprising an exogenous nucleic acid sequence,
wherein the engineered bacterium is deficient in at least one endogenous methyltransferase such that the engineered bacterium has reduced DNA-methylation capability.

3. The engineered bacterium of embodiment 1 or 2, wherein the exogenous nucleic acid sequence lacks methylation at a plurality of methylation cites that would be methylated in a reference bacterium of the same species as the engineered bacterium.

4. The engineered bacterium of any one of embodiments 1-3, wherein the engineered bacterium comprises a modification in a gene encoding a respective endogenous methyltransferase of the at least one endogenous methyltransferase.

5. The engineered bacterium of any one of embodiments 1-4, wherein the modification in the gene encoding the respective endogenous methyltransferase of the at least endogenous methyltransferase produces a truncated methyltransferase.

6. The engineered bacterium of any one of embodiments 1-5, wherein the at least one endogenous methyltransferase methylates a cytosine residue of a sequence CCWGG, wherein the W is A or T.

7. The engineered bacterium of any one of embodiments 1-6, wherein the at least one endogenous methyltransferase methylates an adenosine residue of a sequence GATC, a sequence $AACN_6GTGC$, or both.

8. The engineered bacterium of any one of embodiments 1-7, wherein the at least one endogenous methyltransferase methylates a cytosine residue and an adenosine residue.

9. The engineered bacterium of any one of embodiments 1-8, wherein the at least one endogenous methyltransferase comprises a Dam methyltransferase, a Dcm methyltransferase, an HsdM methyltransferase, or a combination thereof.

10. The engineered bacterium of embodiment 9, wherein the at least one endogenous methyltransferase comprises the Dam methyltransferase.

11. The engineered bacterium of any one of embodiments 9 or 10, wherein the at least one endogenous methyltransferase comprises the Dcm methyltransferase.

12. The engineered bacterium of any one of embodiments 9-11, wherein the at least one endogenous methyltransferase comprises the HsdM methyltransferase.

13. The engineered bacterium of any one of embodiments 9-12, wherein the at least one endogenous methyltransferase comprises the Dam methyltransferase and the Dcm methyltransferase.

14. The engineered bacterium of any one of embodiments 9-13, wherein the at least one endogenous methyltransferase comprises the Dam methyltransferase and the HsdM methyltransferase.

15. The engineered bacterium of any one of embodiments 9-14, wherein the at least one endogenous methyltransferase comprises the Dcm methyltransferase and the HsdM methyltransferase.

16. The engineered bacterium of any one of embodiments 9-15, wherein the at least one endogenous methyltransferase comprises the Dam methyltransferase, the Dcm methyltransferase, and the HsdM methyltransferase.

17. The engineered bacterium of any one of embodiments 9-16, wherein the Dam methyltransferase is absent.

18. The engineered bacterium of any one of embodiments 9-16, wherein the Dam methyltransferase is non-functional.

19. The engineered bacterium of any one of embodiments 9-18, wherein the Dcm methyltransferase is absent.

20. The engineered bacterium of any one of embodiments 9-18, wherein the Dcm methyltransferase is non-functional.

21. The engineered bacterium of any one of embodiments 9-20, wherein the HsdM methyltransferase is absent.

22. The engineered bacterium of any one of embodiments 9-20, wherein the HsdM methyltransferase is non-functional.

23. The engineered bacterium of any one of embodiments 1-22, wherein the engineered bacterium is *Escherichia coli*.

24. The engineered bacterium of any one of embodiments 1 or 3-23, wherein the parental plasmid comprises a plurality of restriction sites outside of the minicircle nucleic acid sequence.

25. The engineered bacterium of any one of embodiments 1-24, further comprising an inducible ΦC31 integrase.

26. The engineered bacterium of embodiment 25, wherein the inducible ΦC31 integrase is induced by arabinose.

27. The engineered bacterium of any one of embodiments 1-26, further comprising an inducible I-SceI homing endonuclease.

28. The engineered bacterium of embodiment 27, wherein the inducible I-SceI homing endonuclease is induced by arabinose.

29. A kit comprising an engineered bacterium of any one of embodiments 1-28.

30. A minicircle (MC) plasmid produced from an engineered bacterium of any one of embodiments 1-28 or from a kit of embodiment 29.

31. A method, comprising:
producing a minicircle comprising an exogenous DNA sequence in a first bacterium that is an engineered bacterium of any one of embodiments 1-28; and
transforming the minicircle into a second bacterium, the minicircle resisting degradation when transformed into the second bacterium.

32. The method of embodiment 31, further comprising engineering the first bacterium, such that the first bacterium is deficient in the at least one endogenous methyltransferase.

33. The method of embodiment 32, wherein the engineering comprises editing the gene encoding the at least one methyltransferase by CRISPR-mediated recombineering.

34. A method, comprising:
transforming a parental plasmid into an engineered bacterium that is deficient in at least one endogenous methyltransferase, the parental plasmid comprising a minicircle nucleic acid sequence comprising an exogenous nucleic acid sequence; and
producing a minicircle comprising the minicircle nucleic acid sequence.

35. The method of embodiment 34, wherein the exogenous nucleic acid sequence lacks methylation at a plurality of methylation cites that would be methylated in a reference bacterium of the same species as the engineered bacterium.

36. The method of embodiment 34 or 35, wherein the engineered bacterium comprises a modification in a gene encoding a respective endogenous methyltransferase of the at least one endogenous methyltransferase.

37. The method of any one of embodiments 34-36, wherein the modification in the gene encoding the respective endogenous methyltransferase of the at least endogenous methyltransferase produces a truncated methyltransferase.

38. The method of any one of embodiments 34-37, wherein the at least one endogenous methyltransferase methylates a cytosine residue of a sequence CCWGG, wherein the W is A or T.

39. The method of any one of embodiments 34-38, wherein the at least one endogenous methyltransferase methylates an adenosine residue of a sequence GATC, a sequence $AACN_6GTGC$, or both.

40. The method of any one of embodiments 34-39, wherein the at least one endogenous methyltransferase methylates a cytosine residue and an adenosine residue.

41. The method of any one of embodiments 34-40, wherein the at least one endogenous methyltransferase comprises a Dam methyltransferase, a Dcm methyltransferase, an HsdM methyltransferase, or a combination thereof.

42. The method of embodiment 41, wherein the at least one endogenous methyltransferase comprises the Dam methyltransferase.

43. The method of any one of embodiments 41 or 42, wherein the at least one endogenous methyltransferase comprises the Dcm methyltransferase.

44. The method of any one of embodiments 41-43, wherein the at least one endogenous methyltransferase comprises the HsdM methyltransferase.

45. The method of any one of embodiments 41-44, wherein the at least one endogenous methyltransferase comprises the Dam methyltransferase and the Dcm methyltransferase.

46. The method of any one of embodiments 41-45, wherein the at least one endogenous methyltransferase comprises the Dam methyltransferase and the HsdM methyltransferase.

47. The method of any one of embodiments 41-46, wherein the at least one endogenous methyltransferase comprises the Dcm methyltransferase and the HsdM methyltransferase.

48. The method of any one of embodiments 41-47, wherein the at least one endogenous methyltransferase comprises the Dam methyltransferase, the Dcm methyltransferase, and the HsdM methyltransferase.

49. The method of any one of embodiments 38-48, wherein the Dam methyltransferase is absent.

50. The method of any one of embodiments 38-48, wherein the Dam methyltransferase is non-functional.

51. The method of any one of embodiments 38-50, wherein the Dcm methyltransferase is absent.

52. The method of any one of embodiments 38-50, wherein the Dcm methyltransferase is non-functional.

53. The method of any one of embodiments 38-52, wherein the HsdM methyltransferase is absent.

54. The method of any one of embodiments 38-52, wherein the HsdM methyltransferase is non-functional.

55. The method of any one of embodiments 34-54, wherein the engineered bacterium is *Escherichia coli*.

56. The method of any one of embodiments 34-55, wherein the parental plasmid comprises a plurality of restriction sites outside of the minicircle nucleic acid sequence.

57. The method of any one of embodiments 34-56, wherein the engineered bacterium further comprises an inducible ΦC31 integrase.

58. The method of embodiment 57, wherein the inducible ΦC31 integrase is induced by arabinose.

59. The method of any one of embodiments 34-58, wherein the engineered bacterium further comprises an inducible I-SceI homing endonuclease.

60. The method of embodiment 59, wherein the inducible I-SceI homing endonuclease is induced by arabinose.

61. A host cell, comprising:
a plasmid comprising a nucleic acid sequence that is exogenous to the host cell,
wherein the exogenous nucleic acid sequence lacks methylation at a plurality of methylation cites that would be methylated in a reference *Escherichia coli* bacterium.

62. The host cell of embodiment 61, wherein the plasmid lacks a bacterial origin of replication.

63. The host cell of embodiment 61, wherein the plasmid lacks an antibiotic resistance marker.

64. The host cell of any one of embodiments 61-63, wherein the plasmid is a mini-circle.

65. The host cell of embodiment 61, wherein the plasmid is a parental plasmid.

66. The host cell of embodiment 65, wherein the parental plasmid comprises a bacterial origin of replication, an antibiotic resistance marker, or both.

67. An engineered minicircle-producing bacterium that is deficient in at least one methyltransferase and thereby has reduced DNA-methylation capability.

68. The engineered bacterium of embodiment 67, wherein the at least one methyltransferase is selected from the group consisting of Dam, Dcm, and HsdM.

69. The engineered bacterium of embodiment 67, wherein the bacterium does not methylate at a cytosine residue of a sequence CCWGG in a DNA, wherein the W is A or T.

70. The engineered bacterium of embodiment 67, wherein the bacterium does not methylate at an adenosine residue of a sequence GATC or a sequence AACN$_6$GTGC or of both sequences in a DNA.

71. The engineered bacterium of embodiment 67, wherein the bacterium does not methylate at both a cytosine residue and an adenosine residue in a DNA.

72. The engineered bacterium of embodiment 67, wherein the bacterium is missing a Dam methyltransferase or has non-functional Dam methyltransferase.

73. The engineered bacterium of embodiment 67, wherein the bacterium is missing a Dcm methyltransferase or has non-functional Dcm methyltransferase.

74. The engineered bacterium of embodiment 67, wherein the bacterium is missing an HsdM methyltransferase or has non-functional HsdM methyltransferase.

75. The engineered bacterium of embodiment 67, wherein the bacterium is missing a Dam methyltransferase and a Dcm methyltransferase.

76. The engineered bacterium of embodiment 67, wherein the bacterium is missing a Dam methyltransferase, a Dcm methyltransferase and HsdM methyltransferase.

77. The engineered bacterium of embodiment 67, wherein the gene encoding the at least one methyltransferase is edited by CRISPR-mediated recombineering.

78. The engineered bacterium of embodiment 67, wherein the bacterium is *Escherichia coli*.

79. A kit for producing methylation-free minicircle plasmids comprising an engineered bacterium of embodiments 1-78.

80. A minicircle (MC) plasmid produced from an engineered bacterium of embodiments 67-78 or from a kit of embodiment 79.

81. A method for generating an exogenous DNA that resists degradation when transformed into a bacterium of interest, the method comprising:
producing minicircle plasmids from an engineered bacterium of any one of embodiments 67-78 wherein the minicircle plasmids comprise the exogenous DNA; and
transforming the minicircle plasmids into the bacterium of interest.

Embodiments of this invention are further illustrated by the following examples.

Embodiments of the present disclosure include an engineered bacterium comprising a parental plasmid comprising a minicircle nucleic acid sequence comprising an exogenous nucleic acid sequence, wherein the engineered bacterium is deficient in at least one endogenous methyltransferase such that the engineered bacterium has reduced DNA-methylation capability.

The present disclosure further includes embodiments of an engineered bacterium comprising: a minicircle plasmid comprising an exogenous nucleic acid sequence, wherein the engineered bacterium is deficient in at least one endogenous methyltransferase such that the engineered bacterium has reduced DNA-methylation capability.

In embodiments, the exogenous nucleic acid sequence lacks methylation at a plurality of methylation cites that would be methylated in a reference bacterium of the same species as the engineered bacterium.

In embodiments, the engineered bacterium comprises a modification in a gene encoding a respective endogenous methyltransferase of the at least one endogenous methyltransferase. In some embodiments, the modification in the gene encoding the respective endogenous methyltransferase of the at least endogenous methyltransferase produces a truncated methyltransferase.

In additional embodiments, the at least one endogenous methyltransferase methylates a cytosine residue of a sequence CCWGG, wherein the W is A or T. In various embodiments, the at least one endogenous methyltransferase methylates an adenosine residue of a sequence GATC, a sequence AACN$_6$GTGC, or both. In some embodiments, the at least one endogenous methyltransferase methylates a cytosine residue and an adenosine residue.

In further embodiments, the at least one endogenous methyltransferase comprises a Dam methyltransferase, a Dcm methyltransferase, an HsdM methyltransferase, or a combination thereof. In various embodiments, the at least one endogenous methyltransferase comprises the Dam methyltransferase and the Dcm methyltransferase. In various embodiments, the at least one endogenous methyltransferase comprises the Dam methyltransferase and the HsdM methyltransferase. In various embodiments, the at least one endogenous methyltransferase comprises the Dcm methyltransferase and the HsdM methyltransferase. In particular embodiments, the at least one endogenous methyltransferase comprises the Dam methyltransferase, the Dcm methyltransferase, and the HsdM methyltransferase. In specific embodiments, the Dam methyltransferase is absent. In other embodiments, the Dam methyltransferase is non-functional. In additional embodiments, the Dcm methyltransferase is absent. In other embodiments, the Dcm methyltransferase is non-functional. In still further embodiments, the HsdM methyltransferase is absent. In alternate embodiments, the HsdM methyltransferase is non-functional.

In embodiments, the engineered bacterium is *Escherichia coli*. In some embodiments, the parental plasmid comprises a plurality of restriction sites outside of the minicircle nucleic acid sequence. In particular embodiments, the engineered bacterium further comprises an inducible ΦC31 integrase. In specific embodiments, the inducible ΦC31 integrase is induced by arabinose. In further embodiments, the engineered bacterium further comprises an inducible I-SceI homing endonuclease. In particular embodiments, the inducible I-SceI homing endonuclease is induced by arabinose.

Additional embodiments of the disclosure include a kit comprising an engineered bacterium described herein. Also described herein are a minicircle (MC) plasmid produced from an engineered bacterium or a kit described herein.

Embodiments of the present disclosure further include a host cell, comprising: a plasmid comprising a nucleic acid sequence that is exogenous to the host cell, wherein the exogenous nucleic acid sequence lacks methylation at a plurality of methylation cites that would be methylated in a reference *Escherichia coli* bacterium.

In some embodiments, the plasmid lacks a bacterial origin of replication. In some embodiments, the plasmid lacks an antibiotic resistance marker. In particular embodiments, the plasmid is a mini-circle. In other embodiments, the plasmid is a parental plasmid. In some embodiments, the parental plasmid comprises a bacterial origin of replication, an antibiotic resistance marker, or both.

Further described herein is a method, comprising:
producing a minicircle comprising an exogenous DNA sequence in a first bacterium that is an engineered bacterium described herein; and
transforming the minicircle into a second bacterium, the minicircle resisting degradation when transformed into the second bacterium.

In various embodiments, the method further comprises engineering the first bacterium, such that the first bacterium is deficient in the at least one endogenous methyltransferase.

In additional embodiments, the engineering comprises editing the gene encoding the at least one methyltransferase by CRISPR-mediated recombineering.

The present disclosure further describes a method, comprising: transforming a parental plasmid into an engineered bacterium that is deficient in at least one endogenous methyltransferase, the parental plasmid comprising a minicircle nucleic acid sequence comprising an exogenous nucleic acid sequence; and producing a minicircle comprising the minicircle nucleic acid sequence.

In various embodiments, the exogenous nucleic acid sequence lacks methylation at a plurality of methylation cites that would be methylated in a reference bacterium of the same species as the engineered bacterium.

In some embodiments, the engineered bacterium comprises a modification in a gene encoding a respective endogenous methyltransferase of the at least one endogenous methyltransferase. In some embodiments, the modification in the gene encoding the respective endogenous methyltransferase of the at least endogenous methyltransferase produces a truncated methyltransferase.

In particular embodiments, the at least one endogenous methyltransferase methylates a cytosine residue of a sequence CCWGG, wherein the W is A or T. In specific embodiments, the at least one endogenous methyltransferase methylates an adenosine residue of a sequence GATC, a sequence $AACN_6GTGC$, or both. In certain embodiments, the at least one endogenous methyltransferase methylates a cytosine residue and an adenosine residue.

In various embodiments, the at least one endogenous methyltransferase comprises a Dam methyltransferase, a Dcm methyltransferase, an HsdM methyltransferase, or a combination thereof. In some embodiments, the at least one endogenous methyltransferase comprises the Dam methyltransferase. In some embodiments, the at least one endogenous methyltransferase comprises the Dcm methyltransferase. In some embodiments, the at least one endogenous methyltransferase comprises the HsdM methyltransferase. In certain embodiments, the at least one endogenous methyltransferase comprises the Dam methyltransferase and the Dcm methyltransferase. In particular embodiments, the at least one endogenous methyltransferase comprises the Dam methyltransferase and the HsdM methyltransferase. In some embodiments, the at least one endogenous methyltransferase comprises the Dcm methyltransferase and the HsdM methyltransferase. In specific embodiments, the at least one endogenous methyltransferase comprises the Dam methyltransferase, the Dcm methyltransferase, and the HsdM methyltransferase.

In various embodiments, the Dam methyltransferase is absent. In other embodiments, the Dam methyltransferase is non-functional. In various embodiments, the Dcm methyltransferase is absent. In other embodiments, the Dcm methyltransferase is non-functional. In various embodiments, the HsdM methyltransferase is absent. In other embodiments, the HsdM methyltransferase is non-functional.

In further embodiments, the engineered bacterium is *Escherichia coli*. In various embodiments, the parental plasmid comprises a plurality of restriction sites outside of the minicircle nucleic acid sequence. In some embodiments, the engineered bacterium further comprises an inducible ΦC31 integrase. In particular embodiments, the inducible ΦC31 integrase is induced by arabinose. In some embodiments, the engineered bacterium further comprises an inducible I-SceI homing endonuclease. In certain embodiments, the inducible I-SceI homing endonuclease is induced by arabinose.

EXAMPLES

Genetic engineering is a powerful approach for discovering fundamental aspects of bacterial physiology, metabolism, and pathogenesis as well as for harnessing the capabilities of bacteria for human use. However, the full power of genetic engineering can only be applied to a few model organisms. Biological diversity and strain-level variation in restriction-modification systems are critical barriers keeping most bacteria beyond the full potential of genetics. The present disclosure provides a systematic approach to effectively evade restriction-modification systems that can be applied broadly to any cultivated bacterium. The results herein demonstrate the simplicity and effectiveness of this stealth-by-engineering approach, which will enable microbial genetic system design not restrained by innate defense mechanisms.

Figure 11:
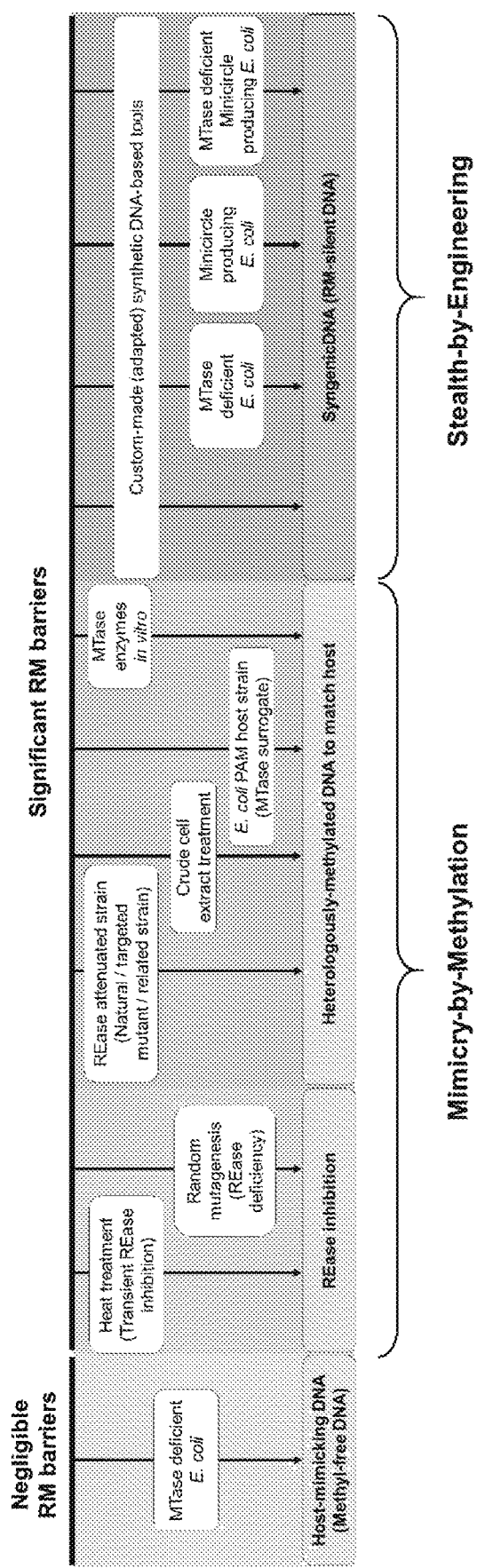
FIG. 11 shows approaches to overcome RM system-mediated genetic barriers in bacteria [adapted from (Suzuki H (2012) *Biochemistry, Genetics and Molecular Biology* Chapter 9)]. Current approaches modify the methylation pattern of a genetic tool, either in vitro or ex vivo, to match that of the desired host to achieve mimicry by methylation. In contrast, SyngenicDNA methods evade RM systems by eliminating their target recognition sequences from DNA to create minimalistic RM-silent genetic tools, and achieve stealth-by-engineering during transformation.

The present disclosure provides an approach to circumvent the most common cause of genetic intractability, RM barriers, during microbial genetic engineering. In contrast to current mimicry-by-methylation approaches, the present disclosure involves stealth-by-engineering (FIG. 11). As described further in the following examples, the precise targets of the RM systems within a poorly tractable (or intractable) bacterial strain were identified and eliminated from the DNA sequence template of a genetic tool in silico via single nucleotide polymorphisms (SNPs) or synonymous nucleotide modifications. Thus, a tailor-made version of the genetic tool that is RM-silent with respect to the specific host was synthesized. This stealth-based SyngenicDNA approach provides genetic tools to that efficiently operate in bacteria with active RM defenses.

Additionally, minicircle technology was used to generate SyngenicDNA minicircle plasmid (SyMPL) tools, which are free from components required for propagation in *E. coli* but superfluous in the target host. Using a clinically relevant USA300 strain of *S. aureus*, a profound improvement in transformation efficiency was achieved by systematic evasion of RM systems using these SyngenicDNA and SyMPL approaches described herein.

The following materials and methods are used in Examples 1-4.

Microbial Strains and Reagents.

*E. coli* NEBalpha competent cells were purchased from New England Biolabs (NEB) and used as intermediate cloning hosts. *E. coli* ER2796 was provided by the laboratory of Rich Roberts (NEB) and used to produce methylation-free plasmid DNA. *E. coli* MC (ZYCY10P3S2T; original minicircle-producing strain) was purchased from System Biosciences (SBI). Antibiotics and chemicals were purchased from Millipore-Sigma (St. Louis, MO) (Kanamycin, ampicillin, chloramphenicol, spectinomycin, isopropyl-D thiogalactopyranoside; IPTG) or Cayman Chemicals (Anhydrotetracycline). Growth media were purchased from Millipore-Sigma (Luria—Bertani, Brain Heart Infusion) or Oxoid (Vegetable Peptone). DNA isolation kits were purchased from Lucigen (Masterpure Gram Positive kit) and Qiagen (QIAprep Spin Miniprep Kit). Cloning reagents and DNA enzymes were purchased from NEB (Phusion High-Fidelity DNA Polymerase, HiFi DNA Assembly Master Mix, Q5 Site-Directed Mutagenesis Kit, EpiMark Bisulfite Conversion Kit) or Takara (EpiTaq HS for bisulfite-treated DNA). Plasmids were purchased from System Biosciences (SBI) (Parental plasmid; pMC vector), Elitra Pharmaceuticals (pEPSA5), Addgene (pCas; plasmid #42876, pTargetF; #62226) or obtained from the laboratory of George Church, Harvard University (pCKTRBS (Juarez J F, et al., (2017) bioRxiv:193029)) or Rich Roberts, NEB (pRRS). Oligonucleotides were purchased from IDT Technologies (Coralville, IA). Electroporation cuvettes (1 mm-gap) were purchased from BioRad and transformations performed on a BioRad Gene Pulser instrument. De novo DNA synthesis services and nucleic acid molecule fragments were purchased from Synbio Technologies (Monmouth Junction, NJ). Plasmid DNA sequencing services were purchased from Macrogen (Cambridge, USA) or the DNA core at the Center for Computational and Integrative Biology, Massachusetts General Hospital (Cambridge, MA).

Single Molecule, Real-Time Sequencing (SMRTseq) and Restriction-Modification (RM) System Identification.

SMRTseq of *S. aureus* JE2 was carried out on a PacBioRSII (Pacific Biosciences; Menlo Park, CA, USA) with P6/C4 chemistry at the Johns Hopkins Deep Sequencing & Microarray Core Facility, following standard SMRTbell template preparation protocols for base modification detection and SMRTanalysis v2.3.0 patch 5 (PACBIO®).

The principle of single molecule, real-time sequencing (SMRTseq) and related base modification detection has been detailed previously (Flusberg B A, et al. (2010) *Nat Methods* 7(6):461-465). SMRTseq was carried out on a PacBioRSII (Pacific Biosciences; Menlo Park, CA, USA) with P6/C4 chemistry at the Johns Hopkins Deep Sequencing & Microarray Core Facility, following standard SMRTbell template preparation protocols for base modification detection (PACBIO®). Genomic DNA samples were sheared to an average size of 20 kbp via G-tube (Covaris; Woburn, MA, USA), end repaired and ligated to hairpin adapters prior to sequencing. Sequencing reads were processed and mapped to respective reference sequences using the BLASR mapper (Pacific Biosciences) and the Pacific Biosciences' SMRTAnalysis pipeline using the standard mapping protocol. Interpulse durations were measured and processed for all pulses aligned to each position in the reference sequence. To identify modified positions, Pacific Biosciences' SMRTanalysis v2.3.0 patch 5, which uses an in silico kinetic reference and a t-test-based kinetic score detection of modified base positions, was used. Using SMRTseq data, RM system identification was performed essentially as previously described (Murray I A, et al. (2012) *Nucleic Acids Res* 40(22):1145011462), using the SEQWARE computer resource, a BLAST-based software module in combination with the curated restriction enzyme database (REBASE) (Roberts R J, et al., (2015) *Nucleic Acids Res* 43(Database issue):D298-299). Prediction was supported by sequence similarity, presence, and order of predictive functional motifs, in addition to the known genomic context and characteristics of empirically characterized RM system genes within REBASE and enabled the reliable assignment of candidate methyltransferase genes to each specificity based on their RM types.

Bioinformatics and SyngenicDNA Adaptation in Silico.

DNA sequence analysis and manipulation was performed using the Seqbuilder and Seqman programs of the DNASTAR software package (DNASTAR, Madison, WI). Codon usage analyses and synonymous substitutions were determined using a combination of CodonW and the Codon Usage Database (Kazusa), and introduced within Seqbuilder to maintain the amino acid integrity of coding regions within *E. coli*. Clustal Omega (EMBL website) was used to align DNA and amino acid sequences from original ORFs and SyngenicDNA variants. Plasmid DNA (dsDNA) conversions from weight (m) to molarity (pmol) was performed with Promega BioMath Calculators (Promega®).

DNA Synthesis and Assembly of SyngenicDNA Plasmids.

Figure 9B:
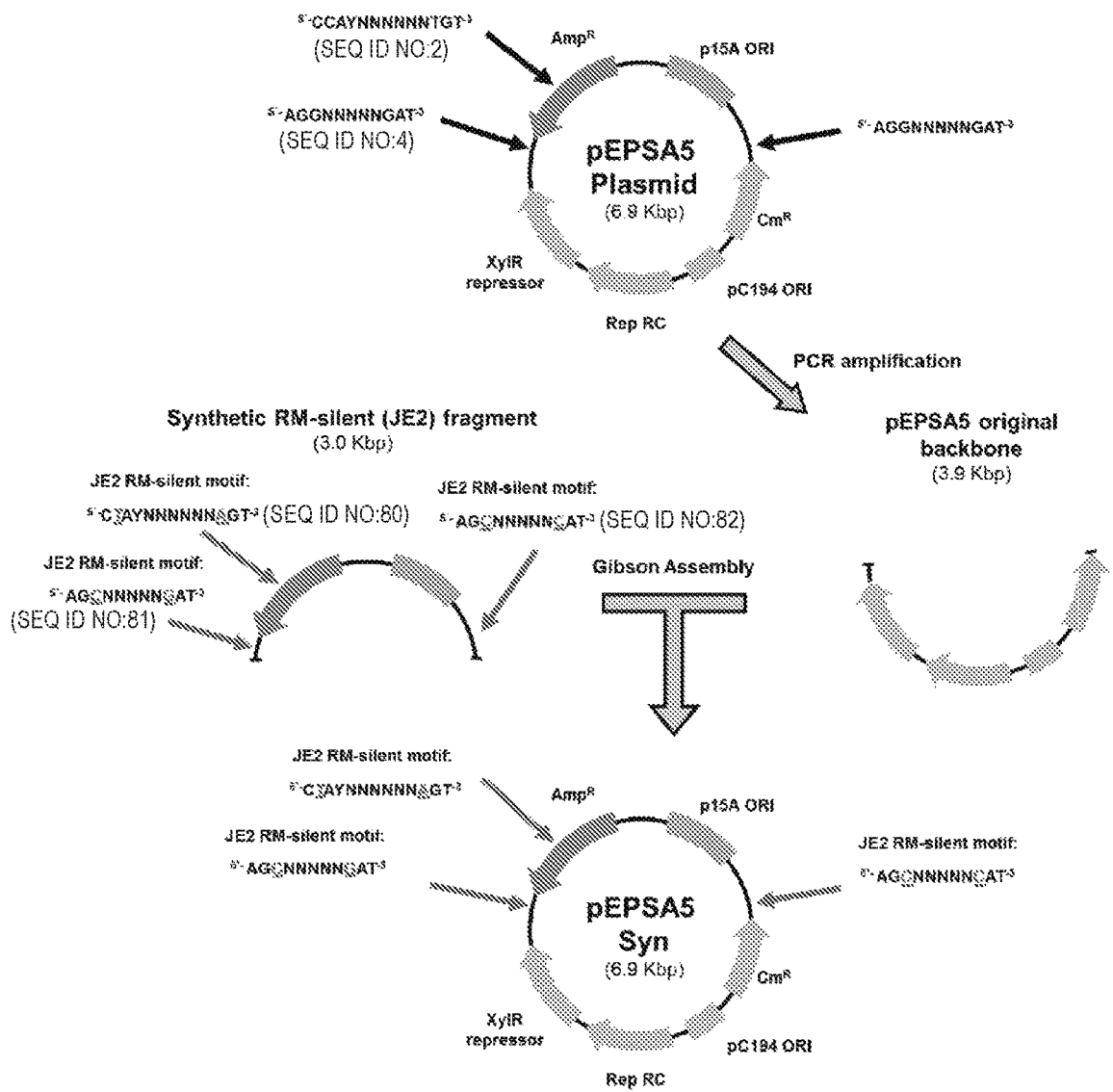

A SyngenicDNA-variant of the pEPSA5 plasmid (pEPSA5Syn) was assembled by replacing a 3.05 kb fragment of the original plasmid, encompassing three JE2 RM target sites, with a de novo synthesized DNA fragment that was RM-silent with respect to *S. aureus* JE2 (FIGS. 2, 9 and 10). Primers used are listed in Table 5. The original pEPSA5 plasmid was used as the amplification template for the unmodified backbone, while the plasmid pKan-Frag (Synbio Technologies) was used to amplify the modified RM-silent fragment. PCR amplicons were treated with DpnI to digest non-amplified template DNA and the pEPSA5SynJE2 plasmid was assembled using Gibson cloning. Plasmid nucleotide integrity was confirmed by resequencing. The pEPSA5 and pEPSA5SynJE2 plasmids were propagated within *E. coli* NEBalpha (Dam+/Dcm+/HsdM+) to produce methylated plasmid DNA or *E. coli* ER2796 (Dam−, Dcm−, HsdM−) to produce methylation-free plasmid DNA for evasion of Type IV RM systems. Methylation status of plasmid DNA was confirmed by DpnI treatment and agarose gel electrophoresis whereby only methylated plasmids were subject to digestion.

Genome Editing of *E. coli* MC-Producer Strain.

Figure 6A:
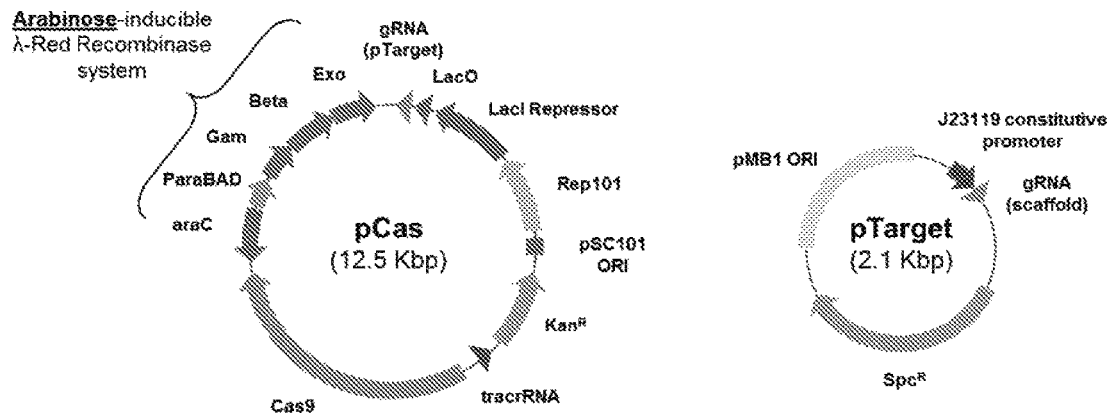
FIGS. 6A-6C provide the engineering of an anhydrotetracycline-inducible CRISPR-Cas9/λ-Red recombineering strategy for scarless deletion of methyltransferase genes within *E. coli* MC (ZYCY10P3S2T).

A CRISPR-Cas9/λ-Red multigene editing strategy was used to introduce scarless methyltransferase gene deletions in the *E. coli* MC strain (ZYCY10P3S2T). This strategy uses a two-plasmid system, pCas and pTarget (FIG. 6A), (see, Jiang Y, et al. (2015) *Appl Environ Microbiol* 81(7):2506-2514, the relevant disclosure of which is incorporated by reference. For the construction of a modified anhydrotetracycline inducible CRISPR-Cas9/λ-Red gene editing system, in the original system, the pCas plasmid maintains a constitutively expressed cas9 gene and an arabinose-inducible regulatory promoter/repressor module (araC-Pbad) controlling the λ-Red system (Gam, Beta, Exo), both present on a temperature sensitive replicon (repA101Ts). The compatible pTarget plasmid has a sgRNA scaffold for the desired Cas9-target under control of the constitutive promoter (J23119) and a pMB1 origin of replication.

Figure 6B:
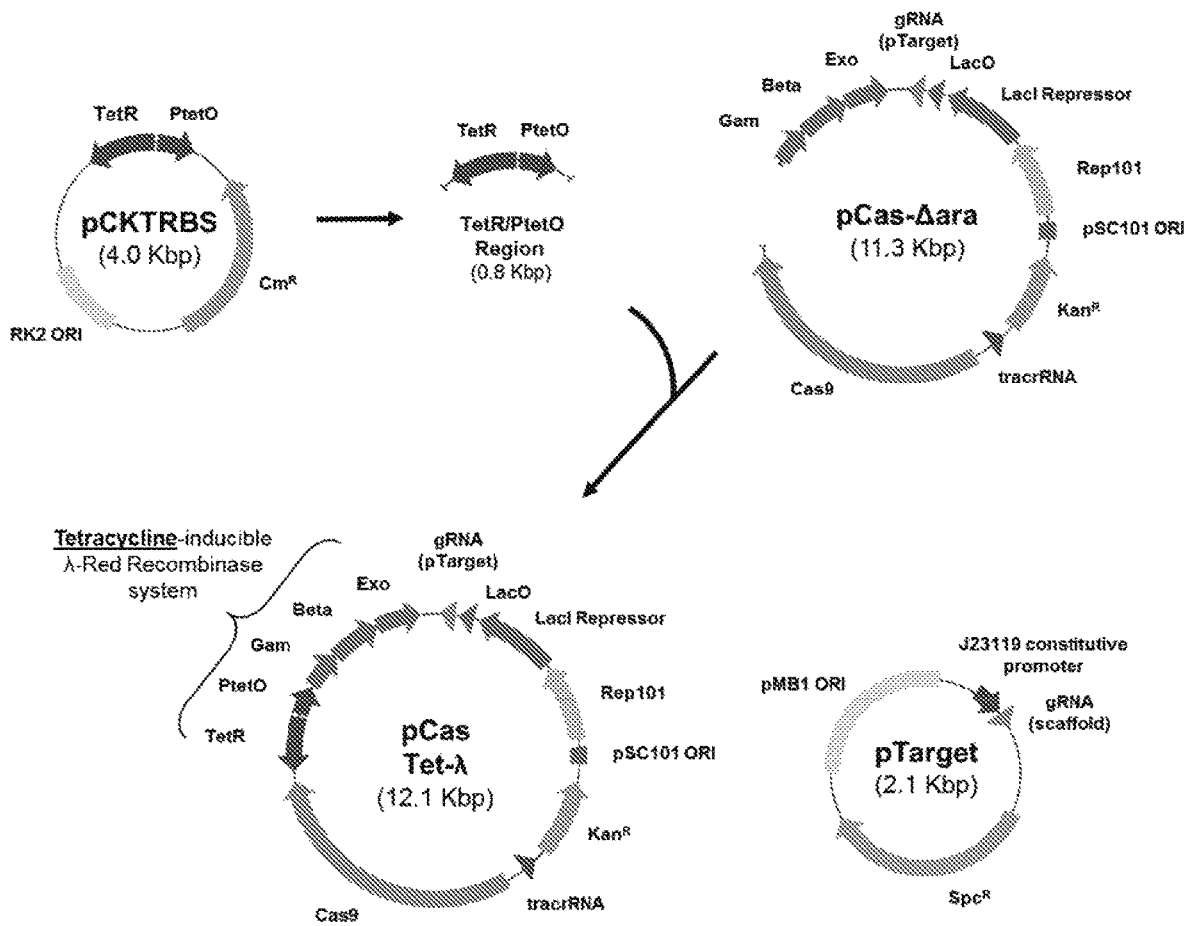

However, as MC formation within the *E. coli* MC strain is also regulated by chromosomally integrated araC-Pbad modules, arabinose induction of λ-Red recombination using the original system would cause unintentional induction of MC-assembly enzymes (the ΦC31 integrase and I-SceI homing endonuclease) during gene editing. To avoid this, the arabinose-inducible module of the λ-Red system was replaced with an alternative tetracycline-inducible module. Primers utilized are listed in Table 5. A 1318-bp region of pCas, upstream of the λ-Red gam gene, containing the araC-Pbad module was replaced with 818-bp tetracycline-inducible regulatory promoter/repressor unit (TetR/Ptet0) (FIG. 6B). The plasmid pCKTRBS served as template DNA for amplification of the TetR/PtetO module, which was spliced to an 11.3-kb amplicon of pCas (lacking the arabinose module) using Gibson assembly to form pCasTet-λ. The modified pCasTet-λ plasmid, in combination with the original pTarget, allowed for CRISPR-Cas9/λ-Red recombineering using anhydrotetracycline, a derivative of tetracycline that exhibits no antibiotic activity, instead of arabinose as an inducer molecule.

Figure 6C:
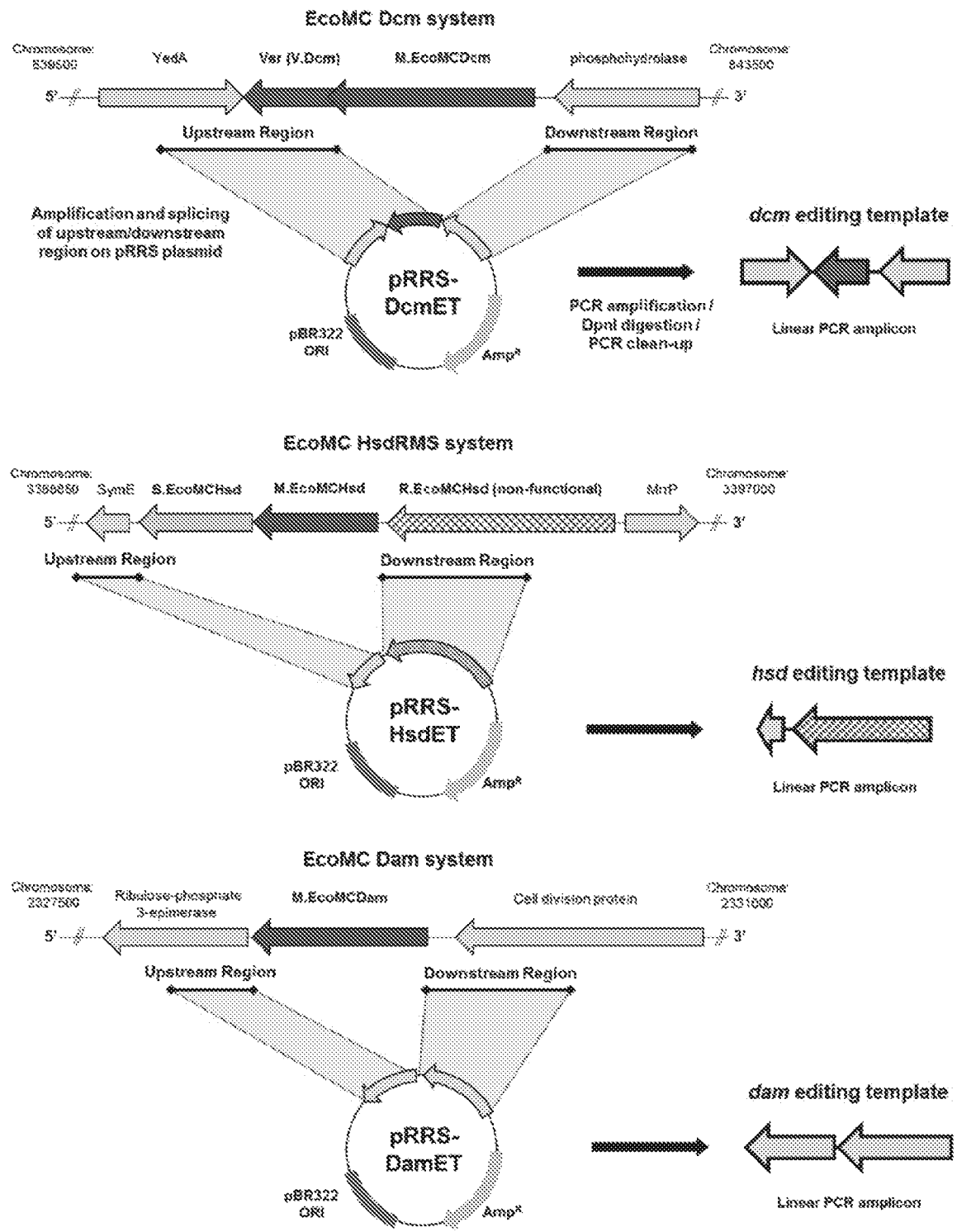
Figure 7:
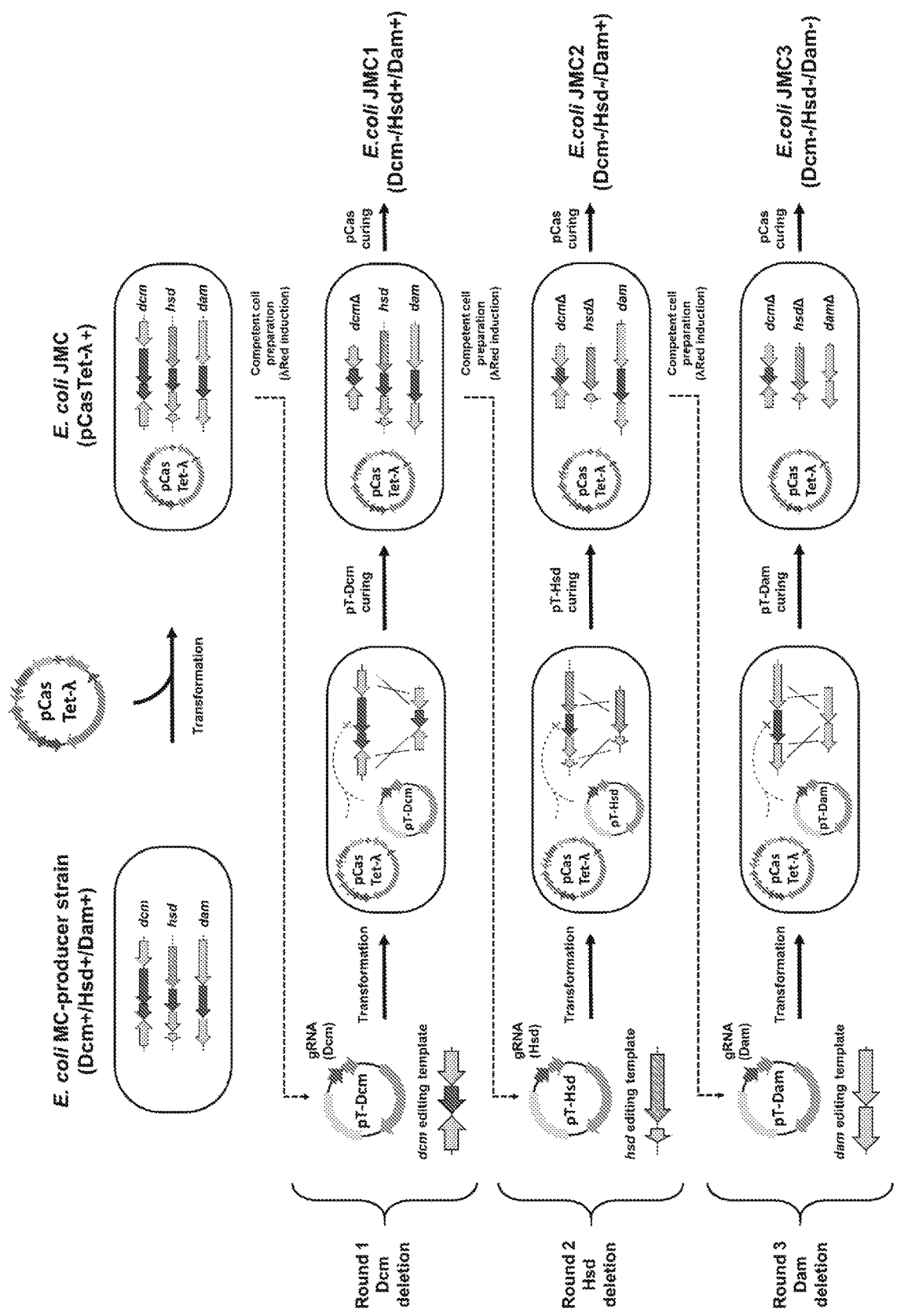
FIG. 7 shows the CRISPR-Cas9/λ-Red recombineering scheme used in *E. coli* MC (ZYCY10P3S2T) for scarless methyltransferase gene deletion. pTarget plasmids (pT-Dcm and pT-Hsd) each encode constitutively expressed gRNAs for Cas9-mediated targeting of methyltransferase genes in unsuccessfully edited cells. gRNA sequences used are included in Table 5.
Figure 8A:
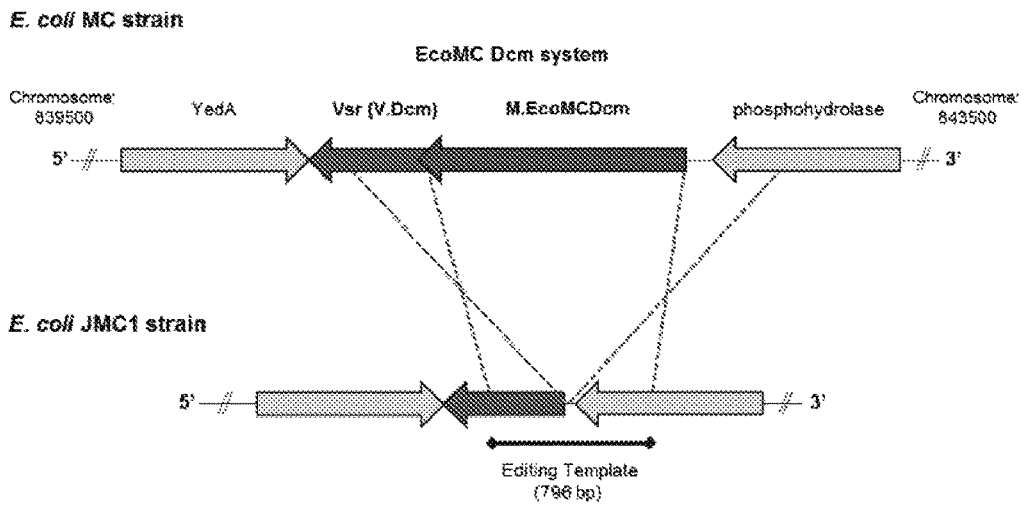
Figure 8B:
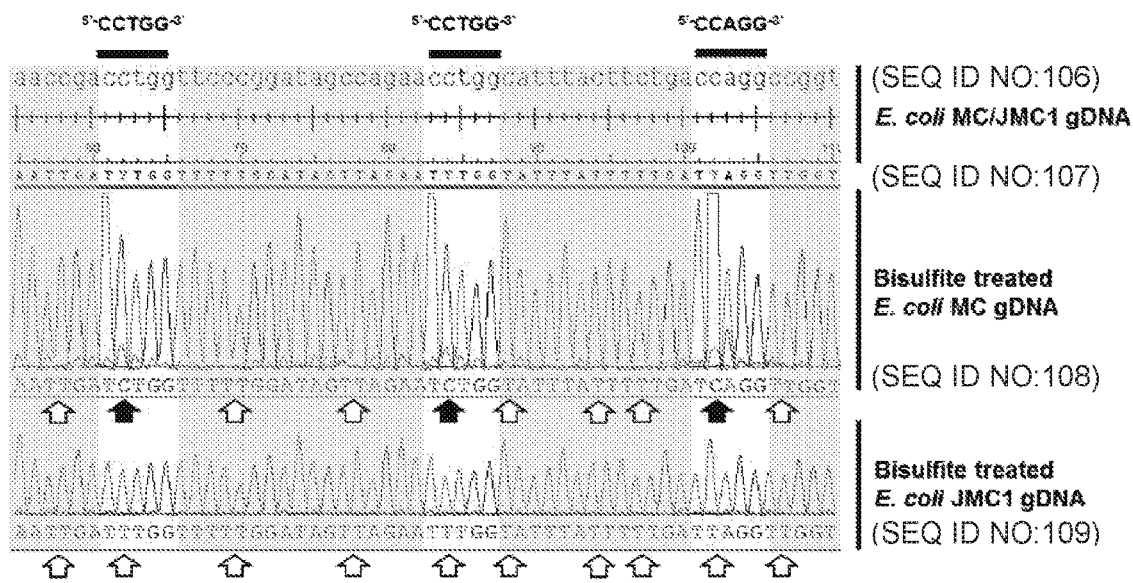
Figure 8C:
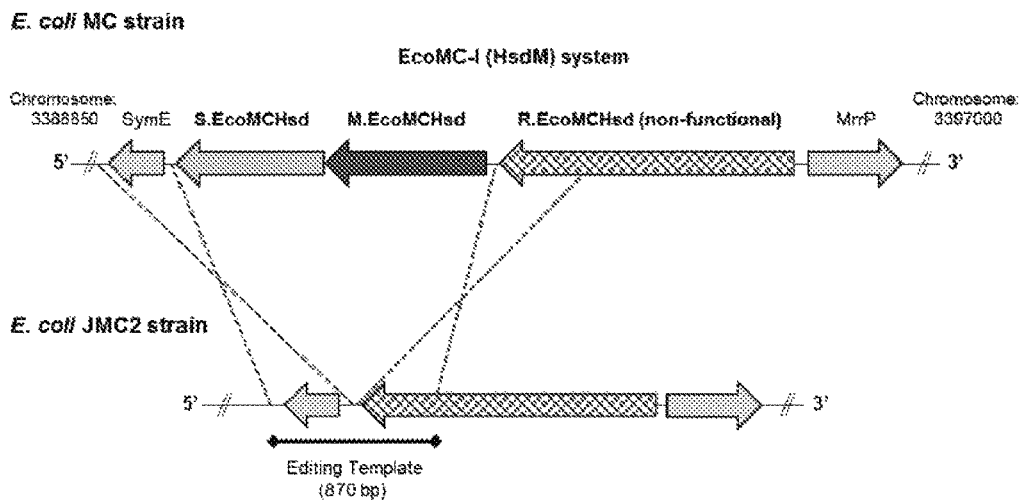

For the subsequent genome editing of the *E. coli* MC strain, the *E. coli* MC strain contains three active methyltransferases (Dcm+, Hsd+, Dam+) encoded by the Dcm, HsdMS, and Dam genes respectively. To create a suite of *E. coli* MC strains, each capable of producing MCs with different methylation signatures, these methyltransferase genes were sequentially deleted (in three-rounds) from the E. coli MC genome using a modified anhydrotetracycline-inducible CRISPR-Cas9/λ-Red recombineering strategy (FIGS. 6-8). In this strategy, λ-Red mediated recombination with a DNA editing template eliminates the methyltransferase gene from the chromosome, followed by CRISPR-Cas9 mediated targeting of the methyltransferase gene in unedited cells. Double-stranded DNA breaks introduced by CRISPR/Cas9 are toxic in bacteria, so only cells for which the target sequences have been edited can survive, allowing for positive selection of recombination events. methyltransferase deletion template plasmids were constructed by assembling PCR amplicons of regions 5' and 3' of each methyltransferase (reflecting the desired deletion event) onto a pRRS plasmid backbone (FIG. 6C). These pRRS-based template plasmids were then used to PCR amplify linear editing templates for λ-Red recombineering. To remove template plasmid-carryover during electrotransformation, editing template amplicons were DpnI treated and PCR purified prior to use.

E. coli MC competent cells (System Biosciences) were first transformed with pCasTet-λ to form E. coli JMC, which constitutively expressed the Cas9 protein but lacked a gRNA target (FIG. 7). JMC electrocompetent cells (harboring pCasTet-λ) were generated as previously described (Thomason L C, et al., (2007) Current protocols in molecular biology:1.16. 11-11.16. 39). For λ-Redinduction of JMC cells, anhydrotetracycline (200 ng/ml; ~0.5 µM) was added to the growing (30° C.) culture 30 min prior to making cells competent, as described for the arabinose-based system (Thomason L C, et al., (2007) Current protocols in molecular biology:1.16. 11-11.16. 39).

In the first round of genome editing, electrocompetent JMC cells were transformed with the Dcm-deletion editing template and pT-Dcm (pTarget with a single gRNA targeting the Dcm gene, under control of the J23119 constitutive promoter). For electroporation, 50 µl of cells were mixed with a 5 µl combination of 100 ng pT-Dcm plasmid and 200 ng Dcm-deletion editing template DNA; electroporation was performed in a 2-mm Gene Pulser cuvette (Bio-Rad) at 2.5 kV. Cells were recovered at 30° C. for 1 h before selective plating at 30° C. on LB agar containing kanamycin (50 µg/ml) and spectinomycin (50 µg/ml). Transformants were identified by colony PCR and DNA sequencing. Primers are listed in Table 5. After confirmation of Dcm deletion, the edited colony harboring both pCasTet-X, and pT-Dcm was cured of the latter plasmid by IPTG induction (0.5 mM), essentially as described previously (Jiang Y, et al. (2015) Appl Environ Microbiol 81(7):2506-2514). Briefly, IPTG induces the production of gRNA, which targets the origin of replication of pT-Dcm after interaction with the constitutively expressed Cas9 protein. This gRNA is encoded on the pCasTet-λ, plasmid under transcriptional control of the LacO/LacI (IPTG-inducible) system. The resulting E. coli strain, (DcmΔ/pCasTet-λ+) was made competent once again for the next round of editing, or cured of the pCasTet-λ, plasmid by incubation at 37° C. for four continuous inoculums, to form a plasmid-free minicircle producing strain E. coli JMC1 (Dcm−, HsdM+, Dam+).

In the second round of genome editing, the entire process was repeated targeting the Hsd methyltransferase system. E. coli DcmΔ/pCasTet-λ+ was transformed with the Hsd-deletion editing template and the pT-Hsd plasmid (pTarget with a single gRNA targeting the HsdM gene). The resulting E. coli strain, (DcmΔ, HsdMΔ, pCasTet-λ+) was cured of the pCasTet-λ, plasmid to form the E. coli JMC2 strain (Dcm−, HsdM+, Dam+).

In the third round, the entire process was repeated targeting the Dam methyltransferase system. E. coli Dcm−, HsdM−, pCasTet-λ+ was transformed with the Dam-deletion editing template and the pT-Dam plasmid (pTarget with a single gRNA targeting the Dam gene). The resulting E. coli strain (Dcm−, HsdM−, Dam−) was cured of both plasmids to form the completely methyl-free E. coli JMC3 strain (Dcm−, HsdM−, Dam−).

After each round of genome editing, the phenotypic effect of Dcm, HsdM, and Dam gene deletions were confirmed using bisulfite sequencing, SMRTseq, and methyl-dependent restriction enzyme analysis, respectively (FIG. 8). Site directed bisulfite sequencing and DpnI methyl-dependent restriction analysis of gDNA were performed essentially as described previously (Johnston C D, et al., (2017) PLoS One 12(9):e0185234).

Production of SyMPL Tools

The 4.3 kbp S. aureus replicon of both pEPSA5 plasmids (pEPSA5 and the pEPSA5SynJE2) were PCR amplified and spliced to the MC parental plasmid (pMC; Systems Biosciences) to form pEPSA5P and pEPSA5SynJE2P (P denotes parental). Primers listed in Table 5. To evade the Type IV restriction system of S. aureus JE2, which targets Dcm-methylated cytosine residues, Dcm-deficient MC-producing E. coli strain JMC1 (Dcm−, HsdM+, Dam+) was used. Competent plasmid-free E. coli JMC1 cells, prepared as described previously, were transformed with pEPSA5P and pEPSA5SynP. Minicircle induction and isolation was performed per manufacturers recommendations for the original E. coli MC strain (ZYCY10P3S2T). The resulting SyMPL tools pEPSA5MC and pEPSA5SynMC were eluted in high pure H$_2$O and normalized to 250 ng/µl prior to transformation. Plasmid nucleotide integrity was confirmed by resequencing.

S. aureus Transformations

Electrocompetent S. aureus JE2 cells were prepared using a modified version of that used by Löfblom et al. ((2007) Optimization of electroporation-mediated transformation: Staphylococcus carnosus as model organism. J Appl Microbioll 02(3):736-747). Briefly, overnight cultures of S. aureus JE2 (~0D600 nm=1.8) in vegetable peptone broth (VPB) were diluted to an OD600 nm of 0.25 in fresh prewarmed VPB. In initial experiments to test the efficacy of the SyngenicDNA method, cultures were grown at 37° C. with shaking (100 rpm) until they reached an OD600 nm between 0.8-0.95 (~3 hours). However, in the interim of SyngenicDNA experiments and SyMPL method experiments, increased JE2 cell competency was achieved when cultures were grown to an OD600 nm between 1.5-1.7 (~6 hours). Therefore, all SyMPL experiments were performed with cells harvested at this higher optical density. In both cases, when culture tubes reached the desired OD, culture flasks were chilled on wet ice for 15 min. Cells were harvested by centrifugation at 5000×g at 4° C. for 10 min, washed once in equal volumes of ice-cold sterile water and pelleted at 4° C. The cells were then washed in ⅒ volume ice-cold sterile 10% glycerol, repeated with ¹⁄₂₅ volume ice-cold sterile 10% glycerol, repeated with ¹⁄₁₀₀ volume ice-cold sterile 10% glycerol, resuspended in ¹⁄₁₆₀ volume of ice-cold sterile 10% glycerol and then aliquoted (250 µl) into 1.5 ml tubes. Electrocompetent cell aliquots were frozen at −80° C. until use.

For electroporation, a single aliquot was utilized for each individual experiment for accurate comparison of transformation efficiency between plasmids. The aliquot was thawed on ice for 5 min, transferred to room temperature for 5 min, centrifuged at 5000×g for 1 min and resuspended in 250 µl sterile electroporation buffer (10% glycerol, 500 mM sucrose). A 50 µl volume of competent cells was mixed with 1 µg plasmid DNA (250 ng/µl in sterile water) and added to a sterile 1 mm-gap electroporation cuvette. The cells were pulsed once using a Bio-Rad Gene Pulser System (settings: 25 µF, 100 Ω, 2.1 kV with a 2.3 millisec time constant) and outgrown in 1 ml of trypic soy broth with 500 mM sucrose for 1 hour at 37° C., diluted for spreading on trypic soy agar plates with 151 µg/ml Cm and incubated overnight at 37° C.

Scientific Rigor and Experimental Design

Transformation efficiencies (presented in FIGS. 2D and 2B) were determined based upon nine independent experiments. Three independent batches of electrocompetent *S. aureus* cells were prepared (Biological Replicate 1, 2, and 3; Table 2). Three aliquots from each batch of electrocompetent cells were used to perform three independent transformation experiments, typically on consecutive days (Technical Replicates A, B, and C; Table 2). A single plasmid preparation (for each pEPSA5 variant) was used for all technical replicates within a batch. A fresh plasmid preparation (for all pEPSA5 variants) was used for each new batch of cells to account for variation associated with plasmid propagation/isolation from *E. coli* strains and the effect of freeze-thaw on plasmid DNA. In independent experiments, a single 250 µl aliquot of electrocompetent *S. aureus* was used for all plasmids (50 µl/plasmid) within each of the nine experiments, so that data within technical replicates could be treated as paired, or "clustered" across the four plasmids, and plasmid transformation efficiencies could be compared validly and efficiently. The average of CFU counts from a minimum of three replicate agar plates was used when determining transformation efficiencies for individual plasmids within experiments.

Statistical Analysis

Statistical analyses were carried out using Graphpad Prism (version 7.04; GraphPad Software, San Diego, CA) and Stata version 12.1 (StataCorp. 2011. Stata Statistical Software: Release 12. College Station, Tex.: StataCorp LP). Means with standard error (SEM) are presented in each graph. As appropriate for count data, transformation efficiency across plasmids were compared by fitting negative binomial regression models with two-sided alpha=0.05 (Tables 3 and 4). A generalized estimating equations (GEE) framework and robust standard errors were used to account for clustering within technical replicates of competent cells. For each experiment designed as a 2×2 factorial design, main effects and multiplicative interaction terms (see Experimental Design) were fitted. This can be thought of as a difference-in-differences analysis, quantifying how the effect of one condition (e.g., SyngenicDNA plasmid versus unmodified plasmid) differs in the presence or absence of another condition (e.g., propagated in a Dcm+ or a Dcm– *E. coli* host).

Data Availability

Complete genome sequences and associated methylome annotations of *Staphylococcus aureus* USA300 JE2_Forsyth and *Escherichia coli* MC_Forsyth have been submitted to REBASE (http://rebase.neb.com/) for public release under organism #21742 and #21741, respectively. The nucleotide sequences of each plasmid used in this study are included in Table 7. Raw CFU colony count data for determination of transformation efficiencies, along with data for associated analyses, are presented in Tables 2-4.

Example 1

Systematic Generation of SyngenicDNA-Based Genetic Tools

There are four basic steps to produce SyngenicDNA-based genetic tools (FIG. 1A-1C): 1) target identification, 2) in silico tool assembly, 3) in silico sequence adaptation, and 4) DNA synthesis and assembly. Target identification requires the delineation of each methylated site, with single-base resolution, across an entire bacterial genome (i.e., the methylome) and starts with single molecule real-time (SMRT) genome and methylome sequencing (Johnston C D, et al., (2017) *PLoS One* 12(9):e0185234). Using methylome data, each of the recognition motifs protected by the methyltransferases of the host's RM systems were delineated and the targets recognized and degraded by their cognate restriction endonucleases were inferred, as described herein. This yields a concise list of a host microbes' RM targets to be eliminated from the DNA sequence of a selected genetic tool.

In silico tool assembly requires complete annotation of a genetic tool's sequence with respect to plasmid chassis, replication origins, antibiotic resistance cassettes, promoters, repressors, terminators and functional domains to avoid adverse changes to these structures during subsequent adaptation steps. Ideally, a complete and minimalistic genetic tool with previous demonstrable functionality in a genetically tractable strain is used for initial experiments, allowing for subsequent addition of DNA parts to increase functionality after successful transformation is achieved.

In silico sequence adaptation of the genetic tool is the most crucial step of the SyngenicDNA approach and it is here where the intrinsic evolutionary weakness of high target-sequence specificity present in all RM systems is exploited. Accordingly, in this step, the complete nucleotide sequence of the genetic tool is screened for the presence of RM targets identified by SMRTseq. Then the nucleotides of each RM target in silico are recoded to eliminate the target while preserving the functionality of the sequence. In non-coding regions, targets are removed changing a single nucleotide (creating a SNP). In coding regions, the sequence of the target is removed using synonymous codon substitution. A single nucleotide alteration is generally sufficient to remove RM targets, but multiple alterations can also be used. The preferential codon bias of the desired host is used to avoid introducing rare or unfavorable codons during the synonymous switch. Upon complete removal of all RM targets in silico, the recoded DNA sequence has been rendered RM-silent with respect to the host, termed SyngenicDNA, and ready for de novo DNA synthesis.

Figure 1B:
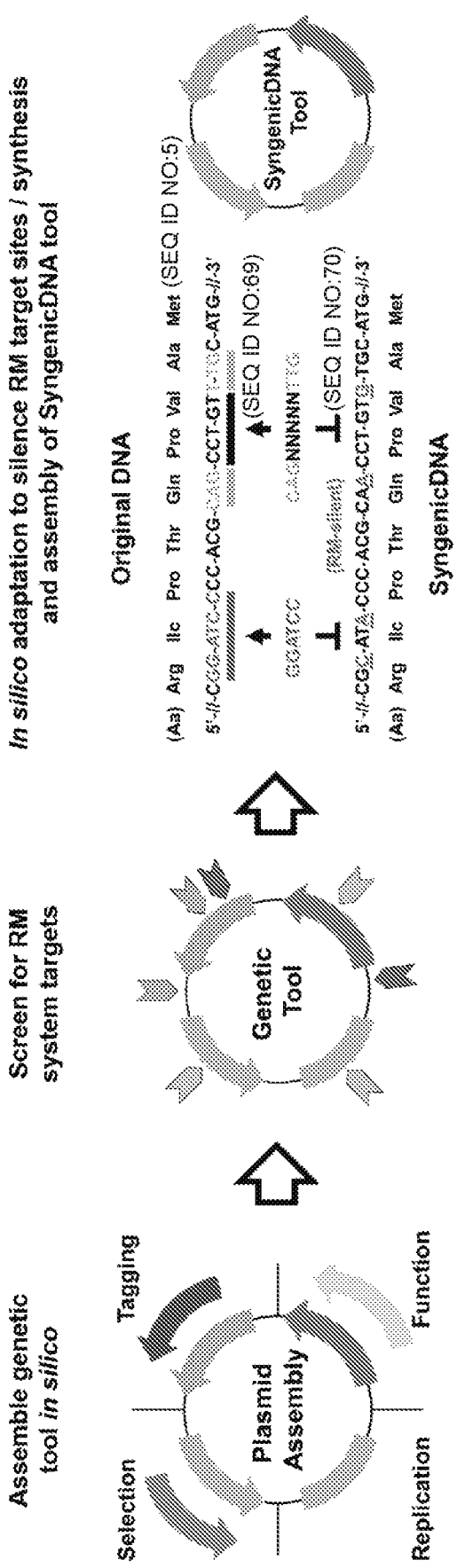
Figure 1C:
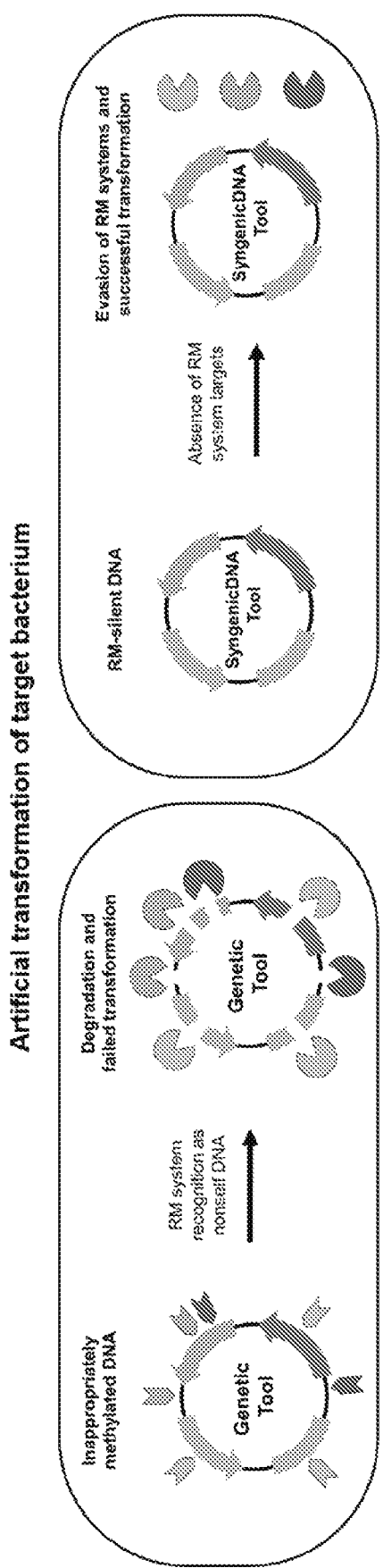

Synthesis and assembly of RM-silent genetic tools is carried out using commercially available de novo DNA synthesis and standard assembly approaches, ensuring that any laboratory can construct SyngenicDNA tools. During commercial DNA synthesis, nucleic acid sequences are typically cloned onto an *E. coli* plasmid replicon, which is propagated to yield large amounts of the synthetic DNA. This *E. coli* replicon is convenient but might include RM targets that could lead to degradation of the overall circular tool after transformation into the host species. Two solutions to this potential issue have been developed. One solution is to generate a SyngenicDNA *E. coli* plasmid backbone for each specific microbial host strain (FIG. 1B). However, in routine applications this will increase costs of SyngenicDNA synthesis and, moreover, the *E. coli* replicon itself becomes redundant after propagation in *E. coli*, as it is typically nonfunctional in other bacterial species after transformation. The alternative solution, therefore, is to remove the *E. coli* replicon entirely using minicircle DNA technology, rather than recode it. This approach also increases flexibility because the same *E. coli* replicon can be used to generate tools for multiple different microbial strains.

Example 2

SyngenicDNA Minicircle (MC) Plasmid (SyMPL) Tools

Figure 4A:
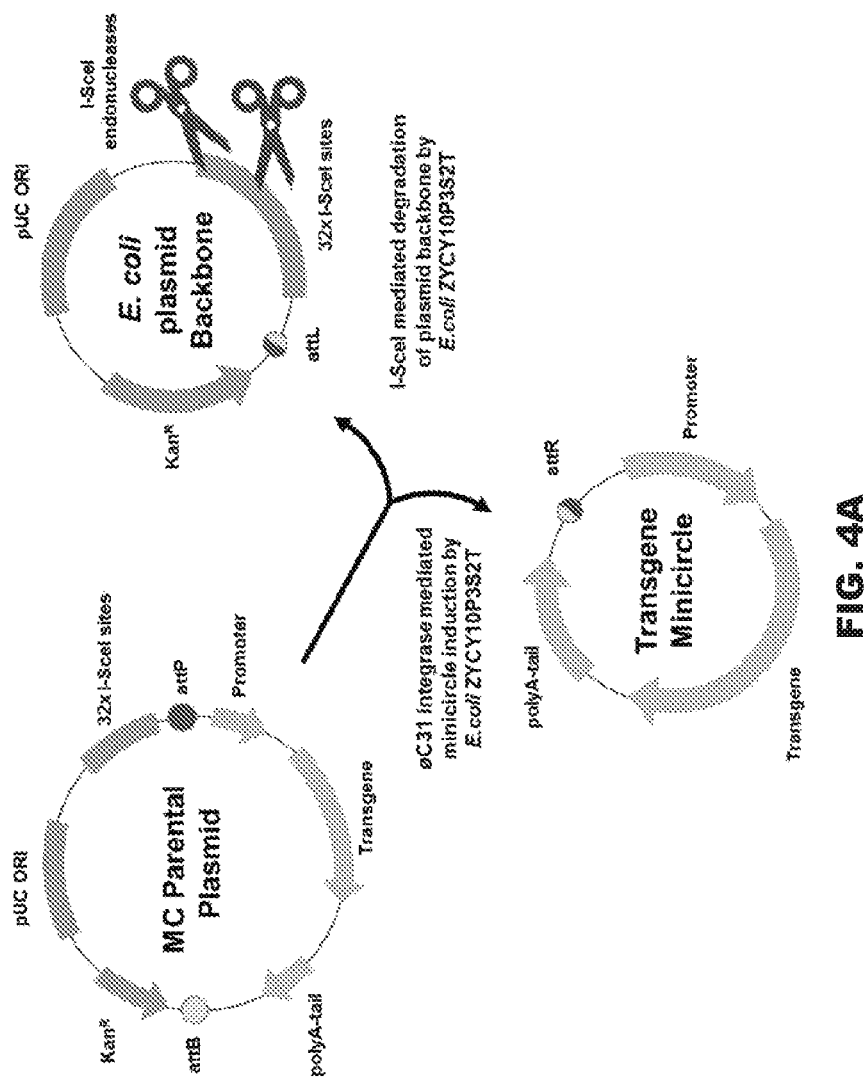
FIGS. 4A-4C describe the repurposing of MC technology to produce minimalistic genetic tools for application in bacteria.
Figure 4B:
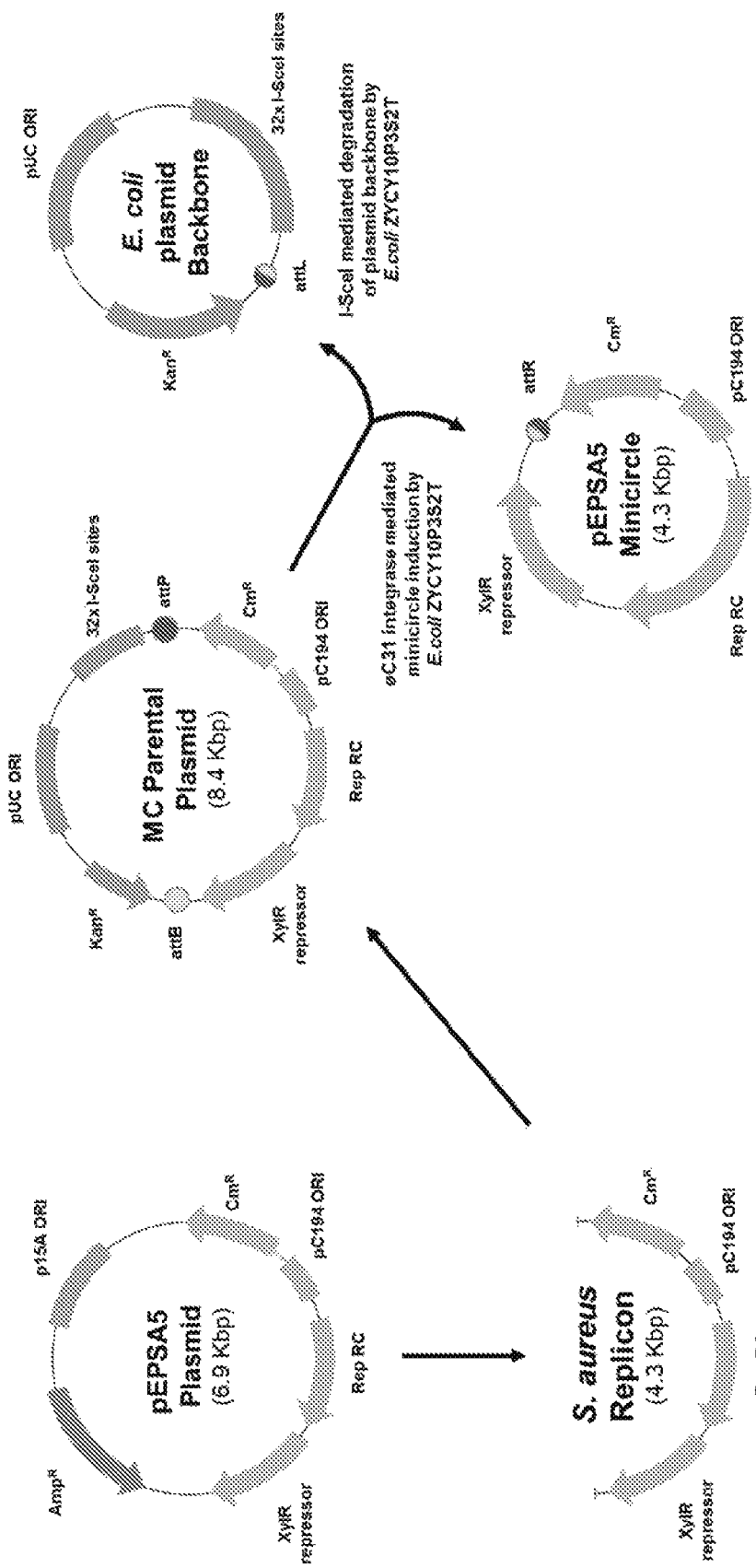
Figure 4C:
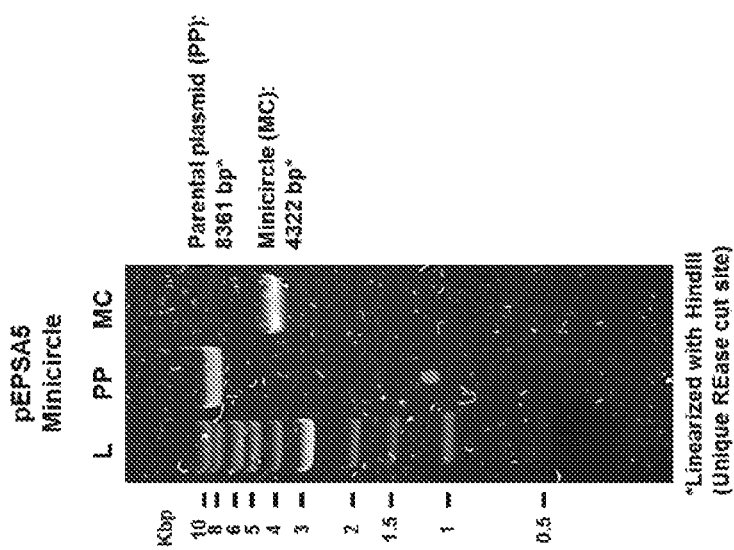

Minicircles (MCs) are minimalistic circular expression cassettes devoid of a plasmid backbone (Kay M A, et al. (2010) *Nat Biotechnol* 28(12):1287-1289). These are primarily used in gene therapy applications to drive stable expression of transgenes in eukaryotic hosts. MCs are produced by attaching a parental plasmid (PP) to a transgene cassette; cultivating this construct in an *E. coli* host grown to high-cell density; inducing construct recombination to form an isolated transgene on a MC and a separate, automatically degraded, PP containing the *E. coli* replicon; and, finally, purifying isolated MCs by using standard plasmid methods (Kay M A, et al. (2010) *Nat Biotechnol* 28(12): 1287-1289) (FIG. 4A). Because any DNA sequence can take the place of the transgene, the MC technology was repurposed to carry entire microbial plasmids and facilitate the removal of superfluous *E. coli* replicons from shuttle vectors. The incorporation of SyngenicDNA sequences into a PP allowed for the creation of syngenicDNA minicircle (MC) plasmid (SyMPL) tools (FIG. 4B). SyMPL tools include replication, selection, and functional domains for operation in a specific non-*E. coli* host, but lacking an *E. coli* replicon despite being isolated at high concentrations from the MC-producing *E. coli* strain. In the SyMPL strategy, a synthesized (and assembled) SyngenicDNA tool is attached to the non-SyngenicDNA *E. coli* PP, and this construct is propagated in a MC-producing *E. coli* strain. The induction of MCs via recombination, with concurrent induction of a specific endonuclease that eliminates the PP, allows for easy isolation of a minimalistic SyngenicDNA-based genetic tool ready to transform into the desired host strain (FIG. 4C).

Figures 5A, 5B:
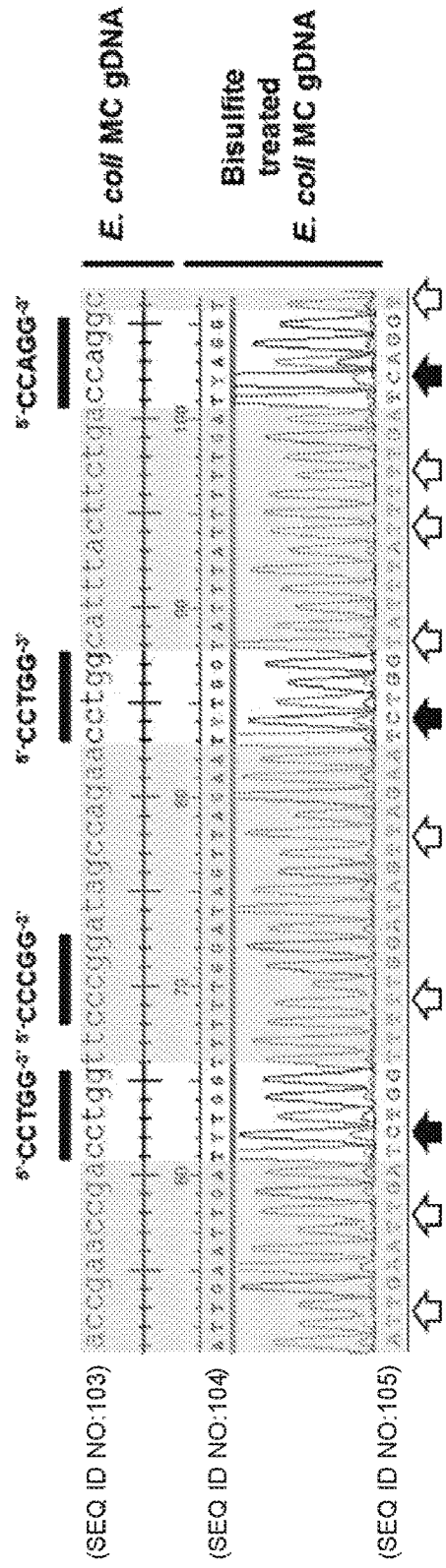

The majority of laboratory *E. coli* strains, including the MC-producing *E. coli* host used in this Example, contain three active methyltransferases (Dam, Dcm, and HsdM) that introduce methylation modifications to specific target sites on the host genome (FIG. 5A-5C). The Dam methyltransferase modifies the adenine residue (m$^6$A) within the sequence GATC, the Dcm methyltransferase modifies the internal cytosine residue (m$^5$C) of the sequence CCWGG (where W is A or T), and the HsdM methyltransferase modifies the internal adenine residue (m$^6$A) of the sequence AACN$_6$GTGC (SEQ ID NO:1). Therefore, plasmid tools propagated within such *E. coli* strains, including the minicircle (MC)-producing strain (ZYCY10P3S2T), are modified at these targets sequences.

The presence of methylated sites on SyngenicDNA-based tools could activate Type IV RM systems upon artificial transformation. Generally, unintentional activation of methyl-targeting Type IV systems is avoided by the propagation of plasmids within methyl-deficient *E. coli* strains such as JM110 (Dam−, Dcm−, HsdRMS+) or ER2796 (Dam−, Dcm−, HsdRMS−), thus preventing recognition and degradation via these systems. However, such methyl-free *E. coli* strains are unable to produce MCs since construction of the *E. coli* MC-producing strain (Kay M A, et al. (2010) *Nat Biotechnol* 28(12):1287-1289) required complex engineering to stably expresses a set of inducible minicircle-assembly enzymes (the ϕC31-integrase and the I-SceI homing-endonuclease for induction of MC formation and degradation of the PP replicon, respectively).

Accordingly, when the MC technology was repurposed for bacterial applications, it was also necessary to engineer *E. coli* MC-producer strains that generate various forms of methylation-free MCs (FIG. 6A-C, 7, 8A-8F). Although a completely methylation-free MC producer could be required when working against Type IV systems targeting both adenine- and cytosine-methylated DNA, bacterial RM systems exist with targets that specifically match the *E. coli* Dam methyltransferase motif (GATC), such as the Dpn system of *Streptococcus pneumoniae* (Lacks S A, et al. (1984) *J Bacteriol* 157(3):934-936) or the Pin25611FII system of *Prevotella intermedia* (Johnston C D, et al., (2017) *PLoS One* 12(9):e0185234). These systems digest unmethylated Dam sites on genetic tools propagated within a completely methyl-free strain, hence Dam methylation is protective in these cases. Therefore, a suite of *E. coli* strains capable of producing distinct types of methyl-free MC DNA were created to account for the inherent variation of RM systems in bacteria and maximize the applicability of the SyMPL approach. CRISPR-Cas9 genome editing was applied iteratively to sequentially delete methyltransferase genes from the original *E. coli* MC-producer strain (Dam+, Dcm+, HsdM+) (FIG. 7). These new strains produce methylcytosine-free MC DNA (*E. coli* JMC1; Dam+, Dcm−, HsdM+), methylcytosine- and methyladenine-free MC DNA except for Dam methylation (*E. coli* JMC2; Dam+, Dcm−, HsdM⁻−), and completely methyl-free MC DNA (*E. coli* JMC3; Dam−, Dcm−, HsdM−). Depending upon the Type IV RM systems identified within a desired bacterial host, one of these strains can be selected and utilized for production of SyMPL tools.

Example 3

Application of SyngenicDNA and SyMPL Approaches to a Bacterial Pathogen

RM systems are a known critical barrier to genetic engineering in most strains of *Staphylococcus aureus*, a pathogen with significant relevance to public health, which accounts for over 10,000 deaths per year in the U.S. (Lee B Y, et al. (2013) *Clin Microbiol Infect* 19(6):528-536; Sadykov M (2016) *Methods in molecular biology* (Clifton, NJ) 1373:9). Numerous mimicry-by-methylation approaches that seek expand tractability to more clinically relevant strains have been attempted (Monk I R, et al. (2012) *Front Cell Infect Microbiol* 2:49, Jones M J, et al. (2015) *PLoS One*10(3):e0119487). Based on its public health importance, *S. aureus* JE2, a derivative of the epidemic USA300 community-associated methicillin-resistant *S. aureus* (MRSA) LAC strain (Fey P D, et al. (2013) *MBio* 4(1):e00537-00512) was selected to demonstrate the efficacy of the stealth-by-engineering approaches described herein. As the first step, the methylome of *S. aureus* JE2 was determined using SMRT sequencing and this strain's RM targets were identified. SMRTseq and REBASE analysis of JE2 confirmed the presence of two Type-I RM systems recognizing the bipartite target sequences AGGN$_5$GAT (SEQ ID NO:4) and CCAYN$_6$TGT (SEQ ID NO:2) (Table 1; the modified base within each motif is shown in bold and N=any base) and a Type-IV system, previously shown to target cytosine methylation within the sequence SCNGS (where S=C or G) (Sadykov M (2016) *Methods in molecular biology* (Clifton, NJ) 1373:9).

The SyngenicDNA approach was then applied to the *E. coli-S. aureus* shuttle vector pEPSA5 (FIGS. 2A-2B). The pEPSA5 plasmid (Forsyth R A, et al. (2002) *Mol Microbiol* 43(6):1387-1400) contains a 2.5 kb *E. coli* replicon (ampicillin-resistance gene with a low copy number pl5a origin for autonomous replication) and a 4.3 kb *S. aureus* replicon (chloramphenicol-resistance gene, pC194-derived origin, and a xylose repressor protein gene, xylR) (FIG. 9A). The *S. aureus* replicon is nonfunctional when pEPSA5 is maintained and propagated within *E. coli*, and vice versa. Therefore, *S. aureus* JE2 RM targets occurring within the coding region of the pEPSA5 *E. coli* replicon were modified with synonymous substitutions adhering to *E. coli* codon bias. pEPSA5SynJE2 (FIG. 2C), a variant of pEPSA5 that differed by only six nucleotides (99.91% identical at nucleotide level), was synthesized, assembled (FIG. 9B) and propagated, eliminating three RM target motifs present in the original sequence. A ~70,000-fold ($p=7.76 \times 10^{-306}$) increase in transformation efficiency (CFU/µg DNA) was demonstrated using the entirely RM-silent pEPSA5SynJE2Dcm− (propagated in Dcm− *E. coli*) compared to the original pEPSA5 plasmid (propagated in Dcm+ *E. coli*) (FIG. 2D).

Subsequently, it was investigated whether a further increase in transformation efficiency could be achieved using the SyMPL (minicircle) approach. The Dcm− strains *E. coli* ER2796 and *E. coli* JMC1 were used to carry out the minicircle (MC) experiments independently of the Type IV system in *S. aureus* JE2. A SyngenicDNA pEPSA5 minicircle was generated for JE2 (pEPSA5SynJE2MC); 38% smaller than pEPSA5 and free of the original *E. coli* replicon (FIGS. 3A and 10).

The majority of the *S. aureus* JE2 RM system targets present on pEPSA5 are in the *E. coli* replicon (Type I: n=2, and Type IV: n=8) with only a single Type I system target in the *S. aureus* replicon (FIG. 9A), thus the MC approach eliminates two of the three Type I targets. The focus here was on investigating 1) whether the SyMPL approach achieves equal or perhaps even greater efficiency than the SyngenicDNA approach, and 2) whether removal of all Type I targets is required to achieve appreciable gains in transformation efficiency (compared with a partially SyngenicDNA plasmid that has a single Type I target remaining). The original plasmid pEPSA5 (Dcm+) was included in experiments as a control for accurate final comparison of efficiencies and was not considered a primary comparison. The pEPSA5SynJE2MC variant achieved ~$2 \times 10^7$ transformants/µg DNA, a further 3.5-fold increase ($p=1.78 \times 10^{-9}$) in transformation efficiency over pEPSA5SynJE2 and a >100,000-fold increase ($p=1.97 \times 10^{-284}$) compared to the original unmodified pEPSA5 plasmid (propagated in Dcm+ *E. coli*) (FIG. 3B, Tables 2-3).

In SyMPL experiments, by reducing the overall size of MC plasmids, the number of *S. aureus* replicons present within the µg of DNA used for transformations was also increased as compared with the µg used for full-length plasmids. Increasing the yield of functional replicons/µg of DNA might be an additional advantage of the MC approach. Thus, to more accurately compare transformation efficiencies between MCs and full-length plasmids, a secondary analysis was performed in which the transformation efficiencies from CFU/µg DNA to CFU/pmol DNA was adjusted (FIG. 3C, Table 4).

On a CFU/pmol DNA basis, the MC variant pEPSA5MCDcm− achieved a 436-fold increase in transformation efficiency over the original plasmid pEPSA5Dcm− ($p=<1.0 \times 10^{-306}$). This increase could be due to the elimination of the two Type I target motifs along with the *E. coli* replicon in the MC variant (FIG. 10A, B), or the smaller MCs passing more readily through the reversible pores formed in the *S. aureus* cell envelope during electroporation, or a combination of both. The relatively small 2.3-fold ($p=1.29 \times 10^4$) increase in transformation efficiency achieved by MC variant pEPSA5SynJE2MC over the plasmid pEPSA5SynJE2, both of which are completely RM-silent in JE2, favors the first possibility. In contrast, pEPSA5MC and pEPSA5SynJE2MC differed only by the presence or absence of a single Type I target, respectively (FIG. 3A). Eliminating this single target sequence resulted in a modest 1.5-fold ($p=1.01^{-14}$) increase in transformation efficiency.

Example 4

The Relative Contribution of Different RM Systems in a Single Strain

By definition, an entirely SyngenicDNA plasmid is silent with respect to all (Type I, II, III, and IV) RM systems within a host strain and is designed to maximize transformation efficiency. In addition, generation of complementary sets of partially SyngenicDNA plasmids can be used to determine the relative contribution of different RM systems within a host strain. For example, *S. aureus* JE2 contains two active Type I RM systems, which target unmethylated bipartite sequence motifs, in addition to a Type IV restriction system, SauUSI (Xu S Y, et al., (2011) *Nucleic Acids* Res39(13): 5597-5610), that targets methylated $S^{5m}CNGS$ motifs (either $m^5C$ or $^{5hm}C$) where S is C or G (FIG. 2A). Plasmid tools propagated in *E. coli* strains containing the Dcm orphan methyltransferase are methylated at $C^{5m}CWGG$ motifs, which overlap with the SauUSI target motif (SCNGS) resulting in vulnerability to degradation by this restriction system upon transformation to *S. aureus*. Therefore, in addition to the fully SyngenicDNA plasmid (pEPSA5SynJE2Dcm⁻) partially SyngenicDNA plasmids were generated, one that is RM-silent to Type I systems but not to Type IV systems (pEPSA5SynJE2Dcm⁺) and another that is vice versa (pEPSA5Dcm⁻) to determine the relative contribution of Type I or Type IV systems to the genetic barrier in *S. aureus* JE2. This type of experimental approach can be viewed as a 2×2 factorial design, crossing silencing of the Type I systems and silencing of the Type IV system.

The original pEPSA5 plasmid propagated in *E. coli* NEBalpha, a standard Dcm⁺ laboratory strain, achieved consistently poor transformation efficiencies (~10 CFU/µg DNA). This plasmid contains 11 individual RM target motifs (Type I; n=3, and Type IV; n=8) (FIG. 9A). Both system types are known to be actively involved in defense from foreign DNA in *S. aureus* (Monk I R, et al. (2012) *Front Cell Infect Microbiol* 2:49; Jones M J, et al. (2015) *PLoS* One10 (3):e0119487; Monk I R, et al. (2015) *MBio* 6(3):e00308-00315; Monk I R, et al., (2012) *MBio* 3(2)). Elimination of only Type I target motifs from the plasmid (pEPSA5SynJE2Dcm⁺) achieved a 13-fold increase ($p=2.75 \times 10^{-13}$) in transformation efficiency. In contrast, elimination of only Type IV system targets, by passaging pEPSA5 through the Dcm-deficient strain *E. coli* ER2796 (pEPSA5Dcm⁻), achieved a >139-fold increase ($p=2.48 \times 10^{-69}$) in efficiency. However, when both Type I and Type IV targets were eliminated (pEPSA5SynJE2Dcm⁻), a supramultiplicative (rather than an additive) effect on transformation efficiency was observed, with in an increase of ~70,000-fold (p=7.76×10$^{-306}$) compared with the original pEPSA5Dcm$^+$ plasmid (p for interaction=6.98×10$^{-27}$).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Patent Application No. 62/802,016, filed Feb. 6, 2019, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

TABLE 1

Methylated motifs identified in *Staphylococcus aureus* JE2 by SMRTseq

| No | R-M System Type | Motif[a] | Modified Position | Modification Type | # of Motifs in Genome[b] | # of Motifs Detected | % Motifs Detected | Partner Motif |
|---|---|---|---|---|---|---|---|---|
| A | I | ACANNNNNNRTGG (SEQ ID NO: 6) | 3 | $^{m6}$A | 502 | 497 | 99.00% | CCAYNNNNNNTGT (SEQ ID NO: 2) |
| B1 | I | CCAYNNNNNNTGT (SEQ ID NO: 2) | 3 | $^{m6}$A | 502 | 496 | 98.80% | ACANNNNNNRTGG (SEQ ID NO: 6) |
| B2 | I | ATCNNNNNCCT (SEQ ID NO: 7) | 1 | $^{m6}$A | 702 | 693 | 98.72% | AGGNNNNNGAT (SEQ ID NO: 4) |
| C1 | I | AGGNNNNNGAT (SEQ ID NO: 4) | 1 | $^{m6}$A | 702 | 693 | 98.72% | ATCNNNNNCCT (SEQ ID NO: 7) |

[a]The modified base within each motif is bolded while the modified base in the complementary strand is itattcized.
[b]The total number includes motifs occurring on the "+" and "−" strands.

TABLE 2

*Staphylococcus aureus* JE2 colony counts for pEPSA5-based SyngenicDNA and SyMPL approaches Experiment 1: SyngenicDNA method

| Competent Cell Preparation | Experiment | | CFU/µg plasmid DNA | | | |
|---|---|---|---|---|---|---|
| | | | pEPSA5 (Dcm+) | pEPSA5 (Dcm−) | pEPSA5 SynJE2 (Dcm+) | pEPSA5 SynJE2 (Dcm−) |
| OD$_{600\,mm}$ 0.86 | Biological Replicate 1 | Independent Replicate A | 0 | 385 | 10 | 159487.5 |
| | | Independent Replicate B | 10 | 532.5 | 32.5 | 264400 |
| | | Independent Replicate C | 0 | 505 | 42.5 | 219400 |
| OD$_{600\,mm}$ 0.80 | Biological Replicate 2 | Independent Replicate A | 15 | 757.5 | 30 | 210160 |
| | | Independent Replicate B | 2.5 | 655 | 47.5 | 212275 |
| | | Independent Replicate C | 2.5 | 795 | 42.5 | 228025 |
| OD$_{600\,mm}$ 0.93 | Biological Replicate 3 | Independent Replicate A | 10 | 2175 | 247.5 | 1077070 |
| | | Independent Replicate B | 10 | 2105 | 265 | 1268995 |
| | | Independent Replicate C | 12.5 | 775 | 105 | 663390 |

Experiment 2: SyngenicDNA Minicircle Plasmid (SyMPL) method

| Competent Cell Preparation | Experiment | | CFU/µg plasmid DNA | | | | |
|---|---|---|---|---|---|---|---|
| | | | pEPSA5 (Dcm+) | pEPSA5 (Dcm−) | pEPSA5MC (Dcm−) | pEPSA5SynJE2 (Dcm−) | pEPSA5SynJE2MC (Dcm−) |
| OD$_{600\,mm}$ 1.67 | Biological Replicate 1 | Independent Replicate A | 0 | 13000 | 19780000 | 3430000 | 26190000 |
| | | Independent Replicate B | 0 | 9000 | 11050000 | 4230000 | 12470000 |
| | | Independent Replicate C | 0 | 3750 | 1630000 | 1180000 | 1840000 |
| OD$_{600\,mm}$ 1.56 | Biological Replicate 2 | Independent Replicate A | 185 | 35550 | 22150000 | 12930000 | 38980000 |
| | | Independent Replicate B | 135 | 11950 | 7960000 | 4460000 | 10360000 |
| | | Independent Replicate C | 185 | 17850 | 9920000 | 8780000 | 17220000 |
| OD$_{600\,mm}$ 1.52 | Biological Replicate 3 | Independent Replicate A | 535 | 32600 | 11840000 | 8140000 | 20020000 |
| | | Independent Replicate B | 385 | 12950 | 14260000 | 5760000 | 20100000 |
| | | Independent Replicate C | 295 | 35250 | 20380000 | 1380000 | 31260000 |

TABLE 3

Fold changes in transformation efficiencies (CFU/μg) between pEPSA5 plasmid variants

| Plasmids compared | Fold difference | 95% LB[a] | 95% UB[b] | p-value |
|---|---|---|---|---|
| Experiment 1: SyngenicDNA method | | | | |
| pEPSA5 (Dcm+) versus pEPSA5SynJE2 (Dcm+) | 13.2 | 6.6 | 26.3 | $2.8 \times 10^{-13}$ |
| pEPSA5 (Dcm−) versus pEPSA5SynJE2 (Dcm−) | 493.8 | 399.3 | 610.5 | $<3.2 \times 10^{-308}$ * |
| pEPSA5 (Dcm+) versus pEPSA5 (Dcm−) | 139.4 | 80.5 | 241.7 | $2.5 \times 10^{-69}$ |
| pEPSA5SynJE2 (Dcm+) versus pEPSA5SynJE2 (Dcm−) | 5231.9 | 4494.7 | 6089.9 | $<3.2 \times 10^{-308}$ * |
| pEPSA 5 (Dcm+) versus pEPSA5SynJE2 (Dcm−) | 68851.2 | 38393.2 | 123472.5 | $7.8 \times 10^{-306}$ |
| Experiment 2: SyngenicDNA Minicircle Plasmid (SyMPL) method | | | | |
| pEPSA5 (Dcm−) versus pEPSA5SynJE2 (Dcm−) | 292.6 | 190.3 | 449.8 | $1.4 \times 10^{-147}$ |
| pEPSA5MC (Dcm−) versus pEPSA5SynJE2MC (Dcm−) | 1.5 | 1.4 | 1.7 | $1.0 \times 10^{-14}$ |
| pEPSA5 (Dcm−) versus pEPSA5MC (Dcm−) | 692.1 | 508.4 | 942.2 | $<3.2 \times 10^{-308}$ * |
| pEPSA5SynJE2 (Dcm−) versus pEPSA5SynJE2MC (Dcm−) | 3.5 | 2.3 | 5.4 | $1.8 \times 10^{-9}$ |
| pEPSA 5 (Dcm−) versus pEPSA5SynJE2MC (Dcm−) | 1038.0 | 810.9 | 1328.7 | $<3.2 \times 10^{-308}$ * |

[a] and [b] LB and UB are lower bound and upper bound of the 95% confidence interval
* p-value represented as an inequality as Stata software does not calculate p-values lower than this value

TABLE 4

*Staphylococcus aureus* JE2 colony counts and fold changes in transformation efficiencies in CFU/pmol Experiment 2: SyngenicDNA Minicircle Plasmid (SyMPL) method colony counts (CFU/pmol DNA)

| Competent Cell Preparation | Experiment | pEPSA5 (Dcm+) | pEPSA5 (Dcm−) | pEPSA5MC (Dcm−) | pEPSA5SynJE2 (Dcm−) | pEPSA5SynJE2MC (Dcm−) |
|---|---|---|---|---|---|---|
| $OD_{600\ nm}$ 1.67 Biological Replicate 1 | Independent Replicate A | 0.0 | 57793.2 | 55482314.7 | 15248510.7 | 73462175.0 |
| | Independent Replicate B | 0.0 | 40010.7 | 30994923.0 | 18805014.7 | 34977981.0 |
| | Independent Replicate C | 0.0 | 16671.1 | 4572101.8 | 5245843.3 | 5161145.5 |
| $OD_{600\ nm}$ 1.56 Biological Replicate 2 | Independent Replicate A | 822.4 | 158042.1 | 62130094.5 | 57481995.2 | 109337746.5 |
| | Independent Replicate B | 600.2 | 53125.3 | 22327564.4 | 19827509.6 | 29059493.4 |
| | Independent Replicate C | 822.4 | 79354.5 | 27825306.4 | 39032630.9 | 48301590.4 |
| $OD_{600\ nm}$ 1.52 Biological Replicate 3 | Independent Replicate A | 2378.4 | 144927.5 | 33210849.6 | 36187427.8 | 56155507.6 |
| | Independent Replicate B | 1711.6 | 57570.9 | 39998878.0 | 25606828.5 | 56379905.2 |
| | Independent Replicate C | 1311.5 | 156708.5 | 57165296.9 | 6134969.3 | 87683374.9 |

Experiment 2: SyngenicDNA Minicircle Plasmid (SyMPL) method fold changes in transformation efficiencies (CFU/pmol DNA)

| Plasmids compared | Fold difference | 95% LB[a] | 95% UB[b] | p-value |
|---|---|---|---|---|
| pEPSA5 (Dcm−) versus pEPSA5SynJE2 (Dcm−) | 292.6 | 190.3 | 449.8 | $1.4 \times 10^{-147}$ |
| pEPSA5MC (Dcm−) versus pEPSA5SynJE2MC (Dcm−) | 1.5 | 1.4 | 1.7 | $1.0 \times 10^{-14}$ |
| pEPSA5 (Dcm−) versus pEPSA5MC (Dcm−) | 436.7 | 320.8 | 594.5 | $<3.2 \times 10^{-308}$ * |
| pEPSA5SynJE2 (Dcm−) versus pEPSA5SynJE2MC (Dcm−) | 2.2 | 1.5 | 3.4 | $1.3 \times 10^{-4}$ |
| pEPSA 5 (Dcm−) versus pEPSA5SynJE2MC (Dcm−) | 655.0 | 511.7 | 838.4 | $<3.2 \times 10^{-308}$ * |

[a] and [b] LB and UB are lower bound and upper bound of the 95% confidence interval
* p-value represented as an inequality as Stata software does not calculate p-values lower than this value

TABLE 5

Oligonucleotides used in this study

| Primer name | Direction | SEQ ID NO: | Primer sequence (5'-3') | Characteristics |
|---|---|---|---|---|
| Bisulfite sequencing | | | | |
| E. coli_CCWGG_Region_1 | Forward | 8 | GGTTAGTTAGGTGAAATTTGTGTATAT | — |
| | Reverse | 9 | AATAACAACAAAAAACCACAACC | — |
| E. coli_CCWGG_Region_2 | Forward | 10 | ATGGA1TTGGT1111GG1TAGA1T | — |
| | Reverse | 11 | CAACCCTTTCAACACTTTATTCAAT | — |

TABLE 5-continued

Oligonucleotides used in this study

| Primer name | Direction | SEQ ID NO: | Primer sequence (5'-3') | Characteristics |
|---|---|---|---|---|
| E. coli_CCWGG_Region_3 | Forward | 12 | TGGGTTAATAGGAGGAATTAATTATG | — |
| | Reverse | 13 | CATAAACCAATATACCAAAAACATC | — |
| Construction pCasTet-λ plasmid from pCas and pCKTRBS | | | | |
| pCAS_Δara | Forward | 14 | TAAATAATGGATATTAATACTGAAACTGAGATCAAG | Overlap |
| | Reverse | 15 | GTCTTAACGCTCATGTCTAGATTAAGAAATAATCTTC | Overlap |
| TetR/PtetO | Forward | 16 | TAATCTAGACATGAGCGTTAAGACCCACTTTCACATTTAAG | Overlap |
| | Reverse | 17 | TTTCAGTATTAATATCCATTATTTACCTCCTTAGGTCAC | Overlap |
| pCAS_InsertCheck | Forward | 18 | CAATTGATCGTAAACGATATACGTCTA | Overlap |
| | Reverse | 19 | CTCAAGACGATCCTGAATGTAATAA | Overlap |
| Assembly of DNA editing templates for E. coli MTase gene recombineering | | | | |
| dcm_Upstream | Forward | 20 | TCGGTAAGCGCTTCATCCGTCAGC | Overlap |
| | Reverse | 21 | GAAATCTATGCATGGCCGACGTTCACGATA | Overlap |
| dcm_Downstream | Forward | 22 | GTCGGCCATGCATAGATTTCACCGGCCATC | Overlap |
| | Reverse | 23 | TGTCCAGGATGCGGATCGGCTG | Overlap |
| pRRS_dcmET | Forward | 24 | GAAGATCTAGATCTAGATAGTAAAAC | Overlap |
| | Reverse | 25 | GGCGTAATCATGGTCATAGC | Overlap |
| dcm_editing template | Forward | 26 | TCGGTAAGCGCTTCATCCGTCAGC | — |
| | Reverse | 27 | GAAATCTATGCATGGCCGACGTTCACGATA | — |
| hsd_Upstream | Forward | 28 | TTACGCCTGGTTGGGCGGTGAGGACAATACAGCC | Overlap |
| | Reverse | 29 | CTCGTTCACCCACGCCAATCATAACCCACATAAATATATT | Overlap |
| hsd_Downstream | Forward | 30 | TATGATTGGCGTGGGTGAACGAGCGCAGCCAACGCAG | Overlap |
| | Reverse | 31 | TACTATCTAGGATCTCACCCGTAAAGGGCTGGTC | Overlap |
| pRRS_hsdUpDown | Forward | 32 | GGGTGAGATCCTAGATAGTAAAACGGACATCACTCC | Overlap |
| | Reverse | 33 | CCCAACCAGGCGTAATCATGGTCATAGCTGTTTCC | Overlap |
| hsd_editing template | Forward | 34 | TGGTTGGGCGGTGAGGACAATAC | — |
| | Reverse | 35 | GATCTCACCCGTAAAGGGCTGGTC | — |
| dam_Upstream | Forward | 36 | TGATTACGCCTTTCGCCAATGTTGTTCACCTTCAC | Overlap |
| | Reverse | 37 | AGTCAGCATGGTTTCACCCGCGAAAAATAATTCTCAAG | Overlap |
| dam_Downstream | Forward | 38 | GGGTGAAACCATGCTGACTAACTAATTACACCTTCTC | Overlap |
| | Reverse | 39 | CTAGATCTTCAAAAACCGCAAGCAACCGTGAAAACGG | Overlap |
| pRRS_damUpDown | Forward | 40 | TGCGGTTTTTGAAGATCTAGATCTAGATAGTAAAAC | Overlap |
| | Reverse | 41 | ATTGGCGAAAGGCGTAATCATGGTCATAGCTG | Overlap |
| dam_editing template | Forward | 42 | TTCTTTAATCAGTTGCAGCGTGC | Overlap |
| | Reverse | 43 | AAGACCGCAGGTAATGTTGGTTC | Overlap |
| Modification of pTarget for E. coli MC MTase gene recombineering | | | | |
| E. coli_DcmProtospacer_1 | Forward | 44 | CACTGGAGCCgttttagagctagaaatagcaagttaaaat | Half Protospacer |
| | Reverse | 45 | ATTCTCACCTactagtattatacctaggactgagctagct | Half Protospacer |
| E. coli_DcmProtospacer_2 | Forward | 46 | AGTGATGAGGgttnagagctagaaatagcaagttaaaat | Half Protospacer |
| | Reverse | 47 | CACGCCTTCTactagtattatacctaggactgagctagct | Half Protospacer |
| E. coli_HsdProtospacer_1 | Forward | 48 | CGCGAAGCTGgttttagagctagaaatagcaagttaaaat | Half Protospacer |
| | Reverse | 49 | ACCAGATCGTactagtattatacctaggactgagctagct | Half Protospacer |
| E. coli_HsdProtospacer_2 | Forward | 50 | ATTGCCGAGGgttttagagctagaaatagcaagttaaaat | Half Protospacer |
| | Reverse | 51 | TTCCCCGCACactagtattatacctaggactgagctagct | Half Protospacer |
| E. coli_DamProtospacer_1 | Forward | 52 | TTTTTTGAAGgttttagagctagaaatagcaagttaaaat | Half Protospacer |
| | Reverse | 53 | GCGCGATTTTactagtattatacctaggactgagctagct | Half Protospacer |
| E. coli_DamProtospacer_2 | Forward | 54 | TGATATTAAAgttttagagctagaaatagcaagttaaaat | Half Protospacer |
| | Reverse | 55 | TCAAGCAGGGactagtattatacctaggactgagctagct | Half Protospacer |
| pTarget_InsertCheck | Forward | 56 | TGCTCACATGTTCTTTCCTGCG | |
| | Reverse | 57 | TCATGACATTGCACTCCACCG | |

TABLE 5-continued

Oligonucleotides used in this study

| Primer name | Direction | SEQ ID NO: | Primer sequence (5'-3') | Characteristics |
|---|---|---|---|---|
| Construction of pEPSA5Syn from pEPSA5 and RM-silent fragment | | | | |
| pEPSA5SynFrag | Forward | 58 | AACCTGCCCCGTTAGTTGAAGAAGGTT | Overlap |
|  | Reverse | 59 | GTCGACCTGCAGCCAAGC | Overlap |
| pEPSA5Backbone | Forward | 60 | CGGGGCAGGTTAGTGACATTAGAAA | Overlap |
|  | Reverse | 61 | TGCAGGTCGACTCTAGAGGATC | Overlap |
| Construction of pEPSA5 parental plasmids from pEPSA5/Syn and pMC | | | | |
| pEPSA5/SynMCPP | Forward | 62 | CGCGACAAGCTTCTGTAGGTTTTTAGGCATAAAACTATA | Overlap |
|  | Reverse | 63 | TTGGGGTCGACTCTAGAGGATCCCCGGGTACCGAG | Overlap |
| pMC_pEPSA | Forward | 64 | CTAGAGTCGACCCCAACTGGGGTAACCTTTGAGTTCTCTC | Overlap |
|  | Reverse | 65 | ACAGAAGCTTGTCGCGCCCGGGGAGCCC | Overlap |

TABLE 6

Methyltransferase enzymes commercially available for application in mimicry-by-methylation approaches.

| Recognition motif (5'-3') | Methyl-Modification introduced (5'-3') | Commercial Suppliers | | | | | |
|---|---|---|---|---|---|---|---|
| | | Takara Bio | New England Biolabs | Sib Enzyme | Minotech Biotechnology | Nippon Gene | Thermo Fischer | Zymo Research |
| ATCGAT | ATCG$^{m6}$AT | M.ClaI | — | — | M.BseCI | — | — | — |
| AAGCTT | $^{m6}$AAGCTT | M.HindIII | — | — | — | — | — | — |
| GGATCC | GGAT$^{m4}$CC | M.BamHI | M.BamHI | — | — | — | — | — |
| GAATTC | GA$^{m6}$ATTC | M.EcoRI | M.EcoRI | — | — | M.EcoRI | — | — |
| GGATG | GG$^{m6}$ATG | — | — | M3.BstF5I | — | — | — | — |
| GCNGC | G$^{m5}$CNGC | — | — | M.Fsp4HI | — | — | — | — |
| AGCT | AG$^{m5}$CT | M.AluI | M.AluI | — | — | — | — | — |
| TCGA | TCG$^{m6}$A | — | M.TaqI | — | — | — | — | — |
| GATC | G$^{m6}$ATC | — | M.EcoKDam | — | — | — | — | — |
| GGCC | GG$^{m5}$CC | M.HaeIII | M.HaeIII | — | — | — | — | — |
| GCGC | G$^{m5}$CGC | — | M.HhaI | M.HspAI | — | — | — | — |
| CCGG | $^{m5}$CCGG | — | M.MspI | — | — | — | — | — |
| CCGG | C$^{m5}$CGG | M.HpaII | M.HpaII | — | — | — | — | — |
| GC | G$^{m5}$C | — | M.CviPI | — | — | — | — | — |
| CG | $^{m5}$CG | — | M.SssI | — | — | — | M.SssI | M.SssI |
| A | $^{m6}$A | — | M.EcoGII | — | — | — | — | — |

TABLE 7

| Plasmid Name |
|---|
| Nucleotide Sequence |
| pEPSA5SynJE2MCParental (SEQ ID NO: 97) |
| ACATTACCCTGTTATCCCTAGATACATTACCCTGTTATCCCAGATGACATACCCTGTTATCCCTAGATGACATTACCCTGTTATCCC |
| AGATGACATTACCCTGTTATCCCTAGATACATTACCCTGTTATCCCAGATGACATACCCTGTTATCCCTAGATGACATTACCCTGTT |

TABLE 7-continued

Plasmid Name
Nucleotide Sequence

ATCCCAGATGACATTACCCTGTTATCCCTAGATACATTACCCTGTTATCCCAGATGACATACCCTGTTATCCCTAGATGACATTACC
CTGTTATCCCAGATGACATTACCCTGTTATCCCTAGATACATTACCCTGTTATCCCAGATGACATACCCTGTTATCCCTAGATGACA
TTACCCTGTTATCCCAGATGACATTACCCTGTTATCCCTAGATACATTACCCTGTTATCCCAGATGACATACCCTGTTATCCCTAGA
TGACATTACCCTGTTATCCCAGATGACATTACCCTGTTATCCCTAGATACATTACCCTGTTATCCCAGATGACATACCCTGTTATCC
CTAGATGACATTACCCTGTTATCCCAGATGACATTACCCTGTTATCCCTAGATACATTACCCTGTTATCCCAGATGACATACCCTGT
TATCCCTAGATGACATTACCCTGTTATCCCAGATGACATTACCCTGTTATCCCTAGATACATTACCCTGTTATCCCAGATGACATAC
CCTGTTATCCCTAGATGACATTACCCTGTTATCCCAGATAAACTCAATGATGATGATGATGGTCGAGACTCAGCGGCCGCGGT
GCCAGGGCGTGCCCTTGGGCTCCCCGGGCGCGACaagcttctgtaggttttttaggcataaaactatatgatttacccctaaatctttt
aaaatgcccctttaaaattcaaaataaaggcatttaaaatttaaatatttcttgtgataaagtttgttaaaaaggagtggttttatga
ctgttatgtggttatcgattataggtatgtggttttgtattggaatggcattttttgctatcaaggttattaaaaataaaaattaga
ccacgcatttatgccgagaaaatttattgtgcgttgagaagaaccccttaactaaacttgcagacgaatgtcggcatagcgtgagcta
ttaagccgaccattcgacaagttttgggattgttaagggttccgaggctcaacgtcaataaagcaattggaataaagaagcgaaaaa
ggagaagtcggttcagaaaaagaagCatatgCatctggagctgtaatataaaaaccttcttcaactaacggggcaggttagtgacat
tagaaaaccgactgtaaaaagtacagtcggcattatctcatattataaaagccagtcagtcattaggcctatctgacaattcctgaataga
gttcataaacaatcctgcatgataaccatcacaaacagaatgatgtacctgtaaagatagcggtaaatatattgaattacctttatt
aatgaattttcctgctgtaataatgggtagaaggtaattactattattattgatatttaagttaaacccagtaaatgaagtccatgg
aataatagaaagagaaaaagcattttcaggtataggtgttttgggaaacaatttccccgaaccattatatttctctacatcagaaag
gtataaatcataaaactctttgaagtcttttacaggagtccaaataccagagaatgttttagatacaccatcaaaaattgtata
aagtggctctaacttatcccaataacctaactctccgtcgctattgtaaccagttctaaaagctgtatttgagtttatcacccttgt
cactaagaaaataaatgcagggtaaaatttatatccttcttgttttatgtttcggtataaaacactaatatcaatttctgtggttat
actaaaagtcgtttgttggttcaaataatgattaaatatctctttctcttccaattgtctaaatcaattttattaaagttcatttg
atatgcctcctaaatttttatctaaagtgaatttaggaggcttactttgtctgctttcttcattagaatcaatccaaaagtcaatatt
actgtaacataaatatatattttaaaaatatcccactttatccaattttcgtttgttgaactaatgggtgcttagttgaagaataa
aagaccacattaaaaaatgtggtcttttgtgtttttttaaaggatttgagcgtagcgaaaaatccttttcttcttatcttgataat
aagggtaactattgccggcgaggctagttaccccttaagttattggtatgactggttttaagcgcaaaaaaagttgcttttcgtacc
tattaatgtatcgttttaaatgaatagtaaaaaacatacatagaaagggggaaaaagcaactttttttttattgtcatagtttgtgaaaa
ctaagttgtttttatgtgttataacatggaaaagtatactgagaaaaaacaaagaaatcaagtatttcagaaatttattaaacgtca
tattggagagaatcaaatggatttagttgaagattgcaatacatttctgtcttttgtagctgataaaactttagaaaaacagaaatt
atataaagctaattcttgtaaaaatcgattttgtcctgtctgtgcttggagaaaagctagaaaagatgcattgggtttatctttgat
gatgcaatatattaagcagcaagagaaaaaggagtttatctttttaactttgactacacctaatgtaatgagtgatgaattagaaaa
tgaaataaaacgttataataattcttttagaaaacttataaagagaaaaaaagtaggtagtgttataaagggatatgttcgtaagtt
agagattacatataataaaaaaagagatgattataatcctcattttcatgtgttaattgcagtaaataaatcgtatttcacagataa
aagatattatattagccaacaagaatggttagatttatggcgtgatgtaacgggcatttcagaaataacacaagttcaagttcaaaa
aataagacaaataataataaagaattatatgaaatggctaagtattctggtaaagatagtgattatttaatataatcaaaaagtctt
tgatgcatttataaatcacttaaaggtaaacaggtattagtttattcaggattatttaaagaggctaaaaagaaattaaaaatgg
ggatttagattacttaaaagaaattgatccaaccgaatatatctatcaaatttttttatatttggaaacaaaaagagtatttagctag
tgaactttatgacttaacagaacaagaaaaagagaaattaatcacaaaatgatagacgaaatcgaggaagaacaataacaaaatat
aagtgctaacagtcgtctgcaagtttagttaagggttcttctcaacgcacaataaatttttctcggcataaatgcgtggtctaatttt
tattttaatacccttgatagcaaaaaatgccattccaatacaaaaccacatacctataatcgatacccatcaatcaatcttccttttcataaaac
cactcctttttaacaaactttatcacaagaaataggcattctacgactataacttaaatttatatttttttacttttataatatataat
tgattatagaataatgttgctcatatcgtttgccaacatctagtactcaaattacactatgttacacttggtaatattaaccgaact
tccccctgtccaaattagataagaggtaataataaatggaaaataattttatagtaaatgaaaatgagaagcgtgtattaaaacaaat
tttcaataacagcaatatttcacgaacacaaatatcgaagaatttagaactttaaaacttaataattctaacattctgaacaactt
aaaacacaagagtttagttaatgaagtaggagaaggtaatagtactaaaagtggtggacgaaagcctattttactcgaaattaacca
aaaaatatggctactatattctatggatttaacatatgattccgttgaattaatgtacaactactttgatgctactatattaaagca
agattcctacgaattaaatgataaaaatgtaagcagtatattacaaattttaaaatctaatataaacgtctcagaaaaatatgatac
gttatatggttacttggtatatctatatccatacacggtatcgttgacgatgagcaaaacatcaatcatcttcctttttcataaaaa
tgagaaacgcacatttaccgatgaatttaaagtcattcacaaatgttcctgtcgttatagaaaatgaagcaaatttatcagcgctata
tgaaaaagtttatatattaattcaaacataaaataatttgattacttttaagtattcacaagggtataggcgctggcatcctaataaa
taaaaaactttatcgtggctcaaatggagaggctggagagataggtaagacattggttttggaatctataaataacaatgacaacaa
atattataaaatcgaagatatatgctcccaagacgctttaatacagaaaataaataaataaggttgggcgtcacattgacgtttacaga
actaatccaatattacaacgaaggaaattcaattgttgctcatgaaatttaaacaatttattaataaaatgacagttctgattcataa
tttgaatacacaatttaacccagacgctatttatattaactgtccttttaattaatgaattaccaaatattttaaatgaaattaaaga
gcaattctcctgtttttctcaaggcagtccagttcaattacatttaactactaatgtaaaacaagctacttttattgggtggcacttt
agcaataatgcaaaaaacattaaatataaataacttcaaatgaatattaaataattacagcagtctgagttataaaatagatatct
cggaccgtcataaaaaatttatttgctttcaggaaaattttttctgtataatagattcaagttagtttgtttttattaaattaaccaact
aaaatgtagaattcgagctcggtacccggggatcctctagagtcgaCCCCAACTGGGGTAACCTTTGAGTTCTCTCAGTTGG
GGGTAATCAGCATCATGATGTGGTACCACATCATGATGCTGATTATAAGAATGCGGCCGCCACACTCTAGTGGATCTCGAGTTAAT
AATTCAGAAGAACTCGTCAAGAAGGCGATAGAAGGCGATGCGCTGCGAATCGGGAGCGGCGATACCGTAAAGCACGAGGAAGCG
GTCAGCCCATTCGCCGCCAAGCTCTTCAGCAATATCACGGGTAGCCAACGCTATGTCCTGATAGCGGTCCGCCACACCCAGCCGGC
CACAGTCGATGAATCCAGAAAAGCGGCCATTTTCCACCATGATATTCGGCAAGCAGGCATCGCCATGGGTCACGACGAGATCCTC
GCCGTCGGGCATGCTCGCCTTGAGCCTGGCGAACAGTTCGGCTGGCGCGAGCCCCTGATGCTCTTCGTCCAGATCATCCTGATCGA
CAAGACCGGCTTCCATCCGAGTACGTGCTCGCTCGATGCGATGTTTCGCTTGGTGGTCGAATGGGCAGGTAGCCGGATCAAGCGTA
TGCAGCCGCCGCATTGCATCAGCCATGATGGATACTTTCTCGGCAGGAGCAAGGTGAGATGACAGGAGATCGTCTGCCCCGGCACTT
CGCCCAATAGCAGCCAGTCCCTTCCCGCTTCAGTGACAACGTCGAGCACAGCTGCGCAAGGAACGCCCGTCGTGGCCAGCCACGA
TAGCCGCGCTGCCTCGTCTTGCAGTTCATTCAGGGCACCGGACAGGTCGGTCTTGACAAAAAGAACCGGGCGCCCCTGCGCTGAC
AGCCGGAACACGGCGGCATCAGAGCAGCCGATTGTCTGTTGTGCCCAGTCATAGCCGAATAGCCTCTCCACCCAAGCGGCCGGAG
AACCTGCGTGCAATCCATCTTGTTCAATCATGCGAAACGATCCTCATCCTGTCTCTTGATCAGAGCTTGATCCCCTGCGCCATCAGA
TCCTTGGCGGCGAGAAAGCCATCCAGTTTACTTTGCAGGGCTTCCCAACCTTACCAGAGGGCGCCCCAGCTGGCAATTCCGGTTCG
CTTGCTGTCCATAAAACCGCCCAGTCTAGCTATCGCCATGTAAGCCCACTGCAAGCTACCTGCTTTCTCTTTGCGCTTGCGTTTTCC
CTTGTCCAGATAGCCCAGTAGCTGACATTCATCCGGGGTCAGCACCGTTTCTGCGGACTGGCTTTCTACGTGCTCGAGgggGgcAAA
CGGTCCTCAGCTTGGCTGTTTTGGCGGATGAGAGAAGATTTTCAGCCTGATACAGATTAAATCAGAACGCAGAAGCGGTCTGATA
AAACAGAATTTGCCTGGCGGCAGTAGCGCGGTGGTCCCACCTGACCCCATGCCGAACTCAGAAGTGAAACGCCGTAGCGCCGATG
GTAGTGTGGGGTCTCCCCATGCGAGAGTAGGGAACTGCCAGGCATCAAATAAAACGAAAGGCTCAGTCGAAAGACTGGGCCTTTC
GTTTTATCTGTTGTTTGTCGGTGAACGCTCTCCTGAGTAGGACAAATCCGCCGGGAGCGGATTTGAACGTTGCGAAGCAACGGCCC
GGAGGGTGGCGGGCAGGACGCCCGCCATAAACTGCCAGGCATCAAATTAAGCAGAAGGCCATCCTGACGGATGGCCTTTTTGCGT
TTCTACAAACTCTTTTGTTTATTTTTCTAAATACATTCAAATATGTATCCGCTCATGACCAAAATCCCTTAACGTGAGTTTTCGTTCC ACTGAGCGTCAGACCCCGTAGAAAAGATCAAAGGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGCGGCAGGGTCGGAACAGGAGAGCGC
ACGAGGGAGCTTCCAGGGGGAAACGCCTGGTATCTTTATAGTCCTGTCGGGTTTCGCCACCTCTGACTTGAGCGTCGATTTTTGTG
ATGCTCGTCAGGGGGCGGAGCCTATGGAAAAACGCCAGCAACGCGGCCTTTTTACGGTTCCTGGCCTTTTGCTGGCCTTTTGCTC
ACATGTTCTTTCCTGCGTTATCCCCTGATTCTGTGGATAACCGTATTACCGCCTTTGAGTGAGCTGATACCGCTCGCCGCAGCCGAA
CGACCGAGCGCAGCGAGTCAGTGAGCGAGGAAGCGGAAGAGCGCCTGATGCGGTATTTTCTCCTTACGCATCTGTGCGGTATTTC
ACACCGCATATGGTGCACTCTCAGTACAATCTGCTCTGATGCCGCATAGTTAAGCCAGTATACACTCCGCTATCGCTACGTGACTG
GGTCATGGCTGCGCCCCGACACCCGCCAACACCCGCTGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCACCGAAACGCGCGAGGCAGCAGATCAATTCGCGCGC
GAAGGCGAAGCGGCATGCATAATGTGCCTGTCAAATGGACGAAGCAGGGATTCTGCAAACCCTATGCTACTCCGTCAAGCCGTCA
ATTGTCTGATTCGTTACCAATTATGACAACTTGACGGCTACATCATTCACTTTTTCTTCACAACCGGCACGGAACTCGCTCGGGCTG
GCCCCGGTGCATTTTTTAAATACCCGCGAGAATAGAGTTGATCGTCAAAACCAACATTGCGACCGACGGTGGCGATAGGCATCC
GGGTGGTGCTCAAAAGCAGCTTCGCCTGGCTGATACGTTGGTCCTCGCGCCAGCTTAAGACGCTAATCCCTAACTGCTGGCGGAAA
AGATGTGACAGACGCGACGGCGACAAGCAAACATGCTGTGCGACGCTGGCGAT pEPSA5SynJE2MC
                                                                        (SEQ ID NO: 98)
GGGCTCCCCGGGCGCGACaagcttctgtaggttttttaggcataaaactatatgatttacccctaaatcttttaaaatgcccc
ttaaaattcaaaataaaggcatttaaaatttaaatatttcttgtgataaagtttgttaaaaaggagtggttttatgactgttatgtg
gttatcgattataggtatgtggttttgtattggaatggcattttttgctatcaaggttattaaaaataaaaattagaccacgcattt
atgccgagaaaatttattgtgcgttgagaagaaccttaactaaacttgcagacgaatgtcggcatagcgtgagctattaagccgac
cattcgacaagttttgggattgttaagggttccgaggctcaacgtcaatgcaattggaataaagaagcgaaaaaggagaagtcg
gttcagaaaaagaagCatatgCatctggagctgtaatataaaaaccttcttcaactaacgggggcaggttagtgacattagaaaaccg
actgtaaaaagtacagtcggcattatctcatattataaaagccagtcattaggcctatctgacaattcctgaatagagttcataaac
aatcctgcatgataaccatcacaaacagaatgatgtacctgtaaagatagcggtaaatatattgaattacctttattaatgaatttt
cctgctgtaataatgggtagaaggtaattactattattattgatatttaagttaaacccagtaaatgaagtccatggaataataaa
agagaaaaagcattttcaggtataggtgttttcagggaaacaattttccccgaaccattatattttctctacatcagaaaggtataaatca
taaaactctttgaagtcattcttttacaggagtccaaataccagagaatgttttagatacaccatcaaaaattgtataaagtggctct
aacttatcccaataacctaactctccgtcgctattgtaaccagttctaaaagctgtatttgagtttatcaccttgtcactaagaaa
ataaatgcagggtaaaatttatatcctcttgttttatgtttcggtataaaacactaatatcaattctgtggttatactaaaagtc
gtttgttggttcaaataatgattaaatatctctttctcttccaattgtcaattcaattttattaaagttcatttgatatgcctcc
taaattttttatctaaagtgaatttaggaggcttacttgtctgattcttcattagaatcaatccttttttaaaagtcaatattactgt
aacataaatatatatttttaaaaatatcccactttatccaattttcgtttgttgaactaatgggtgattagttgaagaataaaagacc
acattaaaaaatgtggtctttttgtgttttttaaaggattgagcgtagcgaaaatccttttctttcttatcttgataataagggt
aactattgccggcgaggctgattacccttaagttattggtagctggttttaagcgcaaaaaaagttgcttttcgtacctattaa
tgtatcgttttaaatgaatagtaaaaaacatacatagaaaggggaaaaagcaactttttttattgtcatagtttgtgaaaactaagt
tgttttatgtgttataacatggaaaagtatactgagaaaaaacaaagaaatcaagtatttcagaaatttattaaacgtcatattgg
agagaatcaaatggatttagttgaagattgcaatacatttctgtcttttgtagctgataaaactttagaaaaacagaaattatataa
agctaattcttgtaaaaatcgattttgtcctgtctgtgctttggagaaaacgtagaaaaagtgcattgggttttactttttgatgatgca
atatattaagcagcaagagaaaaaggagtttatctttttaactttgactacacctaatgtaatgagtgatgaattagaaaatgaaat
aaaacgttataataattcttttagaaaacttataaagagaaaaaaagtaggtagtgttataaagggatatgttcgtaagttagagat
tacatataataaaaaaagagatgattataatcctcattttcatgtgttaattgcagtaaataaatcgtatttcacagataaaagata
ttatattagccaacaagaaagttagatttatggcgtgatgtaacgggcatttcagaaataacacaagttcaagttcaaaaaataag
acaaaataataaaagaattatatgaaatggctaagtattctggtaaagatagtgattatttaataaatcaaaaagtcttttgatgc
attttataaatcacttaaaggtaaacaggtattagtttattcaggatttatttaaagaggctaaaaagaaattaaaaaatggggatt
agattacttaaaagaaattgatccaaccgaatatatctatcaaatttttatatttggaaacaaaaagagtatttagctagtgaact
ttatgactaacagaacaagaaaaagaaattaatcacaaaatgataagcaaagtgaggaagaacaatacaaatataagtgc
taacagtcgtctgcaagtttagttaagggtcttctcaacgcacaataaattttctcggcataaatgcgtggtctaattttttatttt
taataaccttgatagcaaaaaatgccattccaatacaaaaccacatacctataatcgataaccacataacagtcataaaccactcc
tttttaacaaacttttatcacaagaaatattttggcatttctacgactataacttaaatttatattttttactttataatatataattg
attatagaataatgttgctcatatcgtttgccaacatctagtactcaaattacactatgttacacttggtaatattaaccgaacttc
ccctgtccaaattagataagaggtaataaataatggaaaataattttatagtaaatgaaaatgagaagcgtgtattaaaacaaattt
tcaataacagcaatatttcacgaacacaaatatcgaagaatttagaacttaataaaagctactattctaacattctgaacaacttaa
aacacaagagtttagttaatgaagtaggagaaggtaatagtactaaaagtggtggacgaaagcctattttactcgaaattaaccaaa
aatatggctactatatttctatggatttaacatatgattccgttgaattaatgtacaactactttgatgctactatattaaagcaag
attcctacgaattaaatgataaaaatgtaagcagtatattacaaattttaaaattttaataaaacgtctcagaaaaatatgatacgt
tatatgggttacttggtatatctatatccatacacgatatcgttgacgatgagcaaaacataatcaatcttcttttcataaaaatg
agaaacgcacatttaccgatgaatttaaagtcattcacaaatgttcctgtcgttatagaaaatgaagcaaatttatcagcgctatatg
aaaaagtttatatattaattcaaacataaataatttgattacttttaagtattcacaagggtataggcgctggcatcctaataaata
aaaaacttttatcgtggctcaaatggagaggctggagagatagggtaagacattggttttggaatctataaataacaatgacaaacaat
attataaaatcgaagatatatgctcccaagacgctttaatacagaaataaataatggtgggcgtcacattgacgtttacagaac
taatccaatattacaacgaaggaaattcaattgttgctcatgaaatttaaacaattatttaataaaatgacagttctgattcataatt
tgaatacacaatttaacccagacgctatttatattaactgtcctttaattaatgaattaccaaatatttaaaatgaaattaaagagc
aattctcctgtttttctcaaggcagtccagttcaattacattttaactactaatgtaaaacaagctacttattagggtggcactttag
caataatgcaaaaaacattaaatataaataacattcaaatgaattattaaataattacagcagtctgagttataaaatagatatctcg
gaccgtcataaaaaatttatttgattcaggaaaattttttctgtataatagattcaagttagtttgttattaaaattaaccaactaaa
atgtagaattcgagctcggtacccggggatcctctagagtcgaCCCAACTGGGGTAACCTT pEPSA5MCParental
                                                                        (SEQ ID NO: 99)
ACATTACCCTGTTATCCCTAGATACATTACCCTGTTATCCCAGATGACATACCCTGTTATCCCTAGATGACATTACCCTG
TTATCCCAGATGACATTACCCTGTTATCCCTAGATACATTACCCTGTTATCCCAGATGACATACCCTGTTATCCCTAGAT
GACATTACCCTGTTATCCCAGATGACATTACCCTGTTATCCCTAGATACATTACCCTGTTATCCCAGATGACATACCCTG TABLE 7-continued Plasmid Name
Nucleotide Sequence TTATCCCTAGATGACATTACCCTGTTATCCCAGATGACATTACCCTGTTATCCCTAGATACATTACCCTGTTATCCCAGA
TGACATACCCTGTTATCCCTAGATGACATTACCCTGTTATCCCAGATGACATTACCCTGTTATCCCTAGATACATTACCC
TGTTATCCCAGATGACATACCCTGTTATCCCTAGATGACATTACCCTGTTATCCCAGATGACATTACCCTGTTATCCCTA
GATACATTACCCTGTTATCCCAGATGACATACCCTGTTATCCCTAGATGACATTACCCTGTTATCCCAGATGACATTACC
CTGTTATCCCTAGATACATTACCCTGTTATCCCAGATGACATACCCTGTTATCCCTAGATGACATTACCCTGTTATCCCA
GATGACATTACCCTGTTATCCCTAGATACATTACCCTGTTATCCCAGATGACATACCCTGTTATCCCTAGATGACATTAC
CCTGTTATCCCAGATAAACTCAATGATGATGATGATGGTCGAGACTCAGCGGCCGCGGTGCCAGGGCGTGCCCTT
GGGCTCCCCGGGCGCGACaagcttctgtaggttttaggcataaaactatatgatttacccctaaatctttaaaatgccc
cttaaaattcaaataaaggcatttaaatttaaatatttcttgtgataaagtttgttaaaaaggagtggttttatgact
gttatgtggttatcgattataggtatgtggttttgtattggaatggcattttttgctatcaaggttattaaaaataaaaa
ttagaccacgcatttatgccgagaaaatttattgtgcgttgagaagaaccctaactaaacttgcagacgaatgtcggca
tagcgtgagctattaagccgaccattcgacaagttttgggattgttaagggttccgaggctcaacgtcaataaagcaatt
ggaataaagaagcgaaaaggagaagtcggttcagaaaagaaggatatggactggagctgtaatataaaaaccttctt
caactaacggggcaggttagtgacattagaaaaccgactgtaaaaagtacagtcggcattatctcatattataaaagcca
gtcattaggcctatctgacaattcctgaatagagttcataaacaatcctgcatgataaccatcacaaacagaatgatgta
cctgtaaagatagcggtaaatatattgaattacctttattaatgaattttcctgctgtaataatgggtagaaggtaatta
ctattattattgatatttaagttaaacccagtaaatgaagtccatggaataatagaaagagaaaaagcattttcaggtat
aggtgttttgggaaacaattteceegaaccattatatttetctacateagaaaggtataateataaaactettgaagt
cattctttacaggagtccaaataccagagaatgttttagatacaccatcaaaaattgtataaagtggctctaacttatcc
caataacctaactctccgtcgctattgtaaccagttctaaaagctgtatttgagtttatcacccttgtcactaagaaaat
aaatgcagggtaaaatttatatccttcttgttttatgtttcggtataaaacactaatatcaatttctgtggttatactaa
aagtcgtttgttggttcaaataatgattaaatatctcttttctcttccaattgtctaaatcaattttattaaagttcatt
tgatatgcctcctaaattttttatctaaagtgaatttaggaggcttacttgtctgattcttcattagaatcaatccttttt
taaaagtcaatattactgtaacataaatatatatttaaaaatatcccacttatccaatttcgtttgttgaactaatg
ggtgattagttgaagaataaaagaccacattaaaaaatgtggtatttgtgttttttaaaggatttgagcgtagcgaaaa
atccttttctttcttatcttgataataagggtaactattgccggcgaggctagttaccettaagttattggtatgactgg
ttttaagcgcaaaaaaagttgcttMcgtacctattaatgtatcgttttaaatgaatagtaaaaaacatacatagaaaggg
gaaaaagcaactttttttattgtcatagtttgtgaaaactaagttgttttttatgtgttataacatggaaaagtatactga
gaaaaaacaaagaaatcaagtatttcagaaatttattaaacgtcatattggagagaatcaaatggatttagttgaagatt
gcaatacatttctgtcttttgtagctgataaaactttagaaaaacagaaattatataaagctaattcttgtaaaaatcga
ttttgtcctgtctgtgcttggagaaaagctagaaaagatgcattgggtttatctttgatgatgcaatatattaagcagca
agagaaaaaggagtttatcttttaactttgactacacctaatgtaatgagtgatgaattagaaaatgaaataaaacgtt
ataataattatttagaaaacttataaagagaaaaaaagtaggtagtgttataaagggatatgttcgtaagttagagatta
catataataaaaaagagatgattataatcctcatttcatgtgttaattgcagtaaataaatcgtatttcacagataaa
agatattatattagccaacaagaatggttagatttatggcgtgatgtaacgggcatttcagaaataacacaagttcaagt
tcaaaaaataagacaaaataataataaagaattatatgaaatggctaagtattctggtaaagatagtgattatttaataa
atcaaaaagtctttgatgcattttataaatcacttaaaggtaaacaggtattagtttattcaggattatttaaagaggct
aaaaagaaattaaaaaatgggatttagattacttaaaagaaattgatccaaccgaatatatctatcaaatttttttatat
ttggaaacaaaaagagtatttagctagtgaacttatgacttaacagaacagaaaaaagagaaattaatcacaaaatga
tagacgaaatcgaggaagaacaataacaaaatataagtgctaacagtcgtctgcaagtttagttaagggttcttctcaac
gcacaataaattttctcggcataaatgcgtggtctaattttttatttttaataaccttgatagcaaaaatgccattccaa
tacaaaaccacatacctataatcgataaccacataacagtcataaaaccactccttttaacaaactttatcacaagaaa
tattttggcattctacgactataacttaaatttatattattacttttataatatataattgattatagaataatgttgctc
atatcgtttgccaacatctagtactcaaattacactatgttacacttggtaatattaaccgaacttcccctgtccaaatt
agataagaggtaataataaatggaaataattttatagtaaatgaaaatgagaagcgtgtattaaaacaaattttcaata
acagcaatatttcacgaacacaaatatcgaagaatttagaacttaataaagctactatttctaacattctgaacaactta
aaacacaagagtttagttaatgaagtaggagaaggtaatagtactaaaaggtggtggacgaaagcctattttactcgaaat
taaccaaaaatatggctactatatttctatggatttaacatatgattccgttgaattaatgtacaactactttgatgcta
ctatattaaagcaagattcctacgaattaaatgataaaaatgtaagcagtatattacaaattttaaaatctaatataaac
gtctcagaaaaatatgatacgttatatgggttacttggtatatctatatccatacacggtatcgttgacgatgagcaaaa
cataatcaatcttccttttcataaaaatgagaaacgcacatttaccgatgaattaaagtcattcacaaaatgttcctgtcg
ttatagaaaatgaagcaaatttatcagcgctatatgaaaaaagtttatatattaattcaaacataaataatttgattact
ttaagtattcacaagggtataggcgctggcatcctaataaataaaaaactttatcgtggctcaaatggagaggctggaga
gataggtaagacattggttttggaatctataaataacaatgacaacaaatattataaaatcgaagatatatgctcccaag
acgctttaatacagaaaataaataataggttgggcgtcacattgacgtttacagaactaatccaatattacaacgaagga
aattcaattgttgctcatgaaattaaacaatttattaataaaatgacagttctgtgattcataatttgaatacacaatt
taacccagacgctatttatattaactgtcctttaattaatgaattaccaaatatttaaatgaaattaaagagcaattc
tcctgttttctcaaggcagtccagttcaattacatttaactactaatgtaaaacaagctactttattgggtggcac
tttagcaataatgcaaaaaacattaaatataaataacattcaaatgaatattaaataattacagcagtctgagttata
aaatagatatctcggaccgtcataaaaaatttatttgattcaggaaaattttctgtataatagattcaagtta
gtttgtttattaaattaaccaactaaaatgtagaattcgagctcggtacccggggatcctctagagtcgaCCCCA
ACTGGGGTAACCTTTGAGTTCTCTCAGTTGGGGGTAATCAGCATCATGATGTGGTACCACATCATGATGCT
GATTATAAGAATGCGGCCGCCACACTCTAGTGGATCTCGAGTTAATAATTCAGAAGAACTCGTCAAGAAGGCGAT
AGAAGGCGATGCGCTGCGAATCGGGAGCGGCGATACCGTAAAGCACGAGGAAGCGGTCAGCCCATTCGCCGCCAAGC
TCTTCAGCAATATCACGGGTAGCCAACGCTATGTCCTGATAGCGGTCCGCCACACCCAGCCGGCCACAGTCGATGAAT
CCAGAAAAGCGGCCATTTTCCACCATGATATTCGGCAAGCAGGCATCGCCATGGGTCACGACGAGATCCTCGCCGTCG
GCATGCTCGCCTTGAGCCTGGCGAACAGTTCGGCTGGCGCGAGCCCCTGATGCTCTTCGTCCAGATCATCCTGATCGA
CAAGACCGGCTTCCATCCGAGTACGTGCTCGCTCGATGCGATGTTTCGCTTGGTGGTCGAATGGGCAGGTAGCCGGATC
AAGCGTATGCAGCCGCCGCATTGCATCAGCCATGATGGATACTTTCTCGGCAGGAGCAAGGTGAGATGACAGGAGATC
CTGCCCCGGCACTTCGCCCAATAGCAGCCAGTCCCTTCCCGCTTCAGTGACAACGTCGAGCACAGCTGCGCAAGGAAC
GCCCGTCGTGGCCAGCCACGATAGCCGCGCTGCCTCGTCTTGCAGTTCATTCAGGGCACCGGACAGGTCGGTCTTGACA
AAAAGAACCGGGCGCCCCTGCGCTGACAGCCGGAACACGGCGGCATCAGAGCAGCCGATTGTCTGTTGTGCCCAGTCA
TAGCCGAATAGCCTCTCCACCCAAGCGGCCGGAGAACCTGCGTGCAATCCATCTTGTTCAATCATGCGAAACGATCCTC
ATCCTGTCTCTTGATCAGAGCTTGATCCCCTGCGCCATCAGATCCTTGGCGGCGAGAAAGCCATCCAGTTTACTTTGCA
GGGCTTCCCAACCTTACCAGAGGGCGCCCCAGCTGGCAATTCCGGTTCGCTTGCTGTCCATAAAACCGCCCAGTCTAGC
TATCGCCATGTAAGCCCACTGCAAGCTACCTGCTTTCTCTTTGCGCTTGCGTTTTCCCTTGTCCAGATAGCCCAGTAGCT
GACATTCATCCGGGGTCAGCACCGTTTCTGCGGACTGGCTTTCTACGTGCTCGAGgggGgccAAACGGTCTCCAGCTTGGC TABLE 7-continued

| Plasmid Name |
|---|
| Nucleotide Sequence |

TGTTTTGGCGGATGAGAGAAGATTTTCAGCCTGATACAGATTAAATCAGAACGCAGAAGCGGTCTGATAAAACAGAAT
TTGCCTGGCGGCAGTAGCGCGGTGGTCCCACCTGACCCCATGCCGAACTCAGAAGTGAAACGCCGTAGCGCCGATGGT
AGTGTGGGGTCTCCCCATGCGAGAGTAGGGAACTGCCAGGCATCAAATAAAACGAAAGGCTCAGTCGAAAGACTGGG
CCTTTCGTTTTATCTGTTGTTTGTCGGTGAACGCTCTCCTGAGTAGGACAAATCCGCCGGGAGCGGATTTGAACGTTGC
GAAGCAACGGCCCGGAGGGTGGCGGGCAGGACGCCCGCCATAAACTGCCAGGCATCAAATTAAGCAGAAGGCCATCC
TGACGGATGGCCTTTTTGCGTTTCTACAAACTCTTTTGTTTATTTTTCTAAATACATTCAAATATGTATCCGCTCATGACC
AAAATCCCTTAACGTGAGTTTTCGTTCCACTGAGCGTCAGACCCCGTAGAAAAGATCAAAGGATCTTCTTGAGATCCTT
TTTTTCTGCGCGTAATCTGCTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCTTCTAGTGTAGCCGTAGTTA
GGCCACCACTTCAAGAACTCTGTAGCACCGCCTACATACCTCGCTCTGCTAATCCTGTTACCAGTGGCTGCTGCCAGTG
GCGATAAGTCGTGTCTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTTGAGCGTCGATTTTTGTGAT
GCTCGTCAGGGGGGCGGAGCCTATGGAAAAACGCCAGCAACGCGGCCTTTTTACGGTTCCTGGCCTTTTGCTGGCCTTT
TGCTCACATGTTCTTTCCTGCGTTATCCCCTGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCGCATAGTTAAGCCAGT
ATACACTCCGCTATCGCTACGTGACTGGGTCATGGCTGCGCCCCGACACCCGCCAACACCCGCTGACGCGCCCTGACG
GGCTTGTCTGCTCCCGGCATCCGCTTACAGACAAGCTGTGACCGTCTCCGGGAGCTGCATGTGTCAGAGGTTTTCACCG
TCATCACCGAAACGCGCGAGGCAGCAGATCAATTCGCGCGCGAAGGCGAAGCGGCATGCATAATGTGCCTGTCAAAT
GGACGAAGCAGGGATTCTGCAAACCCTATGCTACTCCGTCAAGCCGTCAATTGTCTGATTCGTTACCAATTATGACAAC
TTGACGGCTACATCATTCACTTTTTCTTCACAACCGGCACGGAACTCGCTCGGGCTGGCCCCGGTGCATTTTTTAAATAC
CCGCGAGAAATAGAGTTGATCGTCAAAACCAACATTGCGACCGACGGTGGCGATAGGCATCCGGGTGGTGCTCAAAA
GCAGCTTCGCCTGGCTGATACGTTGGTCCTCGCGCCAGCTTAAGACGCTAATCCCTAACTGCTGGCGGAAAAGATGTG
ACAGACGCGACGGCGACAAGCAAACATGCTGTGCGACGCTGGCGAT pEPSA5

(SEQ ID NO: 100)

ggcggccgcactggcttactatgttggcactgatgagggtgtcagtgaagtgcttcatgtggcaggagaaaaaggct
gcaccggtgcgtcagcagaatatgtgatacaggatatattccgcttcctcgctcactgactcgctacgctcggtcgtt
cgactgcggcgagcggaaatggcttacgaacggggcggagatttcctggaagatgccaggaagatacttaacagggaa
gtgagagggccgcggcaaagccgtttttccataggctccgcccccctgacaagcatcacgaaatctgacgctcaaatc
agtggtggcgaaacccgacaggactataaagataccaggcgtttccccctggcggctccctcgtgcgctctcctgttc
ctgcctttcggtttaccggtgtcattccgctgttatggccgcgtttgtctcattccacgcctgacactcagttccggg
taggcagttcgctccaagctgggactgtatgcacgaaccccccgttcagtccgaccgctgcgccttatccggtaactat
cgtcttgagtccaacccggaaagacatgcaaaagcaccactggcagcagccactggtaattgatttagaggagttagt
cttgaagtcatgcgccggttaaggctaaactgaaaggacaagttttggtgactgcgctcctccaagccagttacctcg
gttcaaagagttggtagctcagagaaccttcgaaaaaccgccctgcaggggtttttcgttttcagagcaagagat
tacgcgcagaccaaaacgatctcaagaagatcatcttatgcggccgcttcttcctgcgttatcccctgattctgtgg
ataaccgtattaccgcctttgagtgagctgataccgctcgccgcagccgaacgaccgagcgcagcgagtcagtgagcg
aggaagcggaagagcgcctgatgcggtattttctccttacgcatctgtgcggtatttcacaccgcataggaagatccc
tcgacctgcaggcatgcaagcttctgtaggttttaggcataaactatatgtttgcctcaaatcttaaaatgcc
ccttaaaattcaaaataaaggcatttaaaatttaaatattcttgtgataaagtttgttaaaaaggagtggtttatg
actgttatgtggttatcgattataggatgtggttttgtattggaatggcatttttttgctatcaaggttattaaaaat
aaaaattagaccacgcatttatgccgagaaaatttattgtgcgttgagaagaaccctaactaaacttgcagacgaat
gtcggcatagcgtgagctattaagccgaccattcgacaagtttgggattgttaagggttccgaggctcaacgtcaat
aaagcaattggaataaagaagcgaaaaaggagaagtcggttcagaaaaagaaggatatggatctggagctgtaatata
aaaaccttcttcaactaacggggcaggttagtgacattagaaaaccgactgtaaaaagtacagtcggcattatctcat
attataaaagccagtcattaggcctatctgacaattcctgaatagagttcataaacaatcctgcatgataaccatcac
aaacagaatgatgtacctgtaaagatagcggtaaatatattgaattaccttttattaatgaattttcctgctgtaataa
tgggtagaaggtaattactattattattgatatttaagttaaacccagtaaatgaagtccatggaataatagaaagag
aaaaagcatttcaggtataggtgtttgggaaacaatttcccgaaccattataltttctactcagaaaggtata
aatcataaaactctttgaagtcattcttacaggagtccaaataccagagatgttttagatacaccatcaaaaattg
tataaagtggctctaacttatcccaataacctaactctccgtcgctattgtaaccagtctaaaagctgtatttgagt
ttatcacccttgtcactaagaaaataaatgcagggtaaaatttatatccttcttgttttatgtttcggtataaaacac
taatatcaatttctgtggttatactaaaagtcgtttgttggttcaaataatgattaaatatctcttttctcttccaat
tgtctaaatcaatttttattaaagttcatttgatatgcctcctaaatttttatctaaagtgaatttaggaggcttactt
gtctgctttcttcattagaatcaatcctttttaaagtcaatattactgtaacataaatatatttttaaaaatatc
ccactttatccaattttcgtttgttgaactaatgggtgattagttgaagaataaaagaccacattaaaaaaattggta
tttgtgtttttttaaaggatttgagcgtagcgaaaaatcctttctttcttatcttgataataagggtaactattgcc
ggcgaggctagttacccttaagttattggtatgactggttttaagcgcaaaaaagttgcttttttcgtacctattaat
gtatcgttttaaatgaatagtaaaaaacatacatagaaagggaaaaagcaactttttttattgtcatagtttgtgaa
aactaagttgttttttatgtgttataacatggaaaagtacactgagaaacaagtacatcagaaataataaagcgataataaaggtcatattggagagaatcaaatggatttagttgaagattgcaatacatttctgtcttttgtagctgataaa
actttagaaaaacagaaattatataaagctaattcttgtaaaaatcgattttgtcctgtctgtgcttggagaaaagct
agaaaagatgcatttgggttttatctttgatgatgcaatatattaagcagcaagagaaaaggagtttatctrntaactt
tgactacacctaatgtaatgagtgatgaattagaaaatgaaataaaacgttataattctttttagaaaacttataa
agagaaaaaagtaggtagtgttataaagggatatgttcgtaagttagagattacatataataaaaaagagatgatt
ataatcctcattttcatgtgttaattgcagtaaataaatcgtatttcacagataaaagatatatattagccaacaag
aatggttagatttatggcgtgatgtaacgggcatttcagaaataacacagttcaagttcaaaaaataagacaaaata
ataataaggaattatatgaaatgcctagttattctggtaaagatagtgattatttaataattcttttagaaacttataa
atttataaatcacttaaaggtaaacaggtattagtttattcaggatatttaaagaggctaaaaagaaattaaaaaa
tgggggatttagattactaaaagaaattgatccaaccgaatataatctatcaaattttttatatttggaaacaaaaga
gtatttagctagtgaactttatgacttaacagaacaagaaaaaagagaaattaatcacaaaatgatagacgaaatcga
ggaagaacaataacaaaatataagtgctaacagtcgtctgcaagtttagttaagggttcttctcaacgcacaataaat
tttctcggcataaatgcgtggtctaattttatttttaataaccttgatagcaaaaaatgccattccaatacaaaacc TABLE 7-continued

| Plasmid Name |
| --- |
| Nucleotide Sequence | acatacctataatcgataaccacataacagtcataaaaccactccttttaacaaactttatcacaagaaatattttg
gcattctacgactataacttaaatttatatttttactttataatatataattgattatagaataatgttgctcatat
cgtttgccaacatctagtactcaaattacactatgttacacttggtaatattaaccgaacttccccctgtccaaattag
ataagaggtaataatatatatggaaataaattttatagtaaatgaaaatgagaagcgtgtattaaaacaaatttttcaata
acagcaatatttcacgaacacaaatatcgaagaatttagaacttaataaagctactatttctaacattctgaacaact
taaaacacaagagtttagttaatgaagtaggagaaggtaatagtactaaaagtggtggacgaaagcctatttttactcg
aaattaaccaaaaatatggctactatatttctatggatttaacatatgattccgttgaattaatgtacaactactttg
atgctactatattaaagcaagattcctacgaattaaatgataaaaatgtaagcagtatattacaaattttaaaatcta
atataaacgtctcagaaaaatatgatacgttatatgggttacttggtatatctatatccatacacgtatcgttgacg
atgagcaaaacataatcaatcttccttttcataaaaatgagaaacgcacatttaccgatgaattaaagtcattcacaa
atgttcctgtcgttatagaaaatgaagcaaatttatcagcgctatatgaaaaaagtttatatattaattcaaacataa
ataatttgattacttaagtattcacaagggtataggcgctggcatcctaataaataaaaaactttatcgtggctcaa
atggagaggctggagagataggtaagacattggttttggaatctataaataacaatgacaacaaatattataaaatcg
aagatatatgctcccaagacgcttaatacagaaaataaataaaggttgggcgtcacattgacgtttacagaactaa
tccaatattacaacgaaggaaattcaattgttgctcatgaaattaaacaatttattaataaaatgacagttctgattc
ataatttgaatacacaattaacccagacgctatttatattaactgtcctttaattaatgaattaccaaatattttaa
atgaaattaaagagcaattctcctgtttttctcaaggcagtccagttcaattacatttaactactaatgtaaaacaag
ctactttattgggtggcacttagcaataatgcaaaaacattaaatataaatacattcaaatgaatattaaataat
tacagcagtctgagttataaaatagatatctcggaccgtcataaaaaatttatttgattcaggaaaattttttctgtat
aatagattcaagttagtttgtttattaaattaaccaactaaaatgtagaattcgagctcggtacccggggatcctcta
gagtcgacctgcagccaagcttgggcttttcagcctgatacagattaaatcagaacgcagaagcggtctgataaaaca
gaatttgcctggcggcagtagcgcggtggtcccacctgaccccatgccgaactcagaagtgaaacgccgtagcgccga
tggtagtgtggggtctccccatgcgagagtagggaactgccaggcatcaaataaaacgaaaggctcagtcgaaagact
gggcctttcgttttatctgttgtttgtcggtgaacgctctcctgagtaggacaaatccgccgggagcggatttgaacg
ttgcgaagcaacggcccggagggtggcgggcaggacgcccgccataaactgccaggcatcaaattaagcagaaggcca
tcctgacggatggcctttttgcgttttctacaaactcttttgtttatttttctaaatacattcaaatatgtatccgctc
atccccatcctatcgatgataagctgtcaaacatgagaattaaatcaatctaaagtatatatgagtaaacttggtctg
acagttaccaatgcttaatcagtgaggcacctatctcagcgatctgtctatttcgttcatccatagttgcctgactcc
ccgtcgtgtagataactacgatacgggagggcttaccatctggccccagtgctgcaatgataccgcgagacccacgct
caccggctccagatttatcagcaataaaccagccagccggaagggccgagcgcagaagtggtcctgcaactttatccg
cctccatccagtctattaattgttgccgggaagctagagtaagtagttcgccagttaatagtttgcgcaacgttgttg
ccattgctacaggcatcgtggtgtcacgctcgtcgtttggtatggcttcattcagctccggttcccaacgatcaaggc
gagttacatgatccccccatgttgtgcaaaaaagcggttagctccttcggtcctccgatcgttgtcagaagtaagttgg
ccgcagtgttatcactcatggttatggcagcactgcataattctcttactgtcatgccatccgtaagatgcttttctg
tgactggtgagtactcaaccaagtcattctgagaatagtgtatgcggcgaccgagttgctcttgcccggcgtcaacac
gggataataccgcgccacatagcagaactttaaaagtgctcatcattggaaaacgctcttcggggcgaaaactctcaa
ggatcttaccgctgttgagatccagttcgatgtaacccactcgtgcacccaactgatcttcagcatcttttactttca
ccagcgtttctgggtgagcaaaaacaggaaggcaaaatgccgcaaaaaagggaataagggcgacacggaaatgttgaa
tactcatactcttcctttttcaatattattgaagcatttatcagggttattgtctcatgagcggatacatatttgaat
gtatttagaaaaataaacaaataggggttccgcgcacatttccccgaaaagtgccacct pEPSA5SynIE2

(SEQ ID NO: 101)

ggcggccgcactggcttactatgttggcactgatgagggtgtcagtgaagtgcttcatgtggcaggagaaaaaaggct
gcaccggtgcgtcagcagaatatgtgatacaggatatattccgcttcctcgctcactgactcgctacgctcggtcgtt
cgactgcggcgagcggaaatggcttacgaacggggcggagatttcctggaagatgccaggaagatacttaacagggaa
gtgagagggccgcggcaaagccgttttccataggctccgcccccctgacaagcatcacgaaatctgacgctcaaatc
agtggtggcgaaacccgacaggactataaagataccaggcgtttccccctggcggctccctcgtgcgctctcctgttc
ctgcctttcggtttaccggtgtcattccgctgttatggccgcgtttgtctcattccacgcctgacactcagttccggg
taggcagttcgctccaagctggactgtatgcacgaaccccccgttcagtccgaccgctgcgccttatccggtaactat
cgtcttgagtccaacccggaaagacatgcaaaagcaccactggcagcagccactggtaattgatttagaggagttagt
cttgaagtcatgcgccggttaaggctaaactgaaaggacaagttttggtgactgcgctcctccaagccagttaccctcg
gttcaaagagttggtagctcagagaaccttcgaaaaaccgccctgcaaggcggttttttcgttttcagagcaagagat
tacgcgcagaccaaaacgatctcaagaagatcatcttatgcggccgcttattcctgcgttatccctgattctgtgga
taaccgtattaccgcctttgagtgagctgataccgctcgccgcagccgaacgaccgagcgcagcgagtcagtgagcga
ggaagcggaagagcgcctgatgcggtattttctccttacgcatctgtgcggtatttcacaccgcataggaagatcct
cgacctgcaggcatgcaagcttctgtaggtttttaggcataaaactatatgatttaccccctaaatctttaaaatgccc
cttaaaattcaaaataaaggcatttaaaatttaaatatttcttgtgataaagtttgttaaaaggagtggttttatga
ctgttatgtggttatcgattataggtatgtggttttgtattggaatggcatttttttgctatcaaggttattaaaaata
aaaattagaccacgcattttatgccgagaaacattattgtgcgttgaagaaccataactaaactttgcagacgaatgt
cggcatagcgtgagctattaagccgaccattcgacaagttttgggattgttaaggggttccgaggctcaacgtcaataa
agcaattggaataaagaagcgaaaaaggagaagtcggttcagaaaaagaagCatgtCatctggagctgtaatataaa
aaccttcttcaactaacggggcaggttagtgacattagaaaaccgactgtaaaaagtacagtcggcattatctcatat
tataaaagccagtcattaggcctatctgaacaattcctgaatagagtttcattaaacaatcctgcatgataacctaccaa
acagaatgatgtacctgtaaagatagcggtaaatatattgaattacctttattaatgaattttcctgctgtaataatg
ggtagaaggtaattactattattattgatatttaagttaaacccagtaaatgaagtccatggaataatagaaagagaa
aaagcattttcaggtataggtgttttgggaaacaaatttcccgaaccattatattctctacatcagaaaggtataaa
tcataaaactctttgaagtcattcttttacaggagtccaaatacagagaatgttttagatacaccatcaaaaattgta
taaagtggctctaacttatcccaataacctaactctccgtcgctattgtaaccagttctaaaagctgtatttgagttt
atcacccttgtcactaagaaaataaatgcagggtaaaatttatatccttcttgttttatgtttcggtataaaacacta
atatcaatttctgtggtatactaaaagtcgtttgttggttcaaataatgattaaatatctcttttctcttccaattg
tctaaatcaattttattaaagttcatttgatatgcctcctaaattttttatctaaagtgaatttaggaggcttacttgt
ctgattatcattagaatcaatcatttttaaaagtcaatattactgtaacataaataatatttttaaaaatatcccact
ttatccaatttttcgtttgttgaactaatgggtgattagttgaagaataaaagaccacattaaaaaatgtggtcttttg
tgttttttaaaggatttgagcgtagcgaaaatccttttcttttcttcttgataatagggtaactattgccggcg
aggctagttaccttaagttattggtatgactggttttaagcgcaaaaaagttgattttcgtacctattaatgtatc
gttttaaaatgaatagataaaaaacatacatagaaagggggaaaagcaacttttttttattgtcatagtttgtgaaaacta

TABLE 7-continued

Plasmid Name
Nucleotide Sequence agttgtttttatgtgttataacatggaaaagtatactgagaaaaaacaaagaaatcaagtatttcagaaatttattaa
acgtcatattggagagaatcaaatggatttagttgaagattgcaatacatttctgtcttttgtagctgataaaacttt
agaaaaacagaaattatataaagctaattcttgtaaaaatcgattttgtcctgtctgtgcttggagaaaagctagaaa
agatgcattgggtttatctttgatgatgcaatatattaagcagcaagagaaaaaggagtttatattttaactttgact
acacctaatgtaatgagtgatgaattagaaaatgaaataaaacgttataataattcttttagaaaacttataaagaga
aaaaaagtaggtagtgttataaagggatatgttcgtaagttagagattacatataataaaaaaagagatgattataat
cctcattttcatgtgttaattgcagtaaataaatcgtatttcacagataaaagatattatattagccaacaagaatgg
ttagatttatggcgtgatgtaacgggcatttcagaaataacacaagttcaagttcaaaaaataagacaaaataataat
aaagaattatatgaaatggctaagtattctggtaaagatagtgattatttaataaatcaaaaagtattgatgcattt
ataaatcacttaaaggtaaacaggtattagttttattcaggattatttaaagaggctaaaaagaaattaaaaaatgggg
atttagattacttaaaagaaattgatccaaccgaatatatctatcaattttttatatttggaaacaaaaagagtatt
tagctagtgaacttttatgacttaacagaacaagaaaaaagagaaattaatcacaaaatgatagacgaaatcgaggaag
aacaataacaaaatataagtgctaacagtcgtctgcaagtttagttaagggttcttctcaacgcacaataaattttct
cggcataaatgcgtggtctaattttttattttaataacttgatagcaaaaaatgccattccaatacaaaaccacata
cctataatcgataaccacataacagtcataaaaccactccttttttaacaaactttatcacaagaaatattttggcatt
ctacgactataaacttaaatttatatttttttacttttataatatataattgattatagaataatgttgctcatatcgttt
gccaacatctagtactcaaattacactatgttacacttggtaatatttaaccgaacttcccctgtccaaattagataag
aggtaataataaatggaaaataattttatagtaaatgaaaatgaaagcgtgtattaaacaaattttcaataacagc
aatatttcacgaacacaaatatcgaagaatttagaacttaataaagctactatttctaacattctgaacaacttaaaa
cacaagagtttagttaatgaagtaggagaaggtaatagtactaaaagtggtggacgaaagcctattttactcgaaatt
aaccaaaaatatggctactatatttctatggatttaacatatgattccgttgaattaatgtacaactactttgatgct
actatattaaagcaagattcctacgaattaaatgataaaaatgcaggcagttaagcagttatacaaattttaaaatctaatata
aacgtctcagaaaaatatgatacgttatatgggttacttggtatatctatatccatacacggtatcgttgacgatgag
caaaacataatcaatcttccttttcataaaaatgagaaacgcacatttaccgatgaattaaagtcattcacaaatgtt
cctgtcgttatagaaaatgaagcaaatttatcagcgctatatgaaaaagtttatatattaattcaaacataaataat
ttgattactttaagtattcacaagggtataggcgctggcatcctaataaatacaaaactttatcgtggctcaaatgga
gaggctggagagataggtaagacattggttttggaatctataaataacaatgacaacaaatattaaaatcgaagat
atatgctcccaagacgcttaatacagaaaataaataataggttggggcgtcacattgacgtttacagaactaatccaa
tattacaacgaaggaaattcaattgttgctcatgaaattaaacaatttattaataaaatgacagttctgattcataat
ttgaatacacaatttaacccagacgctatttatattaactgtccttttaattaatgaattaccaaatattttaaatgaa
attaaagacaattctcctgttttcaaggcagtccagttcaattacatttaactactaatgtaaaacaagctact
ttattgggtggcactttagcaataatgcaaaaaacattaaatataaataacattcaaatgaatattaaataattacag
cagtctgagttataaaatagatatctcggaccgtcataaaaaatttatttgattcaggaaaattttctgtataatag
attcaagttagtttgttttattaaattaaccaactaaaatgtagaattcgagctcggtacccggggatcctctagagtc
gacctgcagcaaagcttggcctttcagcctgatacagattaaatcgaaacgcagaagcggtagataaaacagaattt
gcctggcggcagtagcgcggtggtcccacctgacccatgccgaactcagaagtgaaacgccgtagcgccgatggtag
tgtggggtctcccatgcgagagtagggaactgccaggcatcaaatataaacgaaaggctcagtcgaaagactgggcct
ttcgttttatctgttgtttgtcggtgaacgctacctgagtaggacaaatccgccgggagcggatttgaacgttgcgaa
gcaacgcccggagggtggcgggcaggacgcccgccataaactgccaggcatcaaattaagcagaaggccatcctgac
ggatggcctttttgcgtttctacaaactcttttgttttatttttctaaatacattcaaatatgtatccgctcatGccca
tcGtatcgatgataagctgtcaaacatgagaattaaatcaatctaaagtatatatgagtaaacttggtctgacagtta
ccaatgcttaatcagtgaggcacctatctcagcgatctgtctatttcgttcatccatagttgcctgactccccgtcgt
gtagataactacgatacgggagggcttaccatctggccccagtgctgcaatgataccgcgagacccacgctcaccggc
tccagatttatcagcaataaaccagccagccggaagggccgagcgcagaagtggtcctgcaactttatccgcctccat
ccagtctattaattgttgccgggaagctagagtaagtagttcgccagttaatagtttgcgcaacgttgttgccattgc
tacTggcatcgtAgtgtcacgctcgtcgtttggtatggcttcattcagctccggttcccaacgatcaaggcgagttac
atgatcccccatgttgtgcaaaaaagcggttagctccttcggtcctccgatcgttgtcagaagtaagttggccgcagt
gttatcactcatggttatggcagcactgcataattctcttactgtcatgccatccgtaagatgatttctgtgactggt
gagtactcaaccaagtcattctgagaatagtgtatgcggcgaccgagttgctcttgcccggcgtcaacacgggataat
accgcgccacatagcagaactttaaaagtgctcatcattggaaaacgcttcttcggggcgaaaactctcaaggatctta
ccgctgttgagatccagttcgatgtaacccactcgtgcacccaactgatcttcagcatcttttactttcaccagcgtt
tctgggtgagcaaaaacaggaaggcaaatgccgcaaaaaagggaataagggcgacacgaaatgttgaatactcata
ctcttccttttcaatattattgaagcatttatcagggttattgtctcatgagcggatacatatttgaatgtatttag
aaaaataaacaaatagggggttccgcgcacatttccccgaaaagtgccacct

The invention claimed is:

1. An engineered, minicircle producing bacterium comprising:
    a parental plasmid comprising a minicircle nucleic acid sequence comprising an exogenous nucleic acid sequence and a plurality of restriction sites outside of the minicircle nucleic acid sequence,
    wherein at least one endogenous methyltransferase comprising at least one of a Dam methyltransferase, a Dcm methyltransferase, a HsdM methyltransferase, or a combination thereof, is absent or non-functional in the engineered bacterium, such that the engineered bacterium has reduced DNA-methylation capability and the exogenous nucleic acid sequence lacks methylation at a plurality of methylation cites that would be methylated in a reference bacterium of the same species as the engineered bacterium.

2. The engineered bacterium of claim 1, wherein the at least one endogenous methyltransferase is non-functional in the engineered bacterium, and the engineered bacterium comprises a modification in a gene encoding a respective endogenous methyltransferase of the at least one endogenous methyltransferase.

3. The engineered bacterium of claim 1, wherein the at least one endogenous methyltransferase methylates a cytosine residue of a sequence CCWGG, wherein the W is A or T, the at least one endogenous methyltransferase methylates an adenosine residue of a sequence GATC, a sequence $AACN_6GTGC$, or both, or the at least one endogenous methyltransferase methylates a cytosine residue and an adenosine residue.

4. The engineered bacterium claim 1, wherein the engineered bacterium is *Escherichia coli*.

5. The engineered bacterium of claim 1, further comprising at least one of an inducible φC31 integrase or an inducible I-SceI homing endonuclease.

6. A kit comprising an engineered bacterium of claim 1.

7. A method, comprising:
    producing a minicircle comprising the exogenous DNA sequence comprised in the parental plasmid in a first bacterium that is an engineered bacterium of claim 1; and
    transforming the minicircle into a second bacterium, the minicircle lacking methylation at a plurality of methylation sites that would be methylated in a reference bacterium of the same species as the engineered bacterium and, thereby, resisting degradation when transformed into the second bacterium.

8. A method, comprising:
    transforming a parental plasmid into an engineered bacterium,
    wherein the parental plasmid comprises a minicircle nucleic acid sequence comprising an exogenous nucleic acid sequence and a plurality of restriction sites outside of the minicircle nucleic acid sequence, and
    wherein at least one endogenous methyltransferase comprising at least one of a Dam methyltransferase, a Dcm methyltransferase, a HsdM methyltransferase, or a combination thereof, is absent or non-functional in the engineered bacterium, such that the engineered bacterium has reduced DNA-methylation capability and the exogenous nucleic acid sequence lacks methylation at a plurality of methylation cites that would be methylated in a reference bacterium of the same species as the engineered bacterium; and
    producing a minicircle comprising the minicircle nucleic acid sequence, wherein the minicircle lacks methylation at a plurality of methylation sites that would be methylated in a reference bacterium of the same species as the engineered bacterium.

9. The method of claim 8, wherein at least one endogenous methyltransferase is non-functional in the engineered bacterium, and the engineered bacterium comprises a modification in a gene encoding a respective endogenous methyltransferase of the at least one endogenous methyltransferase.

10. The method of claim 8, wherein the at least one endogenous methyltransferase methylates a cytosine residue of a sequence CCWGG, wherein the W is A or T, the at least one endogenous methyltransferase methylates an adenosine residue of a sequence GATC, a sequence $AACN6GTGC$, or both, or the at least one endogenous methyltransferase methylates a cytosine residue and an adenosine residue.

11. The method of claim 7, wherein at least one endogenous methyltransferase is non-functional in the engineered bacterium, and the engineered bacterium comprises a modification in a gene encoding a respective endogenous methyltransferase of the at least one endogenous methyltransferase.

12. The method of claim 7, wherein the at least one endogenous methyltransferase methylates a cytosine residue of a sequence CCWGG, wherein the W is A or T, the at least one endogenous methyltransferase methylates an adenosine residue of a sequence GATC, a sequence $AACN6GTGC$, or both, or the at least one endogenous methyltransferase methylates a cytosine residue and an adenosine residue.

* * * * *